US012747298B2

(12) United States Patent
Trinklein et al.

(10) Patent No.: US 12,747,298 B2
(45) Date of Patent: Sep. 29, 2026

(54) MULTI-SPECIFIC ANTIBODIES BINDING TO BCMA

(71) Applicant: TeneoBio, Inc., Thousand Oaks, CA (US)

(72) Inventors: Nathan Trinklein, Newark, CA (US); Katherine Harris, Newark, CA (US); Harbani Malik, Newark, CA (US); Ute Schellenberger, Newark, CA (US); Omid Vafa, Newark, CA (US); Shelley Force Aldred, Newark, CA (US)

(73) Assignee: TeneoBio, Inc., Thousand Oaks, CA (US)

( * ) Notice: Subject to any disclaimer, the term of this patent is extended or adjusted under 35 U.S.C. 154(b) by 848 days.

(21) Appl. No.: 18/002,472

(22) PCT Filed: Jun. 30, 2021

(86) PCT No.: PCT/US2021/039961

§ 371 (c)(1),
(2) Date: Jun. 12, 2023

(87) PCT Pub. No.: WO2022/006316

PCT Pub. Date: Jan. 6, 2022

(65) Prior Publication Data

US 2023/0257473 A1 Aug. 17, 2023

Related U.S. Application Data

(60) Provisional application No. 63/046,477, filed on Jun. 30, 2020.

(51) Int. Cl.
*C07K 16/00* (2006.01)
*A61K 39/395* (2006.01)
*C07K 16/18* (2006.01)
*C07K 16/28* (2006.01)

(52) U.S. Cl.
CPC .......... *C07K 16/2878* (2013.01); *C07K 16/18* (2013.01); *C07K 2317/21* (2013.01); *C07K 2317/31* (2013.01); *C07K 2317/35* (2013.01)

(58) Field of Classification Search
None
See application file for complete search history.

(56) References Cited

U.S. PATENT DOCUMENTS 4,275,149 A 6/1981 Litman et al.
4,816,567 A 3/1989 Cabilly et al.
5,225,539 A 7/1993 Winter
5,500,360 A 3/1996 Ahlquist et al.
5,500,362 A 3/1996 Robinson et al.
5,585,089 A 12/1996 Queen et al.
5,585,097 A 12/1996 Bolt et al.
5,595,097 A 1/1997 Anderson
5,693,761 A 12/1997 Queen et al.
5,821,337 A 10/1998 Carpenter et al.
5,929,212 A 7/1999 Jolliffe et al.
5,968,509 A 10/1999 Gorman et al.
6,037,453 A 3/2000 Jardieu et al.
6,407,213 B1 6/2002 Carter et al.
6,548,640 B1 4/2003 Winter
6,706,265 B1 3/2004 Bolt et al.
6,750,325 B1 6/2004 Jolliffe et al.
6,982,321 B2 1/2006 Winter
7,083,785 B2 8/2006 Browning et al.
7,262,276 B2 8/2007 Huang et al.
7,381,803 B1 6/2008 Weiner et al.
7,541,513 B2 6/2009 Bruggeman et al.
7,635,472 B2 12/2009 Kufer et al.
7,691,804 B2 4/2010 Jeffrey et al.
7,728,114 B2 6/2010 Mach et al.
7,862,813 B2 1/2011 Bjork et al.
8,106,163 B2 1/2012 Heusser et al.
8,207,303 B2 6/2012 Cardarelli et al.
8,236,308 B2 8/2012 Kischel et al.
8,367,888 B2 2/2013 Bruggeman et al.
8,703,485 B2 4/2014 Buelow
8,883,150 B2 11/2014 Craig et al.
9,034,324 B2 5/2015 Kalled et al.
9,096,651 B2 8/2015 Igawa et al.
9,150,664 B2 10/2015 Kufer et al.
9,228,016 B2 1/2016 Wang et al.
9,340,621 B2 5/2016 Kufer et al.
9,365,655 B2 6/2016 Craig et al.
9,587,036 B2 3/2017 Kufer
9,598,500 B2 3/2017 Kufer et al.
9,650,430 B2 5/2017 Browning et al.
9,657,102 B2 5/2017 Smith et al.
9,765,342 B2 9/2017 Kochenderfer
10,202,452 B2 2/2019 Tan et al.
(Continued)

FOREIGN PATENT DOCUMENTS

CA 2828347 A1 9/2012
CA 3100566 A1 12/2019
(Continued)

OTHER PUBLICATIONS

Altshuler E.P., et al., “Obtaining Recombinant Antibodies and Ways to Increase Their Affinity,” Uspekhi Biological Chemistry, 2010, vol. 50, p. 207.

(Continued)

*Primary Examiner* — Meera Natarajan
(74) *Attorney, Agent, or Firm* — Haynes and Boone, LLP

(57) ABSTRACT

Multi-specific, human heavy chain antibodies (e.g., UniAbsm) binding to BCMA are disclosed, along with methods of making such antibodies, compositions, including pharmaceutical compositions, comprising such antibodies, and their use to treat disorders that are characterized by the expression of BCMA.

26 Claims, 13 Drawing Sheets

Specification includes a Sequence Listing.

(56) References Cited

U.S. PATENT DOCUMENTS

| | | | |
|---|---|---|---|
| 10,465,009 | B2 | 11/2019 | Armitage et al. |
| 10,465,010 | B2 | 11/2019 | Wang et al. |
| 10,494,416 | B2 | 12/2019 | Browning et al. |
| 10,766,969 | B2 | 9/2020 | Kufer et al. |
| 10,934,363 | B2 | 3/2021 | Fan et al. |
| 11,072,656 | B2 | 7/2021 | Smith et al. |
| 11,155,621 | B2 | 10/2021 | Smith et al. |
| 11,186,639 | B2 | 11/2021 | Harris et al. |
| 11,384,153 | B2 | 7/2022 | Smith et al. |
| 11,390,681 | B2 | 7/2022 | Harris et al. |
| 11,421,027 | B2 | 8/2022 | Trinklein et al. |
| 11,427,642 | B2 | 8/2022 | Trinklein et al. |
| 11,434,299 | B2 | 9/2022 | Force Aldred et al. |
| 11,505,606 | B2 | 11/2022 | Trinklein et al. |
| 11,613,572 | B2 | 3/2023 | Trinklein et al. |
| 11,905,326 | B2 | 2/2024 | Trinklein et al. |
| 11,970,540 | B2 | 4/2024 | Trinklein et al. |
| 2001/0024811 | A1 | 9/2001 | Khosla et al. |
| 2001/0024812 | A1 | 9/2001 | Guegler et al. |
| 2002/0066516 | A1 | 6/2002 | Cornell |
| 2004/0229310 | A1 | 11/2004 | Simmons |
| 2005/0048572 | A1 | 3/2005 | Reilly et al. |
| 2006/0008548 | A1 | 1/2006 | Tung |
| 2007/0065437 | A1 | 3/2007 | Elson et al. |
| 2007/0071675 | A1 | 3/2007 | Wu et al. |
| 2007/0212733 | A1 | 9/2007 | Martin |
| 2009/0098134 | A1 | 4/2009 | Buelow |
| 2010/0122358 | A1 | 5/2010 | Bruggeman et al. |
| 2010/0150918 | A1 | 6/2010 | Kufer |
| 2011/0129458 | A1 | 6/2011 | Dolk et al. |
| 2011/0293619 | A1 | 12/2011 | Kufer et al. |
| 2013/0101599 | A1 | 4/2013 | Borages et al. |
| 2013/0129729 | A1 | 5/2013 | Kischel et al. |
| 2013/0156769 | A1 | 6/2013 | Kufer et al. |
| 2013/0195888 | A1 | 8/2013 | Wang et al. |
| 2013/0216544 | A1 | 8/2013 | Bachmann |
| 2013/0273055 | A1 | 10/2013 | Borges et al. |
| 2013/0273066 | A1 | 10/2013 | Borges et al. |
| 2013/0280280 | A1 | 10/2013 | Algate et al. |
| 2014/0056897 | A1 | 2/2014 | Buelow et al. |
| 2014/0088295 | A1 | 3/2014 | Smith et al. |
| 2014/0220021 | A1 | 8/2014 | Shibayama et al. |
| 2015/0118251 | A1 | 4/2015 | Deslandes |
| 2015/0266966 | A1 | 9/2015 | Smith et al. |
| 2015/0337054 | A1 | 11/2015 | Gardner, II et al. |
| 2015/0368351 | A1 | 12/2015 | Vu et al. |
| 2015/0376287 | A1 | 12/2015 | Vu et al. |
| 2016/0046724 | A1 | 2/2016 | Bogdon et al. |
| 2016/0075785 | A1 | 3/2016 | Ast et al. |
| 2016/0159894 | A1 | 6/2016 | Hartmann et al. |
| 2016/0166689 | A1 | 6/2016 | Adler et al. |
| 2016/0194399 | A1 | 7/2016 | Irving et al. |
| 2016/0272711 | A1 | 9/2016 | Sahin et al. |
| 2016/0355591 | A1 | 12/2016 | Goldenberg et al. |
| 2017/0051068 | A1 | 2/2017 | Pillarisetti et al. |
| 2017/0081411 | A1 | 3/2017 | Engels et al. |
| 2017/0240612 | A1 | 8/2017 | Bachmann et al. |
| 2018/0222991 | A1 | 8/2018 | Vu et al. |
| 2018/0344870 | A1 | 12/2018 | Xiao et al. |
| 2019/0026390 | A1 | 1/2019 | Yamagishi |
| 2019/0062395 | A1 | 2/2019 | Merchant et al. |
| 2019/0070290 | A1 | 3/2019 | Kischel et al. |
| 2019/0106504 | A1 | 4/2019 | Wu et al. |
| 2019/0151448 | A1 | 5/2019 | Abel et al. |
| 2019/0225671 | A1 | 7/2019 | Van Schooten et al. |
| 2019/0233518 | A1 | 8/2019 | Fayadat-Dilman et al. |
| 2019/0263904 | A1 | 8/2019 | Trinklein et al. |
| 2019/0284294 | A1 | 9/2019 | Deslandes et al. |
| 2019/0352412 | A1 | 11/2019 | Force Aldred et al. |
| 2020/0048348 | A1 | 2/2020 | Trinklein et al. |
| 2020/0078399 | A1 | 3/2020 | Fan et al. |
| 2020/0085839 | A1 | 3/2020 | Sidransky et al. |
| 2020/0095305 | A1 | 3/2020 | Browning et al. |
| 2020/0095319 | A1 | 3/2020 | Kufer et al. |
| 2020/0123269 | A1 | 4/2020 | Fan et al. |
| 2020/0129617 | A1 | 4/2020 | Brownstein et al. |
| 2020/0131262 | A1 | 4/2020 | Ehninger |
| 2020/0138865 | A1 | 5/2020 | Kochenderfer et al. |
| 2020/0157232 | A1 | 5/2020 | Trinklein et al. |
| 2020/0181228 | A1 | 6/2020 | Bachmann et al. |
| 2020/0190205 | A1 | 6/2020 | Adams et al. |
| 2020/0332000 | A1 | 10/2020 | McAuley et al. |
| 2020/0339685 | A1 | 10/2020 | Schellenberger et al. |
| 2021/0047402 | A1 | 2/2021 | Trinklein et al. |
| 2021/0047407 | A1 | 2/2021 | Christian et al. |
| 2021/0095022 | A1 | 4/2021 | Force Aldred et al. |
| 2021/0139577 | A1 | 5/2021 | Dillon et al. |
| 2021/0139584 | A1 | 5/2021 | Minella et al. |
| 2021/0147564 | A1 | 5/2021 | Trinklein et al. |
| 2021/0163620 | A1 | 6/2021 | Granda et al. |
| 2021/0284732 | A1 | 9/2021 | Zugmaier et al. |
| 2021/0309751 | A1* | 10/2021 | Bachmann ......... C07K 14/7051 |
| 2021/0332133 | A1 | 10/2021 | Force Aldred et al. |
| 2021/0340255 | A1 | 11/2021 | Harris et al. |
| 2021/0341487 | A1 | 11/2021 | Partridge et al. |
| 2021/0355215 | A1 | 11/2021 | Jorgensen et al. |
| 2021/0388106 | A1 | 12/2021 | Van Schooten et al. |
| 2021/0395298 | A1 | 12/2021 | Bondarenko et al. |
| 2021/0403587 | A1 | 12/2021 | Buelow et al. |
| 2022/0025047 | A1 | 1/2022 | Trinklein et al. |
| 2022/0041742 | A1 | 2/2022 | Adams et al. |
| 2022/0064336 | A1 | 3/2022 | Kufer et al. |
| 2022/0089729 | A1 | 3/2022 | Harris et al. |
| 2022/0098324 | A1 | 3/2022 | Weiner et al. |
| 2022/0137010 | A1 | 5/2022 | Wen |
| 2022/0144947 | A1 | 5/2022 | Smith et al. |
| 2022/0195068 | A1 | 6/2022 | Van Schooten et al. |
| 2022/0251243 | A1 | 8/2022 | Kufer et al. |
| 2022/0259547 | A1 | 8/2022 | Khurshid |
| 2022/0306741 | A1 | 9/2022 | Sharma et al. |
| 2022/0306758 | A1 | 9/2022 | Smith et al. |
| 2022/0332820 | A1 | 10/2022 | Harris et al. |
| 2022/0356268 | A1 | 11/2022 | Kufer et al. |
| 2022/0378908 | A1 | 12/2022 | Zhu et al. |
| 2022/0389055 | A1 | 12/2022 | Davis et al. |
| 2022/0396599 | A1 | 12/2022 | Wang et al. |
| 2022/0403035 | A1 | 12/2022 | Anlahr et al. |
| 2023/0045100 | A1 | 2/2023 | Force Aldred et al. |
| 2023/0057602 | A1 | 2/2023 | Burgess et al. |
| 2023/0060847 | A1 | 3/2023 | Trinklein et al. |
| 2023/0082151 | A1 | 3/2023 | Trinklein et al. |
| 2023/0272075 | A1 | 8/2023 | Trinklein et al. |

FOREIGN PATENT DOCUMENTS

| | | | |
|---|---|---|---|
| CN | 1551886 | A | 12/2004 |
| CN | 1889979 | A | 1/2007 |
| CN | 101627055 | A | 1/2010 |
| CN | 102119174 | A | 7/2011 |
| CN | 1889979 | B | 9/2012 |
| CN | 103608039 | A | 2/2014 |
| CN | 103619876 | A | 3/2014 |
| CN | 104379179 | A | 2/2015 |
| CN | 104877026 | A | 9/2015 |
| CN | 104968682 | A | 10/2015 |
| CN | 105143263 | A | 12/2015 |
| CN | 105384825 | A | 3/2016 |
| CN | 105457024 | A | 4/2016 |
| CN | 105777906 | A | 7/2016 |
| CN | 106459203 | A | 2/2017 |
| CN | 106687483 | A | 5/2017 |
| CN | 103703024 | B | 11/2017 |
| CN | 105384825 | B | 6/2018 |
| CN | 101874042 | B | 9/2018 |
| CN | 104114578 | B | 10/2018 |
| CN | 101874042 | B9 | 1/2019 |
| CN | 104877026 | B | 10/2019 |
| EA | 201591091 | A1 | 2/2016 |
| EP | 1223964 | B1 | 4/2007 |
| EP | 2762496 | A1 | 8/2014 |
| EP | 2762497 | A1 | 8/2014 |
| EP | 1210425 | B2 | 6/2015 |
| EP | 2970472 | A1 | 1/2016 |
| EP | 1806143 | B1 | 6/2016 |

(56) References Cited

FOREIGN PATENT DOCUMENTS

| | | | |
|---|---|---|---|
| EP | 2780374 | B1 | 8/2019 |
| EP | 2780375 | B1 | 9/2019 |
| EP | 3611193 | A1 | 2/2020 |
| EP | 3623385 | A1 | 3/2020 |
| EP | 3819007 | A1 | 5/2021 |
| EP | 3830122 | A1 | 6/2021 |
| EP | 3912997 | A2 | 11/2021 |
| EP | 3411402 | B1 | 12/2021 |
| EP | 3974453 | A2 | 3/2022 |
| EP | 4039709 | A1 | 8/2022 |
| EP | 4058148 | A1 | 9/2022 |
| EP | 4171750 | A1 | 5/2023 |
| JP | 2001077342 | A | 3/2001 |
| JP | 2012504403 | A | 2/2012 |
| JP | 2012521211 | A5 | 5/2013 |
| JP | 2013528569 | A | 7/2013 |
| JP | 2014500879 | A | 1/2014 |
| JP | 2014515598 | A | 7/2014 |
| JP | 2014520088 | A | 8/2014 |
| JP | 2015521032 | A | 7/2015 |
| JP | 5836927 | B2 | 12/2015 |
| JP | 2015535002 | A | 12/2015 |
| JP | 2016500256 | A | 1/2016 |
| JP | 2016538275 | A | 12/2016 |
| JP | 6923292 | B2 | 8/2021 |
| JP | 7030109 | B2 | 3/2022 |
| NZ | 754713 | A | 11/2025 |
| RU | 2492186 | C2 | 9/2013 |
| RU | 2561457 | C2 | 8/2015 |
| WO | 1996/027011 | A1 | 9/1996 |
| WO | 1996/032478 | A1 | 10/1996 |
| WO | 1997/034631 | A1 | 9/1997 |
| WO | 1998/050431 | A2 | 11/1998 |
| WO | 2000/040716 | A2 | 7/2000 |
| WO | 2001/012812 | A2 | 2/2001 |
| WO | 2001/024811 | A1 | 4/2001 |
| WO | 2001/024812 | A1 | 4/2001 |
| WO | 2001/087977 | A2 | 11/2001 |
| WO | 2002/066516 | A2 | 8/2002 |
| WO | 2004/106383 | A1 | 12/2004 |
| WO | 2005/040220 | A1 | 5/2005 |
| WO | 2005/061547 | A2 | 7/2005 |
| WO | 2006/008548 | A2 | 1/2006 |
| WO | 2007/042261 | A2 | 4/2007 |
| WO | 2007042289 | A2 | 4/2007 |
| WO | 2007055916 | A2 | 5/2007 |
| WO | 2007/066109 | A1 | 6/2007 |
| WO | 2001/077342 | A1 | 10/2007 |
| WO | 2007/117600 | A2 | 10/2007 |
| WO | 2007117505 | A2 | 10/2007 |
| WO | 2008/119565 | A2 | 10/2008 |
| WO | 2008/119566 | A2 | 10/2008 |
| WO | 2008/119567 | A2 | 10/2008 |
| WO | 2008151081 | A1 | 12/2008 |
| WO | 2009/055669 | A2 | 4/2009 |
| WO | 2009041643 | A1 | 4/2009 |
| WO | 2009/132058 | A2 | 10/2009 |
| WO | 2010007082 | A1 | 1/2010 |
| WO | 2010/037835 | A2 | 4/2010 |
| WO | 2010/037836 | A2 | 4/2010 |
| WO | 2010/037837 | A2 | 4/2010 |
| WO | 2010/037838 | A2 | 4/2010 |
| WO | 2010/104949 | A2 | 9/2010 |
| WO | 2010/109165 | A2 | 9/2010 |
| WO | 2011/097603 | A1 | 8/2011 |
| WO | 2012/066058 | A1 | 5/2012 |
| WO | 2012/122512 | A1 | 9/2012 |
| WO | 2012122528 | A1 | 9/2012 |
| WO | 2012/143498 | A1 | 10/2012 |
| WO | 2012145714 | A2 | 10/2012 |
| WO | 2012162067 | A2 | 11/2012 |
| WO | 2012/163805 | A1 | 12/2012 |
| WO | 2013022091 | A1 | 2/2013 |
| WO | 2013/072406 | A1 | 5/2013 |
| WO | 2013/072415 | A1 | 5/2013 |
| WO | 2013/154760 | A1 | 10/2013 |
| WO | 2014/022540 | A1 | 2/2014 |
| WO | 2014/047231 | A1 | 3/2014 |
| WO | 2014/068079 | A1 | 5/2014 |
| WO | 2014/089335 | A2 | 6/2014 |
| WO | 2014/093908 | A2 | 6/2014 |
| WO | 2014112144 | A1 | 7/2014 |
| WO | 2014/122144 | A1 | 8/2014 |
| WO | 2014122143 | A1 | 8/2014 |
| WO | 2014140248 | A1 | 9/2014 |
| WO | 2015/095412 | A1 | 6/2015 |
| WO | 2015/121383 | A1 | 8/2015 |
| WO | 2015/149077 | A1 | 10/2015 |
| WO | 2015158671 | A1 | 10/2015 |
| WO | 2016/014789 | A2 | 1/2016 |
| WO | 2016/030414 | A1 | 3/2016 |
| WO | 2016/048938 | A1 | 3/2016 |
| WO | 2016/062990 | A1 | 4/2016 |
| WO | 2016/079081 | A1 | 5/2016 |
| WO | 2016/079177 | A1 | 5/2016 |
| WO | 2016079076 | A1 | 5/2016 |
| WO | 2016/094304 | A2 | 6/2016 |
| WO | 2016/113555 | A1 | 7/2016 |
| WO | 2016124670 | A1 | 8/2016 |
| WO | 2016128487 | A1 | 8/2016 |
| WO | 2016/187546 | A1 | 11/2016 |
| WO | 2017/025038 | A1 | 2/2017 |
| WO | 2017/031104 | A1 | 2/2017 |
| WO | 2017023761 | A1 | 2/2017 |
| WO | 2017053856 | A1 | 3/2017 |
| WO | 2015/063339 | A1 | 5/2017 |
| WO | 2017/081211 | A2 | 5/2017 |
| WO | 2017/223111 | A1 | 12/2017 |
| WO | 2018/039180 | A1 | 3/2018 |
| WO | 2018/052503 | A1 | 3/2018 |
| WO | 2018083204 | A1 | 5/2018 |
| WO | 2018114795 | A1 | 6/2018 |
| WO | 2018119215 | A1 | 6/2018 |
| WO | 2018/237006 | A1 | 12/2018 |
| WO | 2018/237037 | A2 | 12/2018 |
| WO | 2018224660 | A1 | 12/2018 |
| WO | 2019/000223 | A1 | 1/2019 |
| WO | 2019/006072 | A1 | 1/2019 |
| WO | 2019055689 | A1 | 3/2019 |
| WO | 2019075413 | A1 | 4/2019 |
| WO | 2019126756 | A1 | 6/2019 |
| WO | 2019/133761 | A1 | 7/2019 |
| WO | 2019164891 | A | 8/2019 |
| WO | 2019238722 | A1 | 12/2019 |
| WO | 2019241686 | A1 | 12/2019 |
| WO | 2020/018922 | A1 | 1/2020 |
| WO | 2020025596 | A1 | 2/2020 |
| WO | 2020061478 | A2 | 3/2020 |
| WO | 2020087065 | A1 | 4/2020 |
| WO | 2020/206330 | A1 | 10/2020 |
| WO | 2020252366 | A1 | 12/2020 |
| WO | 2021094000 | A1 | 5/2021 |
| WO | 2021127489 | A1 | 6/2021 |
| WO | 2021222578 | A1 | 11/2021 |
| WO | 2021222616 | A1 | 11/2021 |
| WO | 2021228783 | A1 | 11/2021 |
| WO | 2022006316 | A1 | 1/2022 |
| WO | 2022103781 | A1 | 5/2022 |
| WO | 2022109010 | A1 | 5/2022 |
| WO | 2022183074 | A2 | 9/2022 |
| WO | 2022183101 | A1 | 9/2022 |
| WO | 2022212848 | A1 | 10/2022 |
| WO | 2022216864 | A1 | 10/2022 |
| WO | 2022221698 | A1 | 10/2022 |
| WO | 2022271987 | A1 | 12/2022 |
| WO | 2023004197 | A1 | 1/2023 |

OTHER PUBLICATIONS

Koiko R., "Immunology: Textbook, Moscow," Academia Publishing Center, 2008, pp. 61-62.

Kuznetsova I.M, et al., "Structural Dynamics, Stability and Folding of Proteins," Tsitologiya, 2005, vol. 47, No. 11, pp. 943-952.

(56) References Cited

OTHER PUBLICATIONS

Labome: "Product Summary for Cd3e Monoclonal Antibody (SPV-T3b)," Dec. 22, 2022, vol. 15, No. 48, 4 Pages, Retrieved from URL: https://www.labome.com/product/Invitrogen/07-0303.html.
Lee E.U., et al., "Alteration of Terminal Glycosylation Sequences on N-Linked Oligosaccharides of Chinese Hamster Ovary Cells by Expression of B-Galactoside α2,6-Sialytransferase," The Journal of Biological Chemistry, Aug. 15, 1989, vol. 264, No. 23, pp. 13848-13855.
Lee S-M., et al., "Cell to Cell Interaction Can Activate Membrane-bound APRIL Which Are Expressed on Inflammatory Macrophages," Immune Network, Oct. 2010, vol. 10, No. 5, pp. 173-180.
Lefranc M-P., et al., "IMGT, the International ImMunoGeneTics Database," Nucleic Acids Research, Oxford University Press, 2001, vol. 29, No. 1, pp. 207-209.
Liu., et al., "Method for Preparing Bispecific Monoclonal Antibodies," Chinese Animal Husbandry and Veterinary Medicine, vol. 34, pp. 49-52.
Liu Z., et al., "Asymmetrical FC Engineering Greatly Enhances Antibody-dependent Cellular Cytotoxicity (ADCC) Effector Function and Stability of the Modified Antibodies," Journal of Biological Chemistry, Feb. 7, 2014, vol. 289, No. 6, pp. 3571-3590.
Lloyd C., et al., "Modelling the Human Immune Response: Performance of a 1011 Human Antibody Repertoire Against a Broad Panel of Therapeutically Relevant Antigens," Protein Engineering, Design & Selection, 2009, vol. 22, No. 3, pp. 159-168.
Lokhorst H.M., et al., "Targeting CD38 with Daratumumab Monotherapy in Multiple Myeloma," The New England Journal of Medicine, 2015, vol. 373, No. 13, pp. 1207-1219, 5 Pages.
Lorentsen K., et al., "Uncoupling Tumor-cell Cytotoxicity From Cytokine Release With Novel T-cell Engaging Bispecific Antibodies," Meeting Info: American Association for Cancer Research Annual Meeting, Cancer Research, 2019, vol. 79, No. 13 (Suppl), Abstract 1554, 1 Page.
Mailankody S., et al., "T-Cell Engagers—Modern Immune-Based Therapies for Multiple Myeloma," The New England Journal of Medicine, Aug. 11, 2022, vol. 387, No. 6, pp. 558-561.
Milteniy Biotec: "Product Summary for Milteniy Biotec CD3 Antibodies Recombinant," [online], [Retrieved on Dec. 22, 2022] Retrieved from URL: https://www.miltenyibiotec.com/DE-en/products/cd3-antibodies-rea613.html#fitc:I-ml.
Min L., et al., "HBs/CD3 Bispecific Antibody Mediates The Cytotoxic Effect of LAK on HBV DNA-transfected Cells," Medical Journal of the People's Liberation Army, vol. 22, No. 6, pp. 397-399.
Moreau P., et al., "Teclistamab in Relapsed or Refractory Multiple Myeloma," The New England Journal of Medicine, Aug. 11, 2022, vol. 387, No. 6, pp. 495-505. Published on Jun. 5, 2022.
Morrison S.L., et al., "Chimeric Human Antibody Molecules: Mouse Antigen-binding Domains with Human Constant Region Domains," 1984, Proceedings of the National Academy of Sciences of the United States of America, vol. 81, pp. 6851-6855.
Opposition to European Patent No. EP 2780375 B1, Opponent 06: James Poole Limited, Experimental Report 1: Cytotoxic Activity, 6 Pages.
Opposition to European Patent No. EP2780375B1, Opponent 06: James Poole Limited, Experimental Report 2: Epitope Cluster Exchange and Alanine Scanning, 5 Pages.
Pelekanou V., et al., "Detection of the TNFSF Members Baff, April, Tweak and their Receptors in Normal Kidney and Renal Cell Carcinomas," Analytical Cellular Pathology, 2011, vol. 34, pp. 49-60, 13 Pages.
Pessano S., et al., "The T3/T cell Receptor Complex: Antigenic Distinction between the Two 20-kd T3 (T3-delta and T3-epsilon) Subunits," The EMBO Journal, 1985, vol. 4, No. 2, pp. 337-344.
Rabia L.A., et al., "Understanding and Overcoming Trade-offs Between Antibody Affinity, specificity, Stability and Solubility," Biochemical Engineering Journal, Sep. 15, 2018, vol. 137, pp. 365-374.
Rangaswamy U., et al., "A Next Generation Bispecific Antibody Platform for Effective Tumor Cell Killing With Minimal Cytokine Release," Journal for Immuno Therapy of Cancer, Meeting Info: 34th Annual Meeting and Pre-Conference Programs of the Society for Immunotherapy of Cancer, SITC 2019: Part 2, National Harbor, MD, United States, Nov. 10, 2019-Nov. 10, 2019, vol. 7, Supplement 1, Abstract No. P701, 01 Page.
Results of Structural Comparison Performed by Dr. Christine E. Tinberq in the EP Opposition for EP2780375, Cited on Feb. 24, 2023, 04 Pages.
Rudikoff S., et al., "Single Amino Acid Substitution Altering Antigen-Binding Specificity," Proceedings Of The National Academy Of Sciences (Part 1: Biological Sciences, Mar. 15, 1982), Mar. 1, 1982, vol. 79, No. 6, pp. 1979-1983, 6 Pages, DOI: 10.1073/PNAS.79.6.1979, ISSN 0027-8424, XP002683593.
Sandusky G.E., et al., "Use of Monoclonal Antibodies to Human Lymphocytes to Identify Lymphocyte Subsets in Lymph Nodes of the Rhesus Monkey and the Dog," The Journal of Medical Primatology, 1986, vol. 15, No. 6, pp. 441-451.
Sequence Alignment of BCMA (TNFRSF17) Amino Acids 24-41 ("Epitope Cluster 3") from Different Species, cited on Apr. 17, 2023 in the EP Opposition for EP2780375, 3 Pages.
Sequence Alignment of CD3 Epsilon; Crab-eating Macaque, Rhesus Macaque, cited on Jun. 12, 2020 in the EP Opposition for EP2780375, 1 page.
Sequence Alignment of the 27 N-Terminal Amino Acids of the CD3 Epsilon Chain of Humans, Crab-Eating Macaque and Rhesus Macaque, 1 Page.
Sequence Comparison, cited on May 18, 2021, in the EP Opposition for EP2780375, 4 Pages.
Sequence Comparison of WO2008/011956 and EP 2780375B1, 4 Pages.
Singer M., et al., "Genes and Genomes A Changing Perspective," Moscow, Mir, 1991, 1:63-64, 17 Pages.
SINOBIOLOGICAL: "Rabbit Monoclonal Recombinant Anti-CD3D CD3E Heterodimer Antibody," China, Jul. 7, 2016, 2 Pages, Cat. No: CT026-R301, XP055574141, [Retrieved on Jul. 5, 2022] Retrieved from URL: https://www.sinobiological.com/antibodies/human-cynomolgus-cd3d-cd3e-ct026-r301.
Soares A., et al., "Transient Global T Cell Activation After Vaccination of Rhesus Macaques with a DNA-Poxvirus Vaccine Regimen for HIV," Vaccine, 2015, vol. 33, Issue 30, pp. 3435-3439, 7 Pages.
Sun L.L., et al., "Anti-CD20/CD3 T Cell-Dependent Bispecific Antibody for the Treatment of B Cell Malignancies," Science Translational Medicine, May 13, 2015, vol. 7, No. 287, 287ra70-287ra70, 12 Pages.
Supporting Evidence in EP Opposition No. 2780375 for EP Application No. 12805432.7, Regarding Availability of Kontermann, Bispecific Antibodies, Springer-Verlag Berlin Heidelberg, 2011, 3 Pages.
Turley D.M., "Prospects for Antigen-Specific Tolerance Based Therapies for the Treatment of Multiple Sclerosis," Results and Problems in Cell Differentiation, vol. 51, pp. 217-235, doi: 10.1007/400_2008_13, XP009174523.
Ueda O., et al., "Entire CD3ϵ, δ, and μ Humanized Mouse to Evaluate Human CD3-Mediated Therapeutics," Scientific Reports, Apr. 3, 2017, vol. 7, No. 45839, 16 Pages, DOI: 10.1038/srep45839.
Velasquez MP, et al., "Redirecting T cells to hematological malignancies with bispecific antibodies," Blood. Jan. 4, 2018;131(1):30-38.
Vu M.D., et al., "A New Class of T-cell Bispecific Antibodies for the Treatment of Multiple Myeloma, Binding to B Cell Maturation Antigen and Cd3 and Showing Potent, Specific Antitumor Activity in Myeloma Cells and Long Duration of Action in Cynomolgus Monkeys," Blood, Dec. 3, 2015, vol. 126, No. 23, p. 2998, 03 pages, DOI: 10.1182/blood. V126.23.2998.2998, XP086650811.
Wang D.D., et al., "Fixed Dosing Versus Body Size-Based Dosing of Monoclonal Antibodies in Adult Clinical Trials," Journal of Clinical Pharmacology, Jul. 20, 2009, vol. 49, No. 9, pp. 1012-1024, 13 Pages.
Wang Z., et al., "Biomarkers of Cytokine Release Syndrome and Neurotoxicity Related to CAR-T Cell Therapy," Biomarkers Research, Jan. 22, 2018, vol. 6, No. 4, 10 pages.
Winter, et al., "Humanized Antibodies," Immunology Today, 1993, vol. 14, No. 5, pp. 139-143.

(56) References Cited

OTHER PUBLICATIONS

Winter G., et al., "Humanized Antibodies," Immunology Today, 1993, vol. 14, No. 6, pp. 243-236.
Wu S., et al., "CD38-Expressing Macrophages Drive Age-Related NAD+ Decline," Nature Metabolism, Nov. 2020, vol. 2, pp. 1186-1187.
Xin L., "Screening, Preparation and Identification of Single Domain Antibodies Specific for B Cell Maturation Antigen," Retrieved from the Internet: URL: https://www.ixueshu.com/h5/document/994906362d7885de7ab8eba7cacf409d318947a18e7f9386.html, 10 pages.
"Antibody Therapeutics—Teneobio's Next Generation of Multispecific Antibody Therapeutics," Jan./Feb. 2018, [retrieved on Mar. 21, 2023]. Retrieved from Internet: <URL: https://drug-dev.com/antibody-therapeutics-teneobios-next-generation-of-multispecific-antibody-therapeutics/>.
Adams et al., "Prolonged in Vivo Tumour Retention of a Human Diabody Targeting the Extracellular Domain of Human HER2Ineu," (1998) British Journal of Cancer 77(9):1405- 1412.
Alderson et al., "CAT-8015: A Second-Generation Pseudomonas Exotoxin A-Based Immunotherapy Targeting CD22-Expressing Hematologic Malignancies," (2009) Clinical Cancer Research 15(3):832-839.
Ali et al., "T cells expressing an anti-B-cell maturation antigen chimeric antigen receptor cause remissions of multiple myeloma," (2016) Blood 128(13):1688-1700.
Almagro "Identification of differences in the specificity-determining residues of antibodies that recognize antigens of different size: implications for the rational design of antibody repertoires," (2004) Journal of Molecular Recognition 17(2):132-143.
Anonymous, "Flow Cytometry Antibody: CD3e Cat. No. CT026-R301, SinoBiological Inc., —Antibody-Catalogue, "Anonymous, "Flow Cytometry Antibody: CD3e Cat. No. CT026-R301, SinoBiological Inc,—Antibody-Catalogue," (2017). Retrieved from Internet: < URL: http://www.sinbiologica.com/flow-symmetry-antibody-elite.html> [Inactive Link].
Armitage, "A Clinical Evaluation of the International Lymphoma Study Group Classification of Non-Hodgkin's Lymphoma," (1997) Blood, vol. 89(11):3909-3918.
Armour et al., "Recombinant human lgG molecules lacking Fey receptor I binding and monocyte triggering activities," (1999) Eur J Immunol. 29(8):2613-2624.
Arnett et al., "Crystal Structure of a Human CD3-epsilon/delta Dimer in Complex with a UCHT1 Single-chain Antibody Fragment," (2004) Proc Natl Acad Sci USA 101(46):16268- 16273.
Baas et al., "Superhuman Mice" (2014) Science-Business exchange 7(17):1-2.
Baeuerle et al., "Bispecific T-cell engaging antibodies for cancer therapy," (2009) Cancer Research 69(12):4941-4944.
Baeuerle et al., "BiTE: A new class of antibodies that recruit T-cells," (2008) Drugs of the Future 33(2):137-147.
Baeuerle et al., "BiTE: Teaching antibodies to engage T-cells for cancer therapy," (2009) Current Opinion in Molecular Therapeutics 11(1):22-30.
Banihashemi et al., "Development of Specific Nanobodies (VHH) for CD19 Immuno-targeting of Human B-lymphocytes," (2018) Iranian Journal of Basic Medical Sciences 21(5):455-464.
Bargou et al., "Tumor Regression in Cancer Patients by Very Low Doses of a T Cell-Engaging Antibody," (2008) Science 321:974-977.
BCMA (Vicky-1): ALX-804-151 product datasheet, Enzo Life Sciences, last revised Dec. 20, 2019.
BCMA (Vicky-1): sc-57037 datasheet, Santa Cruz Biotechnology, https://datasheets.scbt.com/sc-57037.pdf (last visited Apr. 12, 2022).
Bellucci et al., "Complete response to donor lymphocyte infusion in multiple myeloma is associated with antibody responses to highly expressed antigens," (2004) Blood 103(2):656-663.
Bellucci et al., "Complete response to donor lymphocyte infusion in patients with multiple myeloma is associated with antibody response to BCMA, a plasma cell membrane receptor" (2003) Blood 102(11):192a-193a.
Bellucci et al., "Graft-versus-tumor response in patients with multiple myeloma is associated with antibody response to BCMA, a plasma-cell membrane receptor," (2005) Blood 105(10):3945-3950.
Bluemel et al., "Epitope Distance to the Target Cell Membrane and Antigen Size Determine the Potency of T Cell-mediated Lysis by BiTE Antibodies Specific for a Large Melanoma Surface Antigen," (2010) Cancer Immunol Immunother 59:1197-1209.
Bodmer et al., "Review—The molecular architecture of the TNF superfamily," (2002) Trends in Biochemical Sciences 27(1):19-26.
Boesch et al., "Highly parallel characterization of lgG Fc binding interactions," (2014) MAbs 6(4):915-927.
Borchmann et al., "Phase 1 trial of the Novel Bispecific Molecule H22xKi-4 in Patients with Refractory Hodgkin Lymphoma," (2002) Blood 100(9):3101-3107.
Bossen et al., "Review, BAFF, APRIL and their receptors: Structure, function and signaling," (2006) Seminars in Immunology 18:263-275.
Brudno et al., "T Cells Genetically Modified to Express an Anti-B-Cell Maturation Antigen Chimeric Antigen Receptor Cause Remissions of Poor-Prognosis Relapsed Multiple Myeloma," (2018) J Clin Oncol 36(22):2267-2280.
Bruggemann et al., "Human Antibody Production in Transgenic Animals," (2014) Archivum Immunologiae et Therapie Experimentalis, Birkahaeser Verlag AG 63(2):101-108.
Brüggemann et al., "Heavy-Chain-Only Antibody Expression and B-Cell Development in the Mouse," (2006) Crit. Rev. Immunol. 26(5):377-390.
Buelow et al., "Development of a fully human T cell engaging bispecfic antibody for the treatment of multiple myeloma," (2017) J Clin OnCol vol. 35 Supplement.
Buelow et al., "TNB3838.0001: A Multicenter, Phase 1, Open-Label, Dose-Escalation Andexpansion Study of TNB-3838, a Bispecific Antibodytargeting BCMA in Subjects with Relapsed or Refractorymultiple Myeloma," (2019) Blood 134(Supplement 1):1874.
Business Wire: "OMT Therapeutics Announces UniRat TM Alliance with Caltech," May 15, 2015, [Retrieved on May 6, 2020]. Retrieved from the Internet: <URL: https://www.businesswire.com/news/home/20150514006523/en/OMT%20-Therapeutics-Announces-UniRat%20TM%20-%20Alliance-Caltech>.
Canfield et al"The Binding Affinity of Human IgG for its High Affinity Fc Receptor Is Determined by Multiple Amino Acids in the CH2 Domain and Is Modulated by the Hinge Region," J. Exp. Med. 173:1483-1491.
Caraccio et al., "Bispecific Antibodies for Multiple Myeloma: A Review of Targets, Drugs, Clinical Trials and Future Directions," (2020) Frontiers in Immunology 11(50):1-25.
Carpenter et al., "B-cell Maturation Antigen Is a Promising Target for Adoptive T-cell Therapy of Multiple Myeloma," (2013) Clin Cancer Res 19(8):2048-2060.
Chames et al., "Bispecific antibodies for cancer therapy," (2009) Current Opinion in Drug Discovery & Development 12(2):276-283.
Chames et al., "Bispecific antibodies for cancer therapy," (2009) mAbs 1(6):539-547.
Chassaing et al., "Dextran Sulfate Sodium (DSS)-Inducted Colitis in Mice," (2014) Current Protocols in Immunology 15(25):1-14.
Chen et al., "Fusion protein linkers: Property, design and functionality," (2013) Advanced Drug Delivery Reviews 65(10): 1357-1369.
Chini et al., "The Pharmacology of CD38/NADase: An Emerging Target in Cancer and Diseases of Aging," (2018) Trends in Pharmacological Sciences 39(4):424-436.
Chiu et al., "Engineering antibody therapeutics," (2016) Current Opinion in Structural Biology 38:163-173.
Chiu et al., "Hodgkin lymphoma cells express TACI and BCMA receptors and generate survival and proliferation signals in response to BAFF and APRIL," (2007) Blood 109(2):729-739.
Choi et al., "Bispecific antibodies engage T-cells for antitumor Immunotherapy, " (2011) Expert Opinion on Biological Therapy 11(7):843-853.

(56) References Cited

OTHER PUBLICATIONS

Chothia et al., "Canonical structures for the hypervariable regions of immunoglobulins," (1987) Journal of Molecular Biology 196(4):901-917.
Chothia et al., "Conformations of immunoglobulin hypervariable regions," (1989) Nature 342:877-883.
Chou et al., "Quantitative Analysis of Dose-Effect Relationships: The Combined Effects of Multiple Drugs or Enzyme Inhibitors," (1984) Hopkins University School of Medicine 22:27-55.
Christian et al., "Measuring Bacterial Ectoenzyme Activities in Marine Waters Using Mercuric Chloride as a Preservative and Control," (1995) Marine Ecology Progress Series 123:217-224.
Clayton et al., "CD3nand CD3 are alternatively spliced products of a common genetic locus and are transcriptionally and/or post-transcriptionally regulated during T-cell development," (1991) Proceedings of the National Academy of Sciences USA 88:5202-5206.
ClinicalTrials.gov, "Study NCT03090659, LCAR-B38M-02 Cells in Treating Relapsed/Refractory (R/R) Multiple Myeloma (LEGEND-2)", Mar. 20, 2017, [retrieved on Sep. 20, 2019], (v1), ID: NCT03090659. Retrieved from the Internet: <URL: <https://clinicaltrials.gov/ct2/history/NCT03090659?V_1=View#StudyPageTop>.
Clynes et al., "Fc Receptors are Required in Passie and Active Immunity to Melanoma," (1998) PNAS (USA) 95(2):652-656.
Concepcion et al., "Label-Free Detection of Biomolecular Interactions Using Biolayer Interferometry for Kinetic Characterization," (2009) Combinatorial Chemistry & High Throughput Screening 12(8):791-800.
Crescioli et al., "lgG4 Characteristics and Functions in Cancer Immunity," (2016) Curr Allergy Asthma Rep 16:1-11.
Cui et al., "Targeted Integration in Rat and Mouse Embryos with Zinc-finger Nucleases," (2011) Nature Biotechnology 29(1):64-67.
Dai et al., "Chimeric Antigen Receptors Modified T-Cells for Cancer Therapy," (2016) J Natl Cancer Inst 108(7):dvj439.
Dasilva, "Abstract 345:A Met x MET Bispecific Antibody that Induces Receptor Degradation Potently Inhibits the Growth of MET-addicted Tumor Xenografts," (2017) AACR Annual Meeting 1-2.
Declaration Nathan D. Trinklein, Ph.D. in EP 2780375 Opposition, EP Application No. 12805432.7.
Declaration of Dr. Rui Zhu, PhD, dated Jun. 9, 2020 in EP 2780375 Opposition, EP Application No. 12805432.7.
Declaration of Kara Olson, dated May 14, 2021 in EP 2780375 Opposition, EP Application No. 12805432.7.
Declaration of Kevin C. Lindquist in EP 2780375 Opposition, EP Application No. 12805432.7.
Desmyter et al., "Antigen Specificity and High Affinity Binding Provided by One Single Loop of a Camel Single-domain Antibody," (2001) Journal of Biological Chemistry, American Society for Biochemistry and Molecular Biology 276(28) :26285-26290.
DiLillo et al., "A BCMAxCD3 Bispecifi T Cell-engaging Antibody Demontstrates Robust Antitumor Efficacy Similar to that of Anti-BCMA CAR T Cells," (2020) Blood Advances 5(5): 1291-1304.
Dillon et al., "An APRIL to remember: Novel TNF ligands as therapeutic targets," (2006) Nat Rev 5:235-246.
Dimopoulos et al., "Daratumumab, Lenalidomide, and Dexamethasone for Multiple Myeloma," (2016) New England Journal of Medicine 375(14):1319-1331.
Dondelinger et al., "Understanding the Significance and Implications of Antibody Numbering and Antigen-binding Surface/Residue Definition," (2018) Frontiers in Immunology 9:1-15.
Dooley et al., "Selection and Characterization of Naturally Occurring Single-domain (IgNAR) Antibody Fragments from Immunized Sharks by Phage Display," (2003) Molecular Immunology 40(1):25-33.
Duncan et al., "Localization of the binding site for the human high-affinity Fc receptor on lgG ," (1988) Nature 332:563-564.
Durben et al., "Characterization of a Bispecific FLT3 X CD3 Antibody in an Improved, Recombinant Format for the Treatment of Leukemia," (2015) Molecular Therapy 23(4):648-655.
Excerpt of examination report from EP Application No. 12805432.7, dated Oct. 31, 2016, p. 1.
Figure 6.8 of Antigen receptor structure and signaling pathways, Immunobiology: The Immune System in Health and Disease. 5th Edition, Janeway CA Jr, Travers P, Walport M, et al., New York: Garland Science; 2001.
Fitzgerald et al., "The Cytokine FactsBook," 2nd ed. (2001) Academic Press, pp. 151-152.
Force Aldred et al., "Meeting Info: 2018 ASCO-SITC Clinical Immuno-Oncology Symposium, Multispecific Antibodies Targeting CD38 Show Potent Tumor-specific Cytoxicity," (2018) Journal of Clinical Oncology Abstract 36(5):60.
Force Aldred et al., "Winning the Numbers Game: Novel Multi-specific Therapeutics from a Diverse Collection of Human Domain Antibodies," Oct. 10, 2016, [Retrieved on May 6, 2020]. Retrieved from the Internet: <URL: https://2019.lakepharma.com/files/symposiums/Winning%20the%20Numbers%20Game%20-%20Novel%20Multi-specific%20Therapeutics%20from%20a%20Diverse%20Collection%20of%20Human%20Dom ain%20Antibodies%20-%20Shelley%20Force%20Aldred.pdf> [Inactive Link].
Frenken et al., "Isolation of Antigen Specific Llama VHH Antibody Fragments and Their High Level Secretion by *Saccharomyces* Cerevisiae," (2000) J. Biotechnol. 78:11-21.
Fry et al., "CD22-targeted CAR T Cells Induce Remission in B-ALL that is Naïve or Resistant to CD19-targeted CAR Immunotherapy," (2018) Nature Medicine 24(1):20-28.
Gazzano-Santoro et al., "A non-radioactive complement-dependent cytotoxicity assay for anti- CD20 monoclonal antibody," (1996) Journal of Immunological Methods 202(2):163-171.
GenBank Accession No. AB052772.1, "Homo sapiens gene for BCMA, complete cds," available at https://www.ncbi.nlm.nih.gov/nuccore/AB052772 (last visited Apr. 23, 2020).
GenBank Accession No. NM_000733, "Homo sapiens CD3e molecule (CD3E), mRNA", available at https://www.ncbi.nlm.nih.gov/nuccore/NM_000733.3 (last visited Apr. 23, 2020).
Gershoni et al., "Epitope Mapping—The First Step in Developing Epitope-based Vaccines," (2007) Biodrugs, Adis International, Ltd. NZ 21(3):145-156.
Geurts et al., "Knockout Rats via Embryo Microinjection of Zinc-Finger Nucleases," (2009) Science 325(5939):433.
Ghahroudi et al., "Selection and Identification of Single Domain Antibody Fragments from Camel Heavy-chain Antibodies," (1997) FEBS Lett. 414:521-526.
Giavridis et al., "CAR T cell-induced cytokine release syndrome is mediated by macrophages and abated by IL-1 blockade," (2018) Nature Medicine 24:731-738.
Glennie et al., "Preparation and Performance of Bispecific F(ab' gamma)2 Antibody Containing Thioether-linked Fab' gamma Fragments," (1987) Journal of Immunology 139(7):2367-2375.
Gras et al., "BCMAp: an integral membrane protein in the Golgi apparatus of human mature B lymphocytes," (1995) International Immunology 7(7):1093-1106.
Gruss et al., "Structural and Biological Features of the TNF Receptor and TNF Ligand Superfamilies: Interactive Signals in the Pathobiology of Hodgkin's Disease," (1996) Ann Oncol, 7 (Suppl 4):19-26.
Gupta et al., "Constitutive Inflammatory Cytokine Storm: A Major Threat to Human Health," (2019) Journal of Interferon & Cytokine Research 40(1):19-23.
Gust et al., "Endothelial Activation and Blood-Brain Barrier Disruption in Neurotoxicity after Adoptive Immunotherapy with CD19 CAR-T Cells," (2017) Cancer Discovery 7(12):1405-1419.
Guy et al., "Organization of Proximal Signal at the TCR:CD3 Complex," (2009) Immunol Rev 232(1):1-22.
Haffner et al., "Discovery, Synthesis and Biological Evaluation of Thiazoloquin(az)olin(one)es as Potent CD38 Inhibitors," (2015) Journal of Medical Chemistry 58:3548-3571.
Hamers-Casterman et al., "Naturally Occurring Antibodies Devoid of Light Chains," (1993) Nature 363:446-448.
Hamilton et al., "Humanization of Yeast to Produce Complex Terminally Sialylated Glycoproteins," (2006) Science 313(5792):1441-1443.

(56) References Cited

OTHER PUBLICATIONS

Hanes et al., "New advances in microsphere-based single-dose vaccines," (1997) Advanced Drug Delivery Reviews 28(1):97-119.
Hermans et al., "The VITAL assay: a versatile fluorometric technique for assessing CTL- and NKT-mediated cytotoxicity against multiple targets in vitro and in vivo," (2004) Journal of Immunological Methods 285(1):25-40.
Hipp et al., "A novel BCMA/CD3 bispecific T-cell engager for the treatment of multiple myeloma induces selective lysis in vitro and in vivo," (2017) Leukemia 31:1743-1751.
Hlavacek et al., "Steric Effects on Multivalent Ligand-Receptor Binding: Exclusion of Ligand Sites by Bound Cell Surface Receptors," (1999) Biophysical Journal 76(6):3031-3043.
Honegger, "Yet Another numbering scheme for immunoglobulin variable domains: an automatic modeling and analysis tool," (2001) Journal of Molecular Biology 309(3):657-670.
Honemann et al., "A Novel Recombinant Bispecific Single-chain Antibody, bscWue-1 x CD3, Induces T-cell-mediated Cytotoxicity Towards Human Multiple Myeloma Cells," (2004) Leukemia 15:636-644.
Hotzel et al., "A strategy for risk mitigation of antibodies with fast clearance," (2012) mABs 4(6)753-760.
Hymowitz et al., "Structures of APRIL-Receptor Complexes," (2005) Journal of Biological Chemistry 280(8):7218-7227.
International Search Report and Written Opinion for PCT Application No. PCT/US2021/039961.
International Search Report and Written Opinion, mailed Oct. 11, 2018, in PCT Application No. PCT/US2018/039917.
Iri-Sofla et al., "Nanobody-based chimeric receptor gene integration in Jurkat cells mediated by PhiC31 integrase," (2011) Experimental Cell Research 317(18):2630-2641.
Jabbour et al., "Monoclonal Antibodies in Acute Lymphoblastic Leukemia," (2015) Blood 125(26):2010-2016.
Jackson et al., "Driving CAR T-cells forward," (2016) Nature Reviews Clinical Oncology 13(6):370-383.
Jamnani et al., "T Cells Expressing VHH-directed Oligoclonal Chimeric HER2 Antigen Receptors: Towards Tumor-directed Oligoclonal T Cell Therapy," (2014) Biochimica et Biophysica Acta 1840:378-386.
Janssens et al., "Generation of Heavy-chain-only Antibodies in Mice," (2006) Proceedings of the National Academy of Sciences of the USA 103(41):15130-15135.
Jaton et al., "Recovery of antibody activity on reoxidation of completely reduced polyalanyl heavy chain and its Fd fragment derived from anti-2,4-dinitrophenyl antibody," (1968) Biochemistry 7(12):4185-4195.
Jemal et al., "Cancer Statistics, 2008," ACS Journals (2008) 58(2):71-96.
Jones, "Analysis of Polypeptides and Proteins," (1993) Advanced Drug Delivery 10(1):29-90.
Kalled et al., "The role of BAFF in immune function and implications for autoimmunity," (2005) Immunol Rev 204:43-54.
Kanda et al., "Establishment of a GDP-mannose 4,6-dehydratase (GMD) knockout host cell line: A new strategy for generating completely non-fucosylated recombinant therapeutics," (2007) Journal of Biotechnology 139:300-310.
Kaneko et al., "Anti-inflammatory Activity of Immunoglobulin G Resulting from Fc Sialylation," (2006) Science 313(5787)670-673.
Kapoor et al., "Anti-CD20 Monoclonal Antibody Therapy in Multiple Myeloma," (2008) Br J Haematol 141(2):135-148.
Kim et al., "Mutational approaches to improve the biophysical properties of human single-domain antibodies", (2014) Biochimica Et Biophysica ACTA (BBA)—Proteins & Proteomics, Elseviern Netherlands (2014) 1844(11):1983-2001.
Kjer-Nielsen et al., "Crystal Structure of the Human T Cell Receptor CD3 Eγ Heterodimer Complexed to the Therapeutic mAb OKT3," (2004) Proceedings of the National Academy of Sciences 101:7675-7680.
Koarada et al., "Autoantibody-Producing RP105 B Cells, from Patients with Systematic Lupus Erythematosus, showed more Preferential Expression of BCMA Compared with BAFF-R than Normal Subject," (2010) Rheumatology 49:662-670.
Kochenderfer et al., "Construction and preclinical evaluation of an anti-CD19 chimeric antigen receptor," (2009) J Immunother 32(7):689-702.
Kohler et al., "Continuous cultures of fused cells secreting antibody of predefined specificity," (1975) Nature 256:495-497.
Kontermann "Bispecific Antibodies" (2011), Springer-Verlag Berlin Heidelberg, Chapters 1, 2, 7, 11, 13, 14 and 15.
Kontermann, "Invited review—Recombinant bispecific antibodies for cancer therapy," (2005) Acta Pharmacologica Sinica 26(1):1-9.
Kufer et al., "Review—A revival of bispecific antibodies," (2004) Trends in Biotechnology 22(5):238-244.
Kuhns et al., "Deconstructing the Form and Function of the RCR/CD3 Complex," (2006) Immunity 24:133-139.
Kumar et al., "Improved survival in multiple myeloma and the impact of novel therapies," (2008) Blood 111(5):2516-2520.
Kumar et al., "International Myeloma Working Group consensus criteria for response and minimal residual disease assessment in multiple myeloma," (2016) The Lancet Oncology 17(8):e328-e346.
Laabi et al., "A new gene, BCM, on chromosome 16 is fused to the interleukin 2 gene by a t(4;16)(q26;p13) trans location in a malignant T cell lymphoma," (1992) EMBO J 11(11):3897-3904.
Laabi et al., "The BCMA gene, preferentially expressed during B lymphoid maturation, is bidirectionally transcribed," (1994) Nucleic Acids Res 22(7):1147-1154.
Labrijn et al., "Bispecific Antibodies: A Mechanistic Review of the Pipeline," (2019) Nature Reviews Drug Discovery 18(8):585-608.
Labrijn et al., "Therapeutic lgG4 antibodies engage in Fab-arm exchange with endogenous human lgG4 in vivo," (2009) Nature Biotechnology 27(8):767-771.
Langer, "New Methods of Drug Delivery," (1990) Science 249(4976):1527-1533.
Lefranc et al., "The Immunoglobulin FactsBook," (2001) Academic Press, FactsBook Series pp. 1-240.
Leiba et al., "Activation of B cell maturation antigen (BCMA) on human multiple myeloma cells by a proliferation-inducing ligand (APRIL) promotes myeloma cell function in the bone marrow microenvironment," (2007) Blood 110(11):1503.
Levine, "Mechanisms of Soluble Cytokine Generation," (2004) J Immunol 173(9):5343-8.
Lindhofer et al., "Preferential Species-restricted Heavy/Light Chain Pairing in Rat/Mouse Quadromas. Implications for a Single-step Purification of Bispecific Antibodies," (1995) The Journal of Immunology 155(1):219-225.
Link et al., "Anti-CD3-Based Bispecific Antibody Designed for Therapy of Human B-Cell Malignancy can Induce T-cell Activation by Antigen-dependent and Antigen-independent Mechanisms," (1998) Int J Cancer 77(2):251-256.
Liu et al., "Ligand-receptor binding revealed by the TNF family member TALL-1," (2003) Nature 423:49-56.
Lund et al., "Expression and characterization of truncated forms of humanized L243 IgGI," (2000) European Journal of Biochemistry 267(24):7246-7256.
MAB193 data sheet, Human BCMA/TNFRSF17 Antibody, R&D Systems, last revised Feb. 7, 2018.
Mack et al., "A Small Bispecific Antibody Construct Expressed as a Functional Single-chain Molecule with High Tumor Cell Cytotoxicity," (1995) PNAS 92(15):7021-7025.
Mackay et al., "BAFF and APRIL: a tutorial on B cell survival," (2003) Annu Rev Immunol 21:231-264.
Malik et al., "A Novel Fully Human Bispecific CD19 x CD3 Antibody that Kills Lymphoma Cells with Minimal Cytokine Secretion," (2018) 132(1):1671.
Mariuzza et al., "The Structural Basis of Antigen-antibody Recognition," (1987) Ann Rev Biophys, Biophys Chem 16:139-159.
Martinez-Cingolani et al., "Development of Chimeric Antigen Receptors for Multiple Myeloma," (2016) Biochem Soc Trans 44(2):397-444.
Menoret et al., "Characterization of Immunoglobulin Heavy Chain Knockout Rats," (2010) European Journal Immunology 40:2932-2941.

(56) References Cited

OTHER PUBLICATIONS

Menoret et al., "Transgenic Animals and Genetic Engineering Techniques," (2015) Transgenic Res 24:1079-1085.
Merchant al., "An Efficient Route to Human Bispecific lgG," (1998) Nature Biotechnology, Gale Group, Inc. 16(7):677-681.
Mikkilineni et al., "Chimeric antigen receptor T-cell therapies for multiple myeloma," (2017) Blood 130(24):2594-2602.
Miller et al., "Design, Construction, and In Vitro Analyses of Multivalent Antibodies," (2003) Journal of Immunology 170(9):4854-4861.
Moreaux et al., "APRIL and TACI interact with syndecan-1 on the surface of multiple myeloma cells to form an essential survival loop, " (2009) Eur J Heamatol 83:119-129.
Moreaux et al., "BAFF and APRIL protect myeloma cells from apoptosis induced by interleukin 6 deprivation and dexamethasone," (2004) Blood 103(8):3148-3157.
Müller et al., "Bispecific antibodies for cancer immunotherapy," (2010) Biodrugs 24(2):89-98.
Muller et al., "Recombinant bispecific antibodies for cellular cancer immunotherapy," (2006) Current Opinion in Molecular Therapeutics 9(4):319-326.
Muyldermans, "Single domain camel antibodies: current status," 2001; Journal of Biotechnology 74(4):277-302.
Naddafi et al., "Anti-CD19 Monoclonal Antibodies: A New Approach to Lymphoma Therapy," (2015) IJMCM 4(3):143-151.
Neisig et al., "Assembly of the T-Cell Antigen Receptor," (1993) Journal of Immunology 151:870-879.
Neri et al., "Neutralizing B-cell activating factor antibody improves survival and inhibits osteoclastogenesis in a severe combined immunodeficient human multiple myeloma model" (2007) Clin Cancer Res 13(19):5903-5909.
Ng et al., "B cell-activating factor belonging to the TNF family (BAFF)-R is the principal BAFF receptor facilitating BAFF costimulation of circulating T and B cells," (2004) J Immunol 173(2):807-817.
Nguyen et al., "Functional Heavy-Chain Antibodies in Camelidae," (2001) Advances in Immunology 79:261-296.
Nguyen et al., "Heavy-chain Only Antibodies Derived from Dromedary are Secreted and Displayed by Mouse B Cells," (2003) Immunology 109(1):93-101.
Nishimoto et al., "Adoptive Therapy with Cord Blood T Reglatory Cells Enhances Anti-myeloma Efficacy of T Cell Based Immunotherapies," (2020) Blood 136(Suppl); 26-27.
Norelli et al., "Monocyte-derived IL-1 and IL-6 are differentially required for cytokine-release syndrome and neurotoxicity due to CAR T cells," (2018) Nature Medicine24:739-748.
Novak et al., "Expression of BCMA, TACI, and BAFF-R in multiple myeloma: a mechanism for growth and survival," (2004) Blood 103(2):689-694.
Nuttall et al., "Isolation and Characterization of an IgNAR Variable Domain Specific for the Human Mitochondrial Translocase Receptor Tom70," (2003) Eur. J. Biochem. 270:3543-3554.
Nuttall et al., "Selection and Affinity Maturation of IgNAR Variable Domains Targeting Plasmodium Falciparum AMA1," (2004) Function and Bioinformatics 55:187-197.
O'Connor et al., "BCMA Is Essential for the Survival of Long-lived Bone Marrow Plasma Cells," (2004) J Exp Medicine 199(1):91-97.
Ofran et al. "Automated identification of complementarity determining regions (CDRs) reveals peculiar characteristics of CDRs and B-cell epitopes," (2008) Journal of Immunology 181(9):6230-6235.
Omniab: Naturally Optimized Human Antibodies (2016), [Retrieved on May 6, 2020]. Retrieved from the Internet: <URL: http://content.stockpr.com/omniab/db/252/746/file/OmniAb.pdf>.
Padlan et al. "Identification of specificity-determining residues in antibodies." Faseb J. 1995;9:133-139.
Palumbo et al., "Daratumumab, Bortezomib, and Dexamethasone for Multiple Myeloma," (2016) New England Journal of Medicine 375(8):754-766.
Panowski et al., "Preclinical efficacy and safety comparison of CD3 bispecific and ADC modalities targeting BCMA for the treatment of multiple myeloma," (2019) AACR OF1-OF13.
Patel et al., "Engineering an APRIL-specific B Cell Maturation Antigen," (2004) Journal of Biological Chemistry 279(16):16727-16735.
Patentee's Response to EP Communication under Article 94(3), dated May 10, 2017 in EP Application No. 12805432.7.
Patentee's Response to EP Communication under Article 94(3), dated Apr. 13, 2016 in EP Application No. 12805432.7.
Pelekanou et al., "Expression of TNF-superfamily members BAFF and APRIL in Breast Cancer: Immunohistochemical Study in 52 Invasive Ductal Breast Carcinomas," (2008) BMC Cancer 8(76):1-9.
Pick et al., "Daratumumab resistance is frequent in advanced-stage multiple myeloma patients irrespective of CD38 expression and is related to dismal prognosis," (2018) European Journal of Haematology 100(5):494-501.
Pluckthun et al., "New protein engineering approaches to multivalent and bispecific antibody fragments," (1997) Immunology 3(2):83-105.
Presta et al., "Generation of Humanized, High Affinity Anti-tissue Factor Antibody Use as a Novel Antithrombotic Therapeutic," (2001) Thromb Haemost 85:379-389.
Presta et al., "Humanization of an Antibody Directed Against IgE," (1993) Journal of Immunology 151:2623-2632.
Proprietor's Remarks in Response to Office Action dated Dec. 16, 2014 in U.S. Pat. No. 9340621.
Proprietor's Remarks in Response to Office Action dated Jun. 19, 2014 in U.S. Pat. No. 9150664.
Pulte et al., "CD39 Expression on T Lymphocytes Correlates with Severity of Disease in Patients with Chronic Lymphocytic Leukemia," (2011) Clinical Lymphoma, Myeloma & Leukemia 11(4):367-372.
Pulte et al., "Improvement in Survival of Older Adults with Multiple Myeloma: Results of an Updated Period Analysis of SEER Data," (2011) The Oncologist 16(11):1600-1603.
Qin et al., "Paralleled comparison of vectors for the generation of CAR-T cells," (2016) Anti-Cancer Drugs 27(8):711-722.
Raab et al., "Multiple myeloma," (2009) Lancet 374:324-329.
Raje et al., "Anti-BCMA CAR T-Cell Therapy bb2121 in Relapsed or Refractory Multiple Myeloma," (2019) N Engl J Med 380(18):1726-1737.
Rangaswamy et al., "A Novel T-cell Bispecific Antibody Platform for Efficient T-cell Mediated Killing of Tumor Cells with Minimal Cytokine Oncology," (2018) Journal of Clinical Oncology 36(5) Supplement.
Ravetch et al., "Fc Receptors ," (1991), Annual Review of Immunology 9:457-192.
Reichert et al., "Development Trends for Monoclonal Antibody Cancer Therapeutics," (2007) Nat Rev Drug Discov 6(5):349-356.
Rennert et al., "A Soluble Form of B Cell Maturation Antigen, a Receptor for the Tumor Necrosis Factor Family Member APRIL, Inhibits Tumor Cell Growth," (2000) J. Exp. Med. 192(11):1677-1683.
Revets et al., "Nanobodies as novel agents for cancer therapy," (2005) Expert Opin Biol Ther 5(1):111-124.
Ridgway et al., "'Knobs-into-holes' Engineering of Antibody CH3 Domains for Heavy Chain Heterodimerization," (1996) Protein Engineering 9(7):617-621.
Rodriguez et al., "Initial Resulst of a Phase I Study of TNB-383B, a BCMA x CD3 Bispecific T-Cell Redirecting Antibody, in Relapsed/Refracotry Multiple Myeloma," (2020) Blood 136 (Supp 1):43-44.
Rodriguez et al., "Paper: Initial Results of a Phase 1 Study of TNB-383B, a BCMA x CD3 Bispecific T-cell Redirecting Antibody in Relapsed/Refractory Multiple Myeloma," (2020) Retrieved from Internet: <URL: https//ash.confex.com/ash/2020/webprogram/Paper139893.html>.
Roit, Immunology. Translated from English, Moscow: Mir; 2000.
Rossi et al., "Redirected T-cell Killing of Solid Cancers Targeted with an Anti-CD3/Trop-2-Bispecific Antibody is Enhanced in Combination with Interferon-g," 2014 Molecular Cancer Therapeutics 13(10):2341-2351.

(56) References Cited

OTHER PUBLICATIONS

Rouet et al., "Fully Human VH Single Domains That Rival the Stability and Cleft Recognition of Camelid Antibodies," (2015) Journal of Biological Chemistry 290(19):11905-11917.
Roux et al., "Comparisons of the Ability of Human lgG3 Hinge Mutants, IgM, IgE, and IgA2, to Form Small Immune Complexes: A Role for Flexibility and Geometry," (1998) Journal of Immunology 161(8):4083-4090.
Ryan et al., "Antibody Targeting of B-cell Maturation Antigen on Malignant Plasma Cells," (2007) Molecular Cancer Therapeutics 6(11):3009-3018.
Sadelain et al., "The Basic Principles of Chimeric Antigen Receptor Design," (2013) Cancer Discovery 3(4):388-398.
Sadelain et al., "CD19 CAR T Cells," (2017) Cell 171:1471.
Salazar-Camarena et al., " Association of BAFF, APRIL Serum Levels, BAFF-R, TACI and BCMA Expression on Peripheral B-cell Subsets with Clinical Manifestations in Systemic Lupus Erythematosus," (2016) Lupus 25:582-592.
Salmeron et al., "A conformational epitope expressed upon association of CD3-epsilon with either CD3-delta or CD3-gamma is the main target for recognition by anti-CD3 monoclonal antibodies." (1991) J Immunol 147(9):3047-3052.
Sanchez et al., "Serum B-cell Maturation Antigen Elevated in Multiple Myeloma and Correlates with Disease Status and Survival," (2012) Br J Haematol 158(6):727-738.
Sanz et al., "B cells as therapeutic targets in SLE," (2010) Nature Reviews Rheumatology 6:326-337.
Seckinger et al., "Target Expression, Generation, Preclinical Activity, and Pharmacokinetics of the BCMA-T Cell Bispecific Antibody EM801 for Multiple Myeloma Treatment," (2017) Cancer Cell, Cell Press US 31(3):396-410.
Shallis et al., "The Multi-faceted Potential of CD38 Antibody Targeting in Multiple Myeloma," (2017) Cancer Immunol Immunother 66:697-703.
Shields et al., "High Resolution Mapping of the Binding Site on Human IgGI for FcyRI, FcyRII, FcyRIll, and FcRn and Design of IgGI Variants with Improved Binding to the FcyR," (2001) J Biol Chem. 276(9):6591-6604.
Shoji-Hosaka et al., "Enhanced Fc-Dependent Cellular Cytotoxicity of Fc Fusion Proteins Derived from TNF Receptor II and LFA-3 by Fucose Removal from Asn-linked Oligosaccharides," (2006) Journal of Biochemistry 140:777-783.
Sitia et al., "Developmental regulation of IgM secretion: The role of the carboxy-terminal cysteine," (1990) Cell 60(5):781-790.
Statutory Declaration of Dr. Robert Saller, Executive Director Program Management at Amgen Research (Munich) GmbH (Vice President R&D Operations & Planning in Jan. 2011).
Supporting evidence that D41 was available in Jul. 2011 and thus before the claimed priority dates.
Tai et al., "APRIL and BCMA promote human multiple myeloma growth and immunosuppression in the bone marrow microenvironment," (2016) Blood 127(25):3225-3236.
Tai et al., "Novel anti-B-cell maturation antigen antibody-drug conjugate (GSK2857916) selectively induces killing of multiple myeloma," (2014) Blood 123(20):3128-3138.
Tao et al., "Structural features of human immunoglobulin G that determine isotype-specific differences in complement activation," (1993) Journal of Experimental Medicine 178(2):661-667.
Tarte et al., "BAFF is a survival factor for multiple myeloma cells," Myeloma Biology II: (2002) p. 811a (Abstract #3203).
TeneoBio, Inc., "A Study of TNB-383B in Subjects with Relapsed or Refractory Multiple Myeloma," (2019) [Rtrieved from the Internet on May 1, 2019] Retrieved from Internet: <URL: https:/ /clinicaltrials.gov/ct2/show/NCT03933735>.
Thakur et al., "Cancer therapy with bispecific antibodies: Clinical experience," (2010) Current Opinion in Molecular Therapeutics 12(3):340-349.
Thompson et al., "BAFF binds to the tumor necrosis factor receptor-like molecule B cell maturation antigen and is important for maintaining the peripheral B cell population," (2000) J Exp Medicine 192(1):129-135.
Topp et al., "Anti-B-Cell Maturation Antigen BiTE Molecule AMG 420 Induces Responses in Multiple Myeloma." (2020) J Clin Oncol 38(8):775-783.
Trinklein et al., "Efficient tumor killing and minimal cytokine release with novel T-cell agonist bispecific antibodies," (2019) MABS 11(4):639-652.
Trinklein et al., "Abstract LB-090: Sequence-based Discovery of Fully Human Anti-CD3 and Anti-PDL1 Single Domain Antibodies Using Novel Transgenic Rats," (2016) Cancer Research 76(14 Suppl).
Tueresson et al., "Patterns of Improved Survival in Patients with Multiple Myeloma in the Twenty-First Century: A Population-Based Study," (2010) Journal of Clinical Oncology 28(5):830-834.
Van der Linden et al., "Comparison of Physical Chemical Properties of Llama VHH Antibody Fragments and Mouse Monoclonal Antibodies," (1999) Biochim. Biophys. Acta. 1431(1):37-46.
Van Schooten et al., "A Novel CD3/BCMA Bispecific Antibody Selectively Kills Plasma Cells in Bone Marrow of Healthy Individuals with Improved Safety, " (2019) Lupus Science and Medicine 6(Supp 1):Abstract 293.
Verkleij et al., "T-Cell Redirecting Bispecific Antibodies Targeting BCMA for the Treatment of Multiple Myeloma," (2020) Oncotarget 11(45):4076-4081.
Vidal-Laliena et al., "Characterization of antibodies submitted to the B cell section of the 8th human leukocyte differentiation antigens workshop by flow cytometry and immunohistochemistry," (2005) Cellular Immunology 236:6-16.
Walker et al., "CD22: An Inhibitory Enigma," (2007) Immunology 123:314-325.
Wallweber et al., "The Crystal Structure of A Proliferation-inducing Ligand, APRIL," (2004) Journal of Molecular Biology 343:283-290.
Wang et al., "A systematic approach for analysis and characterization of mispairing in bispecific antibodies with asymmetric architecture," (2018) mAbs 10(8):1226-1235.
Waxman et al., "Racial disparities in incidence and outcome in multiple myeloma: a population-based study," (2010) Blood 116(25):5501-5506.
Wayback machine snapshot of BCMA UniprotKB/Swiss-Prot entry, Aug. 3, 2011 https://web.archive.org/web/20110803071256/ https://www.uniprot.orq/uniprot/Q02223.
Weidle et al., "The Intriguing Options of Multispecific Antibody Formats for Treatment of Cancer," (2013) Cancer Genomics & Proteomics 10(1):1-18.
Werther et al., "Humanization of Anti-lymphocyte Function-associated Antigen (LFA)-1 Monoclonal Antibody and Reengineering of the Humanized Antibody for Binding to Rhesus LFA-1," (1996) Journal of Immunology 157:4986-4995.
Woof et al., "Human antibody-Fe receptor interactions illuminated by crystal structures," (2004) Nat Rev Immunol 4(2):89-99.
Wu et al., "A novel VHH antibody targeting the B cell-activating factor for B-cell lymphoma," International Journal of Molecular Sciences 15(6):9481-9489.
Wu et al., "Simultaneous Targeting of Multiple Disease Mediators by a Dual-variable domain Immunoglobulin," (2007) Nature Biotechnology 25(11):1290-1297.
Xianchao, "The expression, purification and activity study of APRIL blocking Qi IJ BCMA-Fc," (2015) Chinese Excellent Doctoral Dissertation Full-text Database (Electronic Journal Network), Issue 2, E059-37:1-26.
Xiaomin et al., "Recent Advances in Tumor Therapy with Chimeric Antigen Receptor Modified T Cells," Medical Review 22(22).
Yan et al., "Recent Advances in Tumor Therapy with Chimeric Antigen Receptor Modified T Cells", Medical Review, 22(22):4417-4421 (2016).
Yoon et al., "Both High and Low Avidity Antibodies to the T Cell Receptor can have Agonist Activity," (1994) Immunity 1(7):563-569.

(56) References Cited

OTHER PUBLICATIONS

Zhao et al., "A germline knowledge based computational approach for determining antibody complementarity determining regions," (2010) Molecular Immunology 47(4):694-700.
Zou et al., "Heavy chain—only antibodies are spontaneously produced in light chain—deficient mice," (2007) J Exp Med 204(13) :3271-3283.
"A Global Search Engine for Antibodies (A Search for "#sc-57037" in the Antibody Directory, The Details for "#sc-57037" in the Antibody Directory, and A Search for "#sc-57037" in the Antibody Registry)," cited on Feb. 24, 2023, in the EP Opposition for EP2780375, 5 Pages.
A Report of an Epitope-exchange Study on the Binding of Vicky-1 to BCMA Epitope Cluster 3, Cited on Feb. 24, 2023, In the EP Opposition for EP2780375, 6 Pages.
ABCAM: "Product datasheet, Anti-BCMA antibody [Vicky-1] ab17323," cited on Sep. 9, 2022 in the EP Opposition for EP2780375, 3 Pages.
ALANINE-SCANNING Report, In the EP Opposition for EP2780375, Cited on Feb. 23, 2023, 9 Pages.
Alexaki V-I., et al., "Adipocytes as Immune Cells: Differential Expression of TWEAK, BAFF, and APRIL and their Receptors (Fn14, BAFF-R, TACI and BCMA) at Different Stages of Normal and Pathological Adipose Tissue Development," The Journal of Immunology, 2009, vol. 183, pp. 5948-5956.
ANONYMOUS: "Dose Escalation Study of Teclistamab, A Humanized BCMA*CD3 Bispecific Antibody, in Participants with Relapsed or Refractory Multiple Myeloma (MajesTEC-1)," National Institutes of Health, U.S. National Library of Medicine, ClinicalTrials.gov Identifier: NCT01314518, 2017, pp. 1-11, Retrieved from URL: https://www.clinicaltrials.gov/ct2/show/NCT03145181.
ANONYMOUS: "SinoBiological Inc-Antibody-Catalogue," 2016, 150 Pages, Retrieved from URL: https://cdnl.sinobiological.com/reagent/catalogue/antibody-catalogue-EN.pdf.
"Anti-BCMA (Human) (Vicky-1) (OAED00318)," Vicky-1 Datasheet , Aviva Systems Biology, cited on Feb. 24, 2023, in the EP Opposition for EP2780375, 2 Pages.
"BCMA Antibody [Vicky-1]," Vicky-1 Datasheet, GeneTex, Cat. No. GTX17323, cited on Feb. 24, 2023, in the EP Opposition for EP2780375, 1 Page.
"BCMA Monoclonal Antibody (Vicky-1)," Invitrogen, Datasheet, Lot No. VD2967484, cited on Feb. 24, 2023 in the EP Opposition for EP2780375, 1 Page.
"BCMA Monoclonal Antibody (Vicky-1)," Vicky-1 Datasheet, Invitrogen, cited on Feb. 24, 2023, in the EP Opposition for EP2780375, 1 Page.
"BCMA/TNFRSF17 Antibody (Vicky-1)—BSA Free," Vicky-1 Datasheet, Novus Biologicals, cited on Feb. 24, 2023 in the EP Opposition for EP2780375, 3 Pages.
Buelow B., et al., "Development of a Fully Human T-cell Engaging Bispecific Antibody for the Treatment of Multiple Myeloma," Journal of Clinical Oncology, Meeting Info: 2018 ASCO-SITC Clinical Immuno-Oncology Symposium, Feb. 10, 2018, vol. 36, No. 5_Supplement, Abstract No. 60, 3 Pages, Published Online on Feb. 26, 2018.
Buelow B., et al., "Effect of Modulation of Cd3 Binding in a Psmaxcd3 T-cell Engaging Bispecific Antibody on Maintenance of Efficient Tumor Cell Kill Cytokine Release," Journal of Clinical Oncology, 2020, vol. 38, No. 15, 4 Pages, Suppl. e17583, DOI: 10.1200/JC0.2020.38.15_suppl.e17583.
Buelow B., et al., "Evaluation of Monovalent Versus Biparatopic CD3xPSMA Bispecific Antibodies for Tcell Mediated Killing of Prostate Tumor Cells with Minimal Cytokine Release," Journal of Clinical Oncology, Meeting Info: Annual meeting of the American Society of Clinical Oncology, May 2019, vol. 37, No. 15_Supplement, Abstract No. e16519, 1 Page.
Buelow B., et al., "Pre-Clinical Development of TNB-383B, a Fully Human T-cell Engaging Bispecific Antibody Targeting BCMA for the Treatment of Multiple Myeloma," Journal of Clinical Oncology, May 20, 2018, vol. 36, No. 15_Supplement, Abstract No. 8034, pp. 1-4, Published Online on Jun. 1, 2018.
Buelow B., et al., "TNB585.001: A Multicenter, Phase 1, Open-Label, Dose-Escalation and Expansion Study of TNB-585, a Bispecific T-Cell Engager Targeting PSMA in Subjects with Metastatic Castrate Resistant Prostate Cancer," Journal of Clinical Oncology, 2021, vol. 39, No. 15_Supplement, Abstract No. TPS5092, pp. 1-4, Published Online May 28, 2021, DOI: 10.1200/JC0.2021.39.15_suppl.TPS5092.
CD3 Ortholog Alignment, Cited on Apr. 17, 2023 in the EP Opposition for EP2780375, 1 Page.
Chatenoud L., et al., "CD3 Monoclonal Antibodies: A First Step Towards Operational Immune Tolerance in the Clinic," The Review of Diabetic Studies, 2012, vol. 9, No. 4, pp. 372-381.
Claim Set filed on Feb. 3, 2023, in EP Application No. 21183531.9, cited on Apr. 17, 2023 in the EP Opposition for EP2780375, 2 Pages.
Clarke S., et al., "A Novel CD3xPSMA Bispecific Antibody for Efficient T Cell Mediated Killing of Prostate Tumor Cells with Minimal Cytokine Release," Journal of Clinical Oncology, Genitourinary Cancers Symposium, Mar. 1, 2019, vol. 37, Supplement 7, Abstract No. 324, 03 Pages, DOI: 10.1200/JCO.2019.37.7_suppl.324.
Clarke S., et al., "A Novel CD3xPSMA Bispecific Antibody for Efficient T Cell Mediated Killing of Prostate Tumor Cells with Minimal Cytokine Release," Journal of Clinical Oncology, Mar. 2019, vol. 37, Supplement 7, Abstract No. 324, 01 Page, DOI: 10.1200/JCO.2019.37.7_suppl.324.
Clinicaltrials.Gov: "A Study of AMG 340 in Subjects with Metastatic Castrate-Resistant Prostate Carcinoma," Clinicaltrials Identifier: NCT04740034, 2021, pp. 1-8.
Clinicaltrials.Gov: "Study of CC-93269, a BCMA x CD3 T Cell Engaging Antibody, In Participants With Relapsed and Refectory Multiple Myeloma," ID: NCT03486067, 2022, 3 Pages.
Certificate of Compliance for Vicky-1 Antibody from Abcam, Cited on Feb. 24, 2023 in the EP Opposition for EP2780375, 1 Page.
"Crystal Structure and Protein Interaction Analysis for AMG 701 scFv- BCMA," cited on Feb. 24, 2023 in the EP Opposition for EP2780375, 3 Pages.
Dang K., et al., "Attenuating CD3 Affinity in a PSMAxCD3 Bispecific Antibody Enables Killing of Prostate Tumor Cells with Reduced Cytokine Release," Journal for Immuno Therapy of Cancer, 2021, vol. 9: e002488, pp. 1-14.
Declaration of Dr. Christine E. Tinberg in EP 2780375 Opposition, EP Application No. 12805432.7, 2 Pages.
Declaration of Dr. Frank Mortari in EP 2780375 Opposition, EP Application No. 12805432.7, 7 Pages.
Declaration of Dr. Oliver Donze in EP 2780375 Opposition, EP Application No. 12805432.7, 28 Pages.
Dong D., et al., "Structural Basis of Assembly of the Human T Cell Receptor—CD3 Complex," Nature, Sep. 26, 2019, vol. 573, pp. 546-552, 21 Pages.
"Epitope Mapping of A2J, E2M, H2C, F12Q, H1E, F70, 12C, F6A, G4H Antibodies," Cited on Apr. 17, 2023 in the EP Opposition for EP2780375, Feb. 28, 2017, 4 Pages.
"Sequence Alignment Macaque CD3 Epsilon and SEQ ID Nos. 2, 4, 6, and 8 of D14," Macaque CD3 Epsilon Sequence, 1 Page, Retrieved from URL: https://www.uniprot.Org/uniprotkb/Q95LI5/entry#sequences.
"Sequence Alignment of BCMA Extracellular Domain; Human, Rhesus Macaque," in the EP Opposition for EP2780375, cited on Jun. 12, 2020, 1 page.
"Sequence Alignment of CD3 Epsilon N-term, aa1-27; Human, Crab-eating Macaque, Rhesus Macaque," cited on Jun. 12, 2020 in the EP Opposition for EP2780375, 1 Page.
Excerpt of the WHO "Proposed INN List 123," Referring to Pacanalotamab Entitled, "International Nonproprietary Names for Pharmaceutical Substances (INN)," Who Drug Information, 2020, vol. 34, No. 2, 5 Pages.
Foote J., et al., "Antibody Framework Residues Affecting the Conformation of the Hypervariable Loops," Journal of Molecular Biology, 1992, vol. 224, No. 2, pp. 487-499.

(56) References Cited

OTHER PUBLICATIONS

Goel M., et al., "Plasticity Within the Antigen-combining Site May Manifest as Molecular Mimicry in the Humoral Immune Response," The Journal of Immunology, Dec. 15, 2004, vol. 173, No. 12, pp. 7358-7367.
Goldstein R.L., et al., "AMG 701 Induces Cytotoxicity of Multiple Myeloma Cells and Depletes Plasma Cells in Cynomolgus Monkeys," Blood Advances, Sep. 8, 2020, vol. 4, No. 17:B1, pp. 4180-4194, 15 Pages.
Hagner P.R., et al., "Targeting B-cell Maturation Antigen (BCMA) With CC-93269, a 2+1 T Cell Engager, Elicits Significant Apoptosis in Diffuse Large B-cell Lymphoma Preclinical Models," Blood, Nov. 13, 2019, vol. 134, p. 1580, 3 Pages.
Han et al., "Single VHH-directed BCMA CAR-T cells cause remission of relapsed/refractory multiple myeloma," Leukemia 35, 3002-3006 (2021).
Imai-Nishiya H., et al., "Double Knockdown of α 1, 6-fucosyltransferase (FUT8) and GDP-mannose 4,6-dehydratase (GMD) in Antibody-producing Cells: A New Strategy for Generating Fully Non-fucosylated Therapeutic Antibodies with Enhanced ADCC," BMC Biotechnology, Nov. 30, 2007, vol. 7, No. 84, pp. 1-13.
In-house data from the Proprietors showing the KO of E1/E4-BCMA/CD3 bispecific antibodies and E3-BCMA/CD3 bispecific antibodies, entitled, "Affinities of BCMA/CD3 Bispecific Binding Molecules According to the Patent" 1 Page.
International Myeloma Society: "Bringing Together Clinical and Experimental Scientists Involved in the Study of Myeloma," Conference Abstracts of the International Myeloma Society, 19th Annual Meeting and Exposition, Los Angeles, California, Aug. 25-27, 2022, 222 Pages.
Ippoliti G., et al., "Immunomodulation with Rabbit Anti-Thymocyte Globulin in Solid Organ Transplantation," World Journal of Transplantation, Dec. 24, 2015, vol. 5, No. 4, pp. 261-266.
Jiang C., et al., "B Cell Maturation Antigen Deficiency Exacerbates Lymphoproliferation and Autoimmunity in Murine Lupus," The Journal of Immunology, 2011, vol. 186, No. 11, pp. 6136-6147.
Jones P.T., et al., "Replacing the Complementarity-determining Regions in a Human Antibody with Those from a Mouse," 1986, Nature vol. 321:522-525.
Kabat E.A., et al., "Sequences of Proteins of Immunological Interest," Bethesda, MD : U.S. Dept. of Health and Human Services, Public Health Service, National Institutes of Health, 1991, vol. 1, p. 310, 45 Pages, Retrieved from URL: https://books.google.co.uk/booksid=3jMvZYW2ZtwC&lpg=PA1137-IA1&pg=PP1#v=onepage&q&f=false.
Kishimoto H., et al., "Physical Dissociation of the TCR-CD3 Complex Accompanies Receptor Ligation," Journal of Experimental Medicine, Dec. 1995, vol. 182, pp. 1997-2006.
Kitagawa H., et al., "Differential Expression of Five Sialyltransferase Genes in Human Tissues," The Journal of Biological Chemistry, Jul. 8, 1994, vol. 269, No. 27, pp. 17872-17878, 08 Pages.
NCBI: "Immunoglobulin Heavy Chain Variable Region, Partial [Homo Sapiens]," GenBank Accession No. AIL30901.1, Aug. 31, 2014, 2 pages, Retrieved from the Internet URL: https://www.ncbi.nlm.nih.gov/protein/AIL30901.1/.
Lefranc M., et al., "IMGT, the International ImMunoGeneTics Database," Nucleic Acids Research, 1999, vol. 27, No. 1, pp. 209-212.
Mendel I., et al., "Activated T Cells Express the OX40 ligand: Requirements for Induction and Costimulatory Function," Immunology, Feb. 2006, vol. 117, No. 2, pp. 196-204.
Noel F., et al., "Global Analysis of VHHs Framework Regions with A Structural Alphabet," 2016, vol. 131, pp. 11-19.
Saerens D., et al., "Identification of a Universal VHH Framework to Graft Non-Canonical Antigen-Binding Loops of Camel Single-Domain Antibodies," Journal of Molecular Biology, 2005, vol. 352, pp. 597-607.

* cited by examiner

FIG. 1

| Name | CDR1 | CDR2 | CDR3 |
|---|---|---|---|
| BCMA heavy chain-only CDR sequences | GFTFSSNA (SEQ ID NO: 1) | ISGSGDYT (SEQ ID NO: 2) | AKEVPGGPLVDFDS (SEQ ID NO: 3) |
| La protein, v. 1, heavy chain CDR sequences | GYTFTHYY (SEQ ID NO: 4) | VNPSNGGT (SEQ ID NO: 5) | ARSEYDYGLGFAY (SEQ ID NO: 6) |
| La protein, v. 2, heavy chain CDR sequences | GYAFTHYY (SEQ ID NO: 7) | VNPSNGGT (SEQ ID NO: 5) | TRSEYDYGLGFAY (SEQ ID NO: 8) |
| La protein light chain CDR sequences | QSLLNSRTPKNY (SEQ ID NO: 9) | WAS (SEQ ID NO: 10) | KQSYNLLT (SEQ ID NO: 11) |

FIG. 2

| Name | Sequence |
|---|---|
| BCMA VH, monovalent | QVQLVESGGGLVQPGGSLRLSCVASGFTFSSNAMSWVRQAPGKGLEWVSAISGSGDYTHYSDSVKGRFTISRDNSKNTLYLQMNSLRAEDTAVYYCAKEVPGGPLVDFDSRGQGTLVTVSS (SEQ ID NO: 12) |
| BCMA VHH, bivalent, $GS_2$ linker | QVQLVESGGGLVQPGGSLRLSCVASGFTFSSNAMSWVRQAPGKGLEWVSAISGSGDYTHYSDSVKGRFTISRDNSKNTLYLQMNSLRAEDTAVYYCAKEVPGGPLVDFDSRGQGTLVTVSSGGGGSGGGGSQVQLVESGGGLVQPGGSLRLSCVASGFTFSSNAMSWVRQAPGKGLEWVSAISGSGDYTHYSDSVKGRFTISRDNSKNTLYLQMNSLRAEDTAVYYCAKEVPGGPLVDFDSRGQGTLVTVSS (SEQ ID NO: 13) |

FIG. 3

| Name | Sequence |
|---|---|
| La protein VH, v. 1 | QVQLVQSGAEVKKPGASVKVSCKASGYTFTHYYIYWVRQAPGQGLEWMGGVNPSNGGTHFNEKFKSRVTMTRDTSISTAYMELSRLRSDDTAVYYCARSEYDYGLGFAYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRV (SEQ ID NO: 14) |
| La protein VH, v. 2 | QVQLVQSGAEVKKPGASVKVSCKASGYAFTHYYIYWVRQAPGQGLEWIGGVNPSNGGTHFNEKFQGRVTMTRDTSISTAYMELSRLRSDDTAVYYCTRSEYDYGLGFAYASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRV (SEQ ID NO: 15) |
| La protein VL, v. 1 | DIVMTQSPDSLAVSLGERATINCKSSQSLLNSRTPKNYLAWYQQKPGQPPKLLIYWASTRKSGVPDRFSGSGSGTDFTLTISSLQAEDVAVYYCKQSYNLLTFGGGTKVEIK (SEQ ID NO: 16) |
| La protein VL, v. 2 | DIVMTQSPDSLAVSLGERATINCKSSQSLLNSRTPKNYLAWYQQKPGQPPKLLIYWASTRESGVPDRFSGSGSGTDFTLTISSLQAEDVAVYYCKQSYNLLTFGQGTKVEIK (SEQ ID NO: 17) |

FIG. 4

| Name | Sequence |
|---|---|
| La protein, full length HC, v. 1, variant IgG4 (S228P, F234A, L235A), knob (T366W) | QVQLVQSGAEVKKPGASVKVSCKASGYTFTHYYIYWVRQAPGQGLEWMGGVNPSNGGTHFNEKFKSRVTMTRDTSISTAYMELSRLRSDDTAVYYCARSEYDYGLGFAYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCP**P**CPAPE**AA**GGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSL**W**CLVKGFYPSDIAVEWESNGQPENNYKTTPPVLDSDGSFFLYSRLTVDKSRWQEGNVFSCSVMHEALHNHYTQKSLSLSLGK (SEQ ID NO: 18) |
| La protein, full length HC, v. 1, variant IgG4 (S228P, F234A, L235A), hole (T366S, L368A, Y407V) | QVQLVQSGAEVKKPGASVKVSCKASGYTFTHYYIYWVRQAPGQGLEWMGGVNPSNGGTHFNEKFKSRVTMTRDTSISTAYMELSRLRSDDTAVYYCARSEYDYGLGFAYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCP**P**CPAPE**AA**GGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSL**S**C**A**VKGFYPSDIAVEWESNGQPENNYKTTPPVLDSDGSFFL**V**SRLTVDKSRWQEGNVFSCSVMHEALHNHYTQKSLSLSLGK (SEQ ID NO: 19) |
| La protein, full length LC, v. 1 | DIVMTQSPDSLAVSLGERATINCKSSQSLLNSRTPKNYLAWYQQKPGQPPKLLIYWASTRKSGVPDRFSGSGSGTDFTLTISSLQAEDVAVYYCKQSYNLLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 20) |
| La protein, full length HC, v. 2, variant IgG4 (S228P, F234A, L235A), knob (T366W) | QVQLVQSGAEVKKPGASVKVSCKASGYAFTHYYIYWVRQAPGQGLEWIGGVNPSNGGTHFNEKFQGRVTMTRDTSISTAYMELSRLRSDDTAVYYCTRSEYDYGLGFAYASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCP**P**CPAPE**AA**GGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSL**W**CLVKGFYPSDIAVEWESNGQPENNYKTTPPVLDSDGSFFLYSRLTVDKSRWQEGNVFSCSVMHEALHNHYTQKSLSLSLGK (SEQ ID NO: 21) |

FIG. 4, cont.

| Name | Sequence |
|---|---|
| La protein, full length HC, v. 2, variant IgG4 (S228P, F234A, L235A), hole (T366S, L368A, Y407V) | QVQLVQSGAEVKKPGASVKVSCKASGYAFTHYYIYWVRQAPGQGLEWI GGVNPSNGGTHFNEKFQGRVTMTRDTSISTAYMELSRLRSDDTAVYYCT RSEYDYGLGFAYASTKGPSVFPLAPCSRSTSESTAALGCLVKDYFPEPVTV SWNSGALTSGVHTFPAVLQSSGLYSLSSVVTVPSSSLGTKTYTCNVDHKP SNTKVDKRVESKYGPPCP**P**CPAPE**AA**GGPSVFLFPPKPKDTLMISRTPEV TCVVVDVSQEDPEVQFNWYVDGVEVHNAKTKPREEQFNSTYRVVSVLT VLHQDWLNGKEYKCKVSNKGLPSSIEKTISKAKGQPREPQVYTLPPSQEE MTKNQVSL**S**C**A**VKGFYPSDIAVEWESNGQPENNYKTTPPVLDSDGSFFL **V**SRLTVDKSRWQEGNVFSCSVMHEALHNHYTQKSLSLSLGK (SEQ ID NO: 22) |
| La protein, full length LC, v. 2 | DIVMTQSPDSLAVSLGERATINCKSSQSLLNSRTPKNYLAWYQQKPGQPP KLLIYWASTRESGVPDRFSGSGSGTDFTLTISSLQAEDVAVYYCKQSYNLL TFGQGTKVEIKRTVAAPSVFIFPPSDEQLKSGTASVVCLLNNFYPREAKVQ WKVDNALQSGNSQESVTEQDSKDSTYSLSSTLTLSKADYEKHKVYACEV THQGLSSPVTKSFNRGEC (SEQ ID NO: 23) |

FIG. 5

| Name | Sequence |
|---|---|
| BCMA monovalent HCO HC, variant IgG4 (S228P, F234A, L235A), hole (T366S, L368A, Y407V) | QVQLVESGGGLVQPGGSLRLSCVASGFTFSSNAMSWVRQAPGKGLEWVS AISGSGDYTHYSDSVKGRFTISRDNSKNTLYLQMNSLRAEDTAVYYCAKE VPGGPLVDFDSRGQGTLVTVSSESKYGPPCP**P**CPAPE**AA**GGPSVFLFPP KPKDTLMISRTPEVTCVVVDVSQEDPEVQFNWYVDGVEVHNAKTKPREE QFNSTYRVVSVLTVLHQDWLNGKEYKCKVSNKGLPSSIEKTISKAKGQPR EPQVYTLPPSQEEMTKNQVSL**S**C**A**VKGFYPSDIAVEWESNGQPENNYKT TPPVLDSDGSFFL**V**SRLTVDKSRWQEGNVFSCSVMHEALHNHYTQKSLS LSLGK (SEQ ID NO: 24) |
| BCMA monovalent HCO HC, variant IgG4 (S228P, F234A, L235A) knob (T366W) | QVQLVESGGGLVQPGGSLRLSCVASGFTFSSNAMSWVRQAPGKGLEWVS AISGSGDYTHYSDSVKGRFTISRDNSKNTLYLQMNSLRAEDTAVYYCAKE VPGGPLVDFDSRGQGTLVTVSSESKYGPPCP**P**CPAPE**AA**GGPSVFLFPP KPKDTLMISRTPEVTCVVVDVSQEDPEVQFNWYVDGVEVHNAKTKPREE QFNSTYRVVSVLTVLHQDWLNGKEYKCKVSNKGLPSSIEKTISKAKGQPR EPQVYTLPPSQEEMTKNQVSL**W**CLVKGFYPSDIAVEWESNGQPENNYK TTPPVLDSDGSFFLYSRLTVDKSRWQEGNVFSCSVMHEALHNHYTQKSLS LSLGK (SEQ ID NO: 25) |
| BCMA bivalent HCO, $GS_2$ linker, HC, variant IgG4 (S228P, F234A, L235A), hole (T366S, L368A, Y407V) | QVQLVESGGGLVQPGGSLRLSCVASGFTFSSNAMSWVRQAPGKGLEWVS AISGSGDYTHYSDSVKGRFTISRDNSKNTLYLQMNSLRAEDTAVYYCAKE VPGGPLVDFDSRGQGTLVTVSSGGGGSGGGGSQVQLVESGGGLVQPGGS LRLSCVASGFTFSSNAMSWVRQAPGKGLEWVSAISGSGDYTHYSDSVKG RFTISRDNSKNTLYLQMNSLRAEDTAVYYCAKEVPGGPLVDFDSRGQGT LVTVSSESKYGPPCP**P**CPAPE**AA**GGPSVFLFPPKPKDTLMISRTPEVTCV VVDVSQEDPEVQFNWYVDGVEVHNAKTKPREEQFNSTYRVVSVLTVLH QDWLNGKEYKCKVSNKGLPSSIEKTISKAKGQPREPQVYTLPPSQEEMTK NQVSL**S**C**A**VKGFYPSDIAVEWESNGQPENNYKTTPPVLDSDGSFFL**V**SR LTVDKSRWQEGNVFSCSVMHEALHNHYTQKSLSLSLGK (SEQ ID NO: 26) |
| BCMA bivalent HCO, $GS_2$ linker, HC, variant IgG4 (S228P, F234A, L235A), knob (T366W) | QVQLVESGGGLVQPGGSLRLSCVASGFTFSSNAMSWVRQAPGKGLEWVS AISGSGDYTHYSDSVKGRFTISRDNSKNTLYLQMNSLRAEDTAVYYCAKE VPGGPLVDFDSRGQGTLVTVSSGGGGSGGGGSQVQLVESGGGLVQPGGS LRLSCVASGFTFSSNAMSWVRQAPGKGLEWVSAISGSGDYTHYSDSVKG RFTISRDNSKNTLYLQMNSLRAEDTAVYYCAKEVPGGPLVDFDSRGQGT LVTVSSESKYGPPCP**P**CPAPE**AA**GGPSVFLFPPKPKDTLMISRTPEVTCV VVDVSQEDPEVQFNWYVDGVEVHNAKTKPREEQFNSTYRVVSVLTVLH QDWLNGKEYKCKVSNKGLPSSIEKTISKAKGQPREPQVYTLPPSQEEMTK NQVSL**W**CLVKGFYPSDIAVEWESNGQPENNYKTTPPVLDSDGSFFLYSR LTVDKSRWQEGNVFSCSVMHEALHNHYTQKSLSLSLGK (SEQ ID NO: 27) |

FIG. 6

| Name | Sequence |
|---|---|
| Human IgG4 WT (Fc) | ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPSCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK (SEQ ID NO: 28) |
| Human IgG4 knob (T366W, numbering per IgG1) | ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPSCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSL**W**CLVKGFYPSDIAVEWESNGQPENNYKTTPPVLDSDGSFFLYSRLTVDKSRWQEGNVFSCSVMHEALHNHYTQKSLSLSLGK (SEQ ID NO: 29) |
| Human IgG4 hole (T366S, L368A, Y407V, numbering per IgG1) | ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPSCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSL**S**C**A**VKGFYPSDIAVEWESNGQPENNYKTTPPVLDSDGSFFL**V**SRLTVDKSRWQEGNVFSCSVMHEALHNHYTQKSLSLSLGK (SEQ ID NO: 30) |
| Human kappa light chain constant region sequence (Uniprot P01834) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 31) |
| Human lambda light chain constant region sequence (Uniprot P0CG04) | GQPKANPTVTLFPPSSEELQANKATLVCLISDFYPGAVTVAWKADGSPVKAGVETTKPSKQSNNKYAASSYLSLTPEQWKSHRSYSCQVTHEGSTVEKTVAPTECS (SEQ ID NO: 41) |
| WT IgG4 HC hinge | ESKYGPPCPSCPA (SEQ ID NO: 32) |
| HC IgG4 hinge S228P | ESKYGPPCP**P**CPA (SEQ ID NO: 33) |

FIG. 6, cont.

| Name | Sequence |
|---|---|
| GS4 linker | GGGGS (SEQ ID NO: 34) |
| $GS4_2$ linker sequence | GGGGSGGGGS (SEQ ID NO: 35) |
| La protein epitope 1 | KPLPEVTDEY (SEQ ID NO: 42) |
| La protein epitope 2 | VEKEALKKIIEDQQESLNKW (SEQ ID NO: 43) |
| Human IgG4 CH2 domain, wild type | APEFLGGPSVFLFPPKPKDTLMISRTPEVTCVVVDVSQEDPEVQFNWY VDGVEVHNAKTKPREEQFNSTYRVVSVLTVLHQDWLNGKEYKCKV SNKGLPSSIEKTISKAK (SEQ ID NO: 36) |
| Human IgG4 CH2 domain, silenced (F234A, L235A) | APE**AA**GGPSVFLFPPKPKDTLMISRTPEVTCVVVDVSQEDPEVQFN WYVDGVEVHNAKTKPREEQFNSTYRVVSVLTVLHQDWLNGKEYKC KVSNKGLPSSIEKTISKAK (SEQ ID NO: 37) |
| Human IgG4 CH3 domain, wild type | GQPREPQVYTLPPSQEEMTKNQVSLTCLVKGFYPSDIAVEWESNGQP ENNYKTTPPVLDSDGSFFLYSRLTVDKSRWQEGNVFSCSVMHEALHN HYTQKSLSLSLGK (SEQ ID NO: 38) |
| Human IgG4 CH3 domain, knob (T366W) | GQPREPQVYTLPPSQEEMTKNQVSL**W**CLVKGFYPSDIAVEWESNGQ PENNYKTTPPVLDSDGSFFLYSRLTVDKSRWQEGNVFSCSVMHEALH NHYTQKSLSLSLGK (SEQ ID NO: 39) |
| Human IgG4 CH3 domain, hole (T366S, L368A, Y407V) | GQPREPQVYTLPPSQEEMTKNQVSL**S**C**A**VKGFYPSDIAVEWESNGQ PENNYKTTPPVLDSDGSFFL**V**SRLTVDKSRWQEGNVFSCSVMHEAL HNHYTQKSLSLSLGK (SEQ ID NO: 40) |

FIG. 7
A.
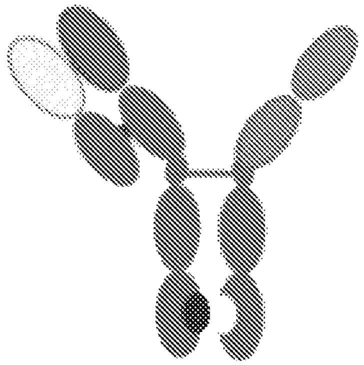
B.
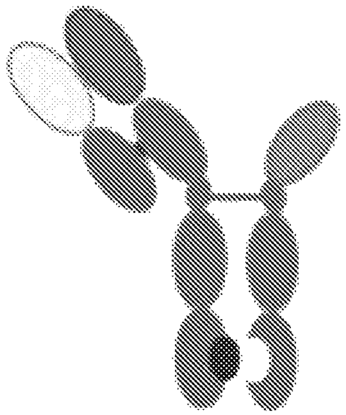

FIG. 8
A.
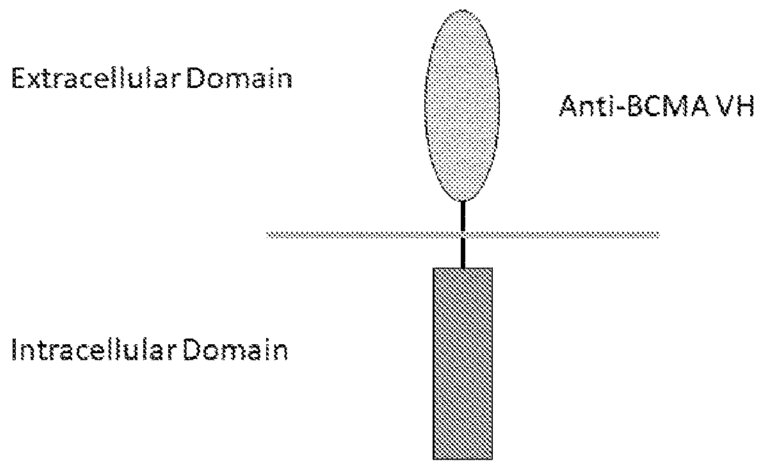
B.
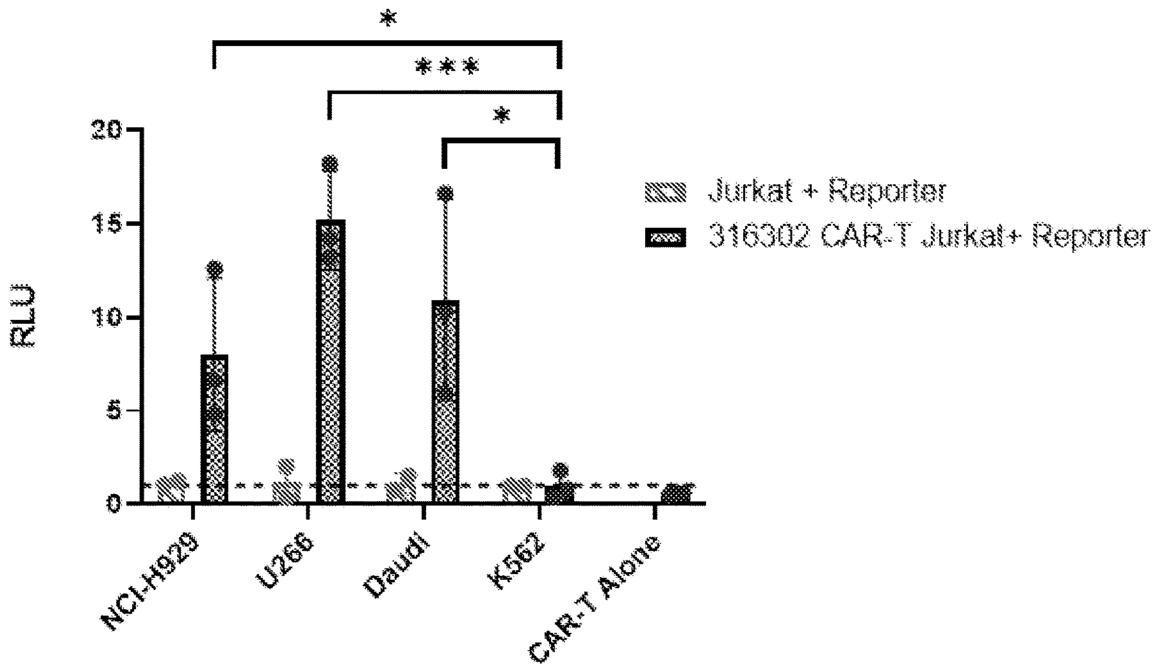

FIG. 9
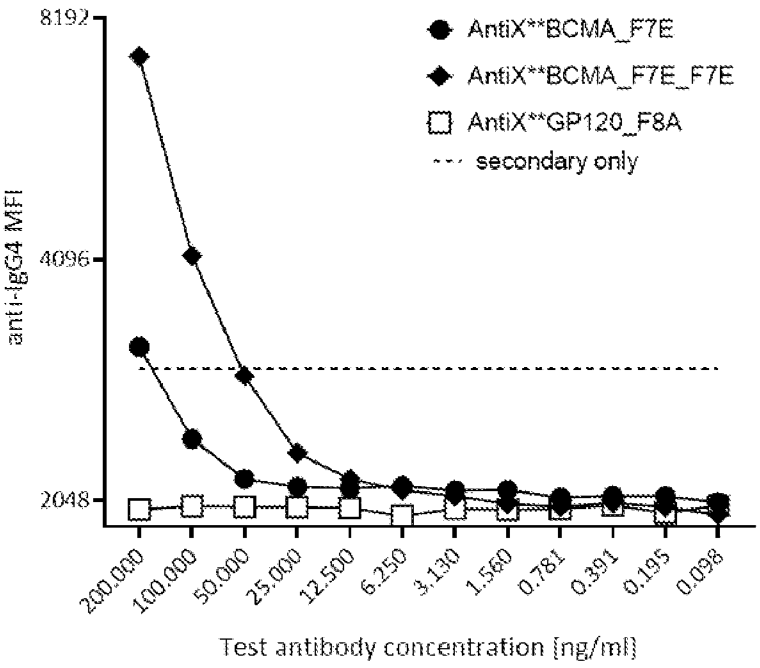
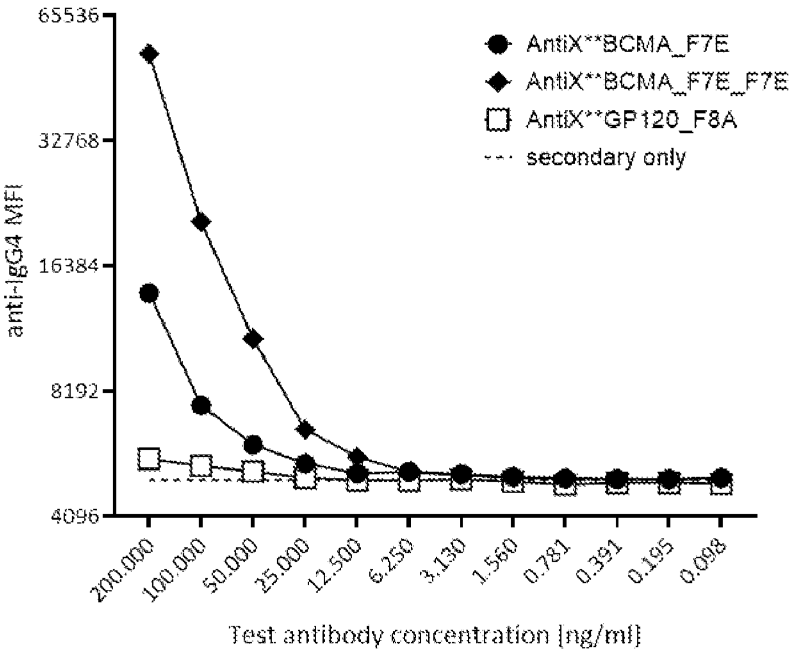

FIG. 10
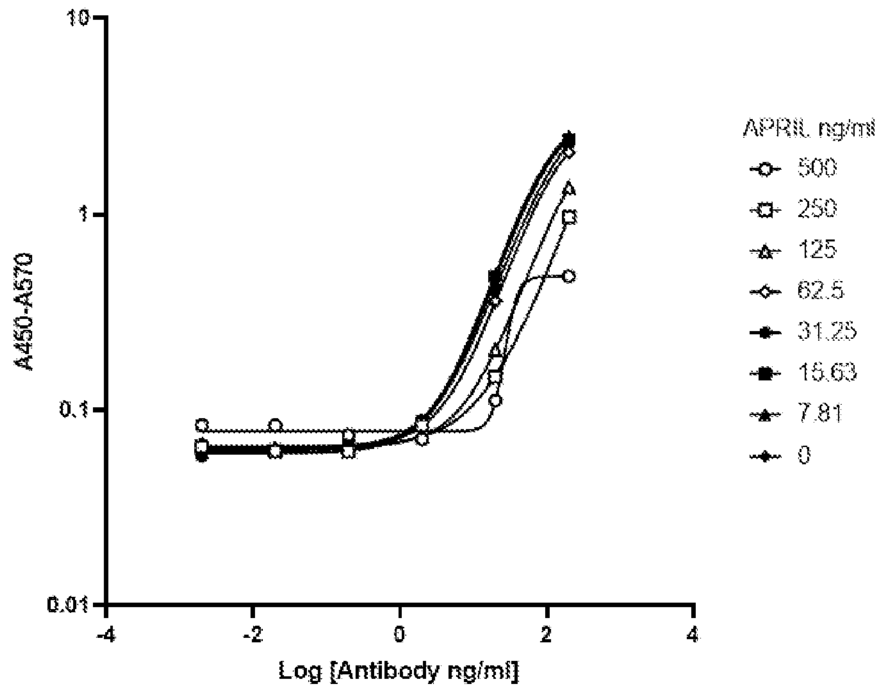
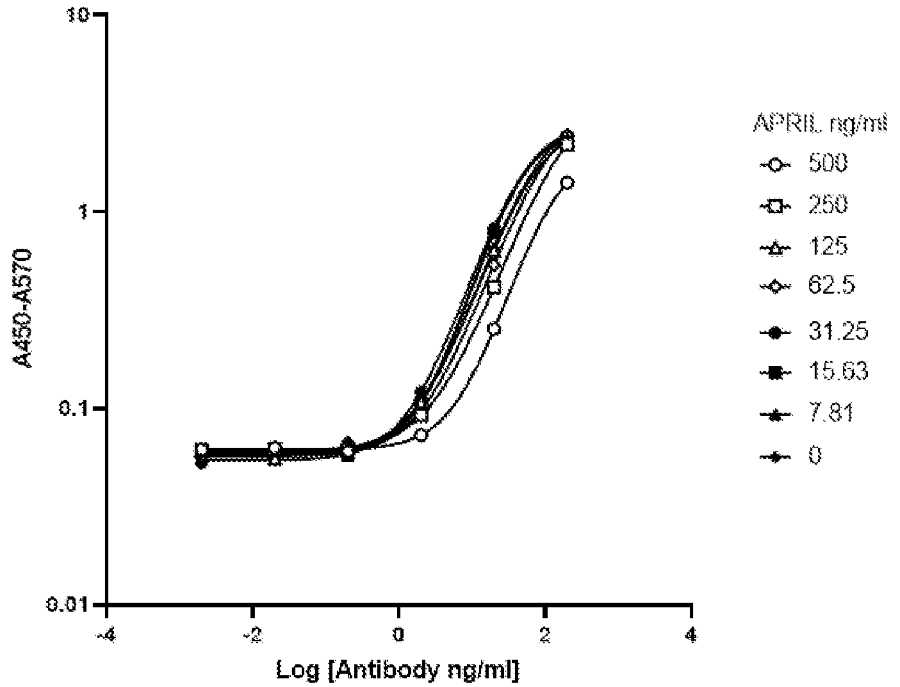

FIG. 10, Con't.
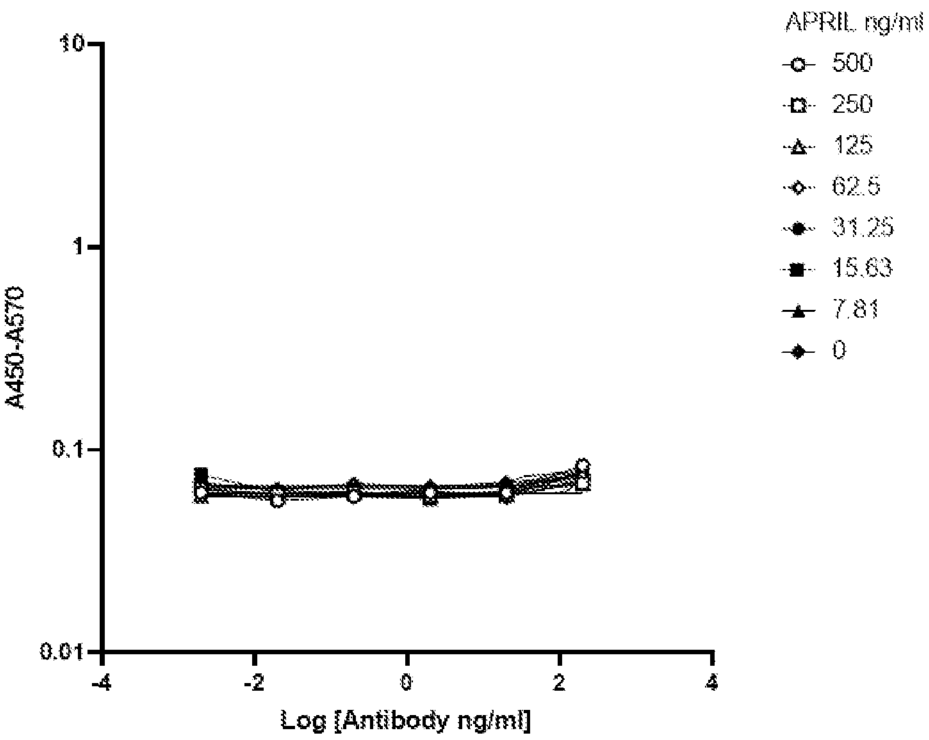

SEQUENCE LISTING

```
<160> NUMBER OF SEQ ID NOS: 43

<210> SEQ ID NO 1
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Phe Thr Phe Ser Ser Asn Ala
1               5


<210> SEQ ID NO 2
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Ile Ser Gly Ser Gly Asp Tyr Thr
1               5


<210> SEQ ID NO 3
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Ala Lys Glu Val Pro Gly Gly Pro Leu Val Asp Phe Asp Ser
1               5                   10
```

<210> SEQ ID NO 4
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 4

Gly Tyr Thr Phe Thr His Tyr Tyr
1 5

<210> SEQ ID NO 5
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 5

Val Asn Pro Ser Asn Gly Gly Thr
1 5

<210> SEQ ID NO 6
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 6

Ala Arg Ser Glu Tyr Asp Tyr Gly Leu Gly Phe Ala Tyr
1 5 10

<210> SEQ ID NO 7
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 7

Gly Tyr Ala Phe Thr His Tyr Tyr
1 5

<210> SEQ ID NO 8
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 8

Thr Arg Ser Glu Tyr Asp Tyr Gly Leu Gly Phe Ala Tyr
1 5 10

<210> SEQ ID NO 9
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 9

Gln Ser Leu Leu Asn Ser Arg Thr Pro Lys Asn Tyr
1 5 10

<210> SEQ ID NO 10
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 10

Trp Ala Ser
1

<210> SEQ ID NO 11
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 11

Lys Gln Ser Tyr Asn Leu Leu Thr
1 5

<210> SEQ ID NO 12
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 12

Gln Val Gln Leu Val Glu Ser Gly Gly Gly Leu Val Gln Pro Gly Gly
1 5 10 15

Ser Leu Arg Leu Ser Cys Val Ala Ser Gly Phe Thr Phe Ser Ser Asn
20 25 30

Ala Met Ser Trp Val Arg Gln Ala Pro Gly Lys Gly Leu Glu Trp Val
35 40 45

Ser Ala Ile Ser Gly Ser Gly Asp Tyr Thr His Tyr Ser Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Glu Val Pro Gly Gly Pro Leu Val Asp Phe Asp Ser Arg Gly
100 105 110

Gln Gly Thr Leu Val Thr Val Ser Ser
115 120

<210> SEQ ID NO 13
<211> LENGTH: 252

<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 13

```
Gln Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Ser Asn
            20                  25                  30

Ala Met Ser Trp Val Arg Gln Ala Pro Gly Lys Gly Leu Glu Trp Val
        35                  40                  45

Ser Ala Ile Ser Gly Ser Gly Asp Tyr Thr His Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Val Pro Gly Gly Pro Leu Val Asp Phe Asp Ser Arg Gly
            100                 105                 110

Gln Gly Thr Leu Val Thr Val Ser Ser Gly Gly Gly Gly Ser Gly Gly
        115                 120                 125

Gly Gly Ser Gln Val Gln Leu Val Glu Ser Gly Gly Gly Leu Val Gln
    130                 135                 140

Pro Gly Gly Ser Leu Arg Leu Ser Cys Val Ala Ser Gly Phe Thr Phe
145                 150                 155                 160

Ser Ser Asn Ala Met Ser Trp Val Arg Gln Ala Pro Gly Lys Gly Leu
                165                 170                 175

Glu Trp Val Ser Ala Ile Ser Gly Ser Gly Asp Tyr Thr His Tyr Ser
            180                 185                 190

Asp Ser Val Lys Gly Arg Phe Thr Ile Ser Arg Asp Asn Ser Lys Asn
        195                 200                 205

Thr Leu Tyr Leu Gln Met Asn Ser Leu Arg Ala Glu Asp Thr Ala Val
    210                 215                 220

Tyr Tyr Cys Ala Lys Glu Val Pro Gly Gly Pro Leu Val Asp Phe Asp
225                 230                 235                 240

Ser Arg Gly Gln Gly Thr Leu Val Thr Val Ser Ser
                245                 250
```

<210> SEQ ID NO 14
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 14

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr His Tyr
            20                  25                  30

Tyr Ile Tyr Trp Val Arg Gln Ala Pro Gly Gln Gly Leu Glu Trp Met
        35                  40                  45

Gly Gly Val Asn Pro Ser Asn Gly Gly Thr His Phe Asn Glu Lys Phe
```

```
    50                  55                  60

Lys Ser Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Glu Tyr Asp Tyr Gly Leu Gly Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val
    210                 215


<210> SEQ ID NO 15
<211> LENGTH: 207
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr His Tyr
            20                  25                  30

Tyr Ile Tyr Trp Val Arg Gln Ala Pro Gly Gln Gly Leu Glu Trp Ile
        35                  40                  45

Gly Gly Val Asn Pro Ser Asn Gly Gly Thr His Phe Asn Glu Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Glu Tyr Asp Tyr Gly Leu Gly Phe Ala Tyr Ala Ser Thr
            100                 105                 110

Lys Gly Pro Ser Val Phe Pro Leu Ala Pro Cys Ser Arg Ser Thr Ser
        115                 120                 125

Glu Ser Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Lys Thr Tyr Thr Cys
            180                 185                 190
```

```
Asn Val Asp His Lys Pro Ser Asn Thr Lys Val Asp Lys Arg Val
        195                 200                 205


<210> SEQ ID NO 16
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Pro Lys Asn Tyr Leu Ala Trp Tyr Gln Gln Lys Pro Gly Gln
        35                  40                  45

Pro Pro Lys Leu Leu Ile Tyr Trp Ala Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Leu Thr Phe Gly Gly Gly Thr Lys Val Glu Ile Lys
            100                 105                 110


<210> SEQ ID NO 17
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Pro Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Leu Thr Phe Gly Gln Gly Thr Lys Val Glu Ile Lys
            100                 105                 110


<210> SEQ ID NO 18
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 18

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr His Tyr
            20                  25                  30

Tyr Ile Tyr Trp Val Arg Gln Ala Pro Gly Gln Gly Leu Glu Trp Met
        35                  40                  45

Gly Gly Val Asn Pro Ser Asn Gly Gly Thr His Phe Asn Glu Lys Phe
    50                  55                  60

Lys Ser Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Glu Tyr Asp Tyr Gly Leu Gly Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Trp Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
```

```
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 19
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr His Tyr
            20                  25                  30

Tyr Ile Tyr Trp Val Arg Gln Ala Pro Gly Gln Gly Leu Glu Trp Met
        35                  40                  45

Gly Gly Val Asn Pro Ser Asn Gly Gly Thr His Phe Asn Glu Lys Phe
    50                  55                  60

Lys Ser Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Glu Tyr Asp Tyr Gly Leu Gly Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320
```

```
Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Ser Cys Ala
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 20
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Pro Lys Asn Tyr Leu Ala Trp Tyr Gln Gln Lys Pro Gly Gln
        35                  40                  45

Pro Pro Lys Leu Leu Ile Tyr Trp Ala Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 21
<211> LENGTH: 436
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 21

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr His Tyr
            20                  25                  30

Tyr Ile Tyr Trp Val Arg Gln Ala Pro Gly Gln Gly Leu Glu Trp Ile
        35                  40                  45

Gly Gly Val Asn Pro Ser Asn Gly Gly Thr His Phe Asn Glu Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Glu Tyr Asp Tyr Gly Leu Gly Phe Ala Tyr Ala Ser Thr
            100                 105                 110

Lys Gly Pro Ser Val Phe Pro Leu Ala Pro Cys Ser Arg Ser Thr Ser
        115                 120                 125

Glu Ser Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Lys Thr Tyr Thr Cys
            180                 185                 190

Asn Val Asp His Lys Pro Ser Asn Thr Lys Val Asp Lys Arg Val Glu
        195                 200                 205

Ser Lys Tyr Gly Pro Pro Cys Pro Pro Cys Pro Ala Pro Glu Ala Ala
    210                 215                 220

Gly Gly Pro Ser Val Phe Leu Phe Pro Pro Lys Pro Lys Asp Thr Leu
225                 230                 235                 240

Met Ile Ser Arg Thr Pro Glu Val Thr Cys Val Val Val Asp Val Ser
                245                 250                 255

Gln Glu Asp Pro Glu Val Gln Phe Asn Trp Tyr Val Asp Gly Val Glu
            260                 265                 270

Val His Asn Ala Lys Thr Lys Pro Arg Glu Glu Gln Phe Asn Ser Thr
        275                 280                 285

Tyr Arg Val Val Ser Val Leu Thr Val Leu His Gln Asp Trp Leu Asn
    290                 295                 300

Gly Lys Glu Tyr Lys Cys Lys Val Ser Asn Lys Gly Leu Pro Ser Ser
305                 310                 315                 320

Ile Glu Lys Thr Ile Ser Lys Ala Lys Gly Gln Pro Arg Glu Pro Gln
                325                 330                 335

Val Tyr Thr Leu Pro Pro Ser Gln Glu Glu Met Thr Lys Asn Gln Val
            340                 345                 350

Ser Leu Trp Cys Leu Val Lys Gly Phe Tyr Pro Ser Asp Ile Ala Val
```

```
        355                 360                 365

Glu Trp Glu Ser Asn Gly Gln Pro Glu Asn Asn Tyr Lys Thr Thr Pro
    370                 375                 380

Pro Val Leu Asp Ser Asp Gly Ser Phe Phe Leu Tyr Ser Arg Leu Thr
385                 390                 395                 400

Val Asp Lys Ser Arg Trp Gln Glu Gly Asn Val Phe Ser Cys Ser Val
                405                 410                 415

Met His Glu Ala Leu His Asn His Tyr Thr Gln Lys Ser Leu Ser Leu
            420                 425                 430

Ser Leu Gly Lys
        435


<210> SEQ ID NO 22
<211> LENGTH: 436
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr His Tyr
            20                  25                  30

Tyr Ile Tyr Trp Val Arg Gln Ala Pro Gly Gln Gly Leu Glu Trp Ile
        35                  40                  45

Gly Gly Val Asn Pro Ser Asn Gly Gly Thr His Phe Asn Glu Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Glu Tyr Asp Tyr Gly Leu Gly Phe Ala Tyr Ala Ser Thr
            100                 105                 110

Lys Gly Pro Ser Val Phe Pro Leu Ala Pro Cys Ser Arg Ser Thr Ser
        115                 120                 125

Glu Ser Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Lys Thr Tyr Thr Cys
            180                 185                 190

Asn Val Asp His Lys Pro Ser Asn Thr Lys Val Asp Lys Arg Val Glu
        195                 200                 205

Ser Lys Tyr Gly Pro Pro Cys Pro Pro Cys Pro Ala Pro Glu Ala Ala
    210                 215                 220

Gly Gly Pro Ser Val Phe Leu Phe Pro Pro Lys Pro Lys Asp Thr Leu
225                 230                 235                 240

Met Ile Ser Arg Thr Pro Glu Val Thr Cys Val Val Val Asp Val Ser
                245                 250                 255

Gln Glu Asp Pro Glu Val Gln Phe Asn Trp Tyr Val Asp Gly Val Glu
            260                 265                 270
```

```
Val His Asn Ala Lys Thr Lys Pro Arg Glu Glu Gln Phe Asn Ser Thr
        275                 280                 285

Tyr Arg Val Val Ser Val Leu Thr Val Leu His Gln Asp Trp Leu Asn
    290                 295                 300

Gly Lys Glu Tyr Lys Cys Lys Val Ser Asn Lys Gly Leu Pro Ser Ser
305                 310                 315                 320

Ile Glu Lys Thr Ile Ser Lys Ala Lys Gly Gln Pro Arg Glu Pro Gln
                325                 330                 335

Val Tyr Thr Leu Pro Pro Ser Gln Glu Glu Met Thr Lys Asn Gln Val
            340                 345                 350

Ser Leu Ser Cys Ala Val Lys Gly Phe Tyr Pro Ser Asp Ile Ala Val
        355                 360                 365

Glu Trp Glu Ser Asn Gly Gln Pro Glu Asn Asn Tyr Lys Thr Thr Pro
    370                 375                 380

Pro Val Leu Asp Ser Asp Gly Ser Phe Phe Leu Val Ser Arg Leu Thr
385                 390                 395                 400

Val Asp Lys Ser Arg Trp Gln Glu Gly Asn Val Phe Ser Cys Ser Val
                405                 410                 415

Met His Glu Ala Leu His Asn His Tyr Thr Gln Lys Ser Leu Ser Leu
            420                 425                 430

Ser Leu Gly Lys
        435


<210> SEQ ID NO 23
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Pro Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Leu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175
```

```
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 24
<211> LENGTH: 350
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Gln Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Ser Asn
            20                  25                  30

Ala Met Ser Trp Val Arg Gln Ala Pro Gly Lys Gly Leu Glu Trp Val
        35                  40                  45

Ser Ala Ile Ser Gly Ser Gly Asp Tyr Thr His Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Val Pro Gly Gly Pro Leu Val Asp Phe Asp Ser Arg Gly
            100                 105                 110

Gln Gly Thr Leu Val Thr Val Ser Ser Glu Ser Lys Tyr Gly Pro Pro
        115                 120                 125

Cys Pro Pro Cys Pro Ala Pro Glu Ala Ala Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser Gln Glu Asp Pro Glu Val
                165                 170                 175

Gln Phe Asn Trp Tyr Val Asp Gly Val Glu Val His Asn Ala Lys Thr
            180                 185                 190

Lys Pro Arg Glu Glu Gln Phe Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Gly Leu Pro Ser Ser Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Gln Glu Glu Met Thr Lys Asn Gln Val Ser Leu Ser Cys Ala Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Val Ser Arg Leu Thr Val Asp Lys Ser Arg Trp
```

```
305                 310                 315                 320

Gln Glu Gly Asn Val Phe Ser Cys Ser Val Met His Glu Ala Leu His
                325                 330                 335

Asn His Tyr Thr Gln Lys Ser Leu Ser Leu Ser Leu Gly Lys
            340                 345                 350


<210> SEQ ID NO 25
<211> LENGTH: 350
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Gln Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Ser Asn
            20                  25                  30

Ala Met Ser Trp Val Arg Gln Ala Pro Gly Lys Gly Leu Glu Trp Val
        35                  40                  45

Ser Ala Ile Ser Gly Ser Gly Asp Tyr Thr His Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Val Pro Gly Gly Pro Leu Val Asp Phe Asp Ser Arg Gly
            100                 105                 110

Gln Gly Thr Leu Val Thr Val Ser Ser Glu Ser Lys Tyr Gly Pro Pro
        115                 120                 125

Cys Pro Pro Cys Pro Ala Pro Glu Ala Ala Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser Gln Glu Asp Pro Glu Val
                165                 170                 175

Gln Phe Asn Trp Tyr Val Asp Gly Val Glu Val His Asn Ala Lys Thr
            180                 185                 190

Lys Pro Arg Glu Glu Gln Phe Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Gly Leu Pro Ser Ser Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Gln Glu Glu Met Thr Lys Asn Gln Val Ser Leu Trp Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Arg Leu Thr Val Asp Lys Ser Arg Trp
305                 310                 315                 320
```

Gln Glu Gly Asn Val Phe Ser Cys Ser Val Met His Glu Ala Leu His
325 330 335

Asn His Tyr Thr Gln Lys Ser Leu Ser Leu Ser Leu Gly Lys
340 345 350

<210> SEQ ID NO 26
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 26

Gln Val Gln Leu Val Glu Ser Gly Gly Gly Leu Val Gln Pro Gly Gly
1 5 10 15

Ser Leu Arg Leu Ser Cys Val Ala Ser Gly Phe Thr Phe Ser Ser Asn
20 25 30

Ala Met Ser Trp Val Arg Gln Ala Pro Gly Lys Gly Leu Glu Trp Val
35 40 45

Ser Ala Ile Ser Gly Ser Gly Asp Tyr Thr His Tyr Ser Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Glu Val Pro Gly Gly Pro Leu Val Asp Phe Asp Ser Arg Gly
100 105 110

Gln Gly Thr Leu Val Thr Val Ser Ser Gly Gly Gly Gly Ser Gly Gly
115 120 125

Gly Gly Ser Gln Val Gln Leu Val Glu Ser Gly Gly Gly Leu Val Gln
130 135 140

Pro Gly Gly Ser Leu Arg Leu Ser Cys Val Ala Ser Gly Phe Thr Phe
145 150 155 160

Ser Ser Asn Ala Met Ser Trp Val Arg Gln Ala Pro Gly Lys Gly Leu
165 170 175

Glu Trp Val Ser Ala Ile Ser Gly Ser Gly Asp Tyr Thr His Tyr Ser
180 185 190

Asp Ser Val Lys Gly Arg Phe Thr Ile Ser Arg Asp Asn Ser Lys Asn
195 200 205

Thr Leu Tyr Leu Gln Met Asn Ser Leu Arg Ala Glu Asp Thr Ala Val
210 215 220

Tyr Tyr Cys Ala Lys Glu Val Pro Gly Gly Pro Leu Val Asp Phe Asp
225 230 235 240

Ser Arg Gly Gln Gly Thr Leu Val Thr Val Ser Ser Glu Ser Lys Tyr
245 250 255

Gly Pro Pro Cys Pro Pro Cys Pro Ala Pro Glu Ala Ala Gly Gly Pro
260 265 270

Ser Val Phe Leu Phe Pro Pro Lys Pro Lys Asp Thr Leu Met Ile Ser
275 280 285

Arg Thr Pro Glu Val Thr Cys Val Val Val Asp Val Ser Gln Glu Asp
290 295 300

Pro Glu Val Gln Phe Asn Trp Tyr Val Asp Gly Val Glu Val His Asn
305 310 315 320

```
Ala Lys Thr Lys Pro Arg Glu Glu Gln Phe Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Gly Leu Pro Ser Ser Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Gln Glu Glu Met Thr Lys Asn Gln Val Ser Leu Ser
385                 390                 395                 400

Cys Ala Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Val Ser Arg Leu Thr Val Asp Lys
        435                 440                 445

Ser Arg Trp Gln Glu Gly Asn Val Phe Ser Cys Ser Val Met His Glu
    450                 455                 460

Ala Leu His Asn His Tyr Thr Gln Lys Ser Leu Ser Leu Ser Leu Gly
465                 470                 475                 480

Lys


<210> SEQ ID NO 27
<211> LENGTH: 481
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Gln Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Ser Asn
            20                  25                  30

Ala Met Ser Trp Val Arg Gln Ala Pro Gly Lys Gly Leu Glu Trp Val
        35                  40                  45

Ser Ala Ile Ser Gly Ser Gly Asp Tyr Thr His Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Val Pro Gly Gly Pro Leu Val Asp Phe Asp Ser Arg Gly
            100                 105                 110

Gln Gly Thr Leu Val Thr Val Ser Ser Gly Gly Gly Gly Ser Gly Gly
        115                 120                 125

Gly Gly Ser Gln Val Gln Leu Val Glu Ser Gly Gly Gly Leu Val Gln
    130                 135                 140

Pro Gly Gly Ser Leu Arg Leu Ser Cys Val Ala Ser Gly Phe Thr Phe
145                 150                 155                 160

Ser Ser Asn Ala Met Ser Trp Val Arg Gln Ala Pro Gly Lys Gly Leu
                165                 170                 175

Glu Trp Val Ser Ala Ile Ser Gly Ser Gly Asp Tyr Thr His Tyr Ser
            180                 185                 190
```

```
Asp Ser Val Lys Gly Arg Phe Thr Ile Ser Arg Asp Asn Ser Lys Asn
        195                 200                 205

Thr Leu Tyr Leu Gln Met Asn Ser Leu Arg Ala Glu Asp Thr Ala Val
    210                 215                 220

Tyr Tyr Cys Ala Lys Glu Val Pro Gly Gly Pro Leu Val Asp Phe Asp
225                 230                 235                 240

Ser Arg Gly Gln Gly Thr Leu Val Thr Val Ser Ser Glu Ser Lys Tyr
                245                 250                 255

Gly Pro Pro Cys Pro Pro Cys Pro Ala Pro Glu Ala Ala Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser Gln Glu Asp
    290                 295                 300

Pro Glu Val Gln Phe Asn Trp Tyr Val Asp Gly Val Glu Val His Asn
305                 310                 315                 320

Ala Lys Thr Lys Pro Arg Glu Glu Gln Phe Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Gly Leu Pro Ser Ser Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Gln Glu Glu Met Thr Lys Asn Gln Val Ser Leu Trp
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Arg Leu Thr Val Asp Lys
        435                 440                 445

Ser Arg Trp Gln Glu Gly Asn Val Phe Ser Cys Ser Val Met His Glu
    450                 455                 460

Ala Leu His Asn His Tyr Thr Gln Lys Ser Leu Ser Leu Ser Leu Gly
465                 470                 475                 480

Lys


<210> SEQ ID NO 28
<211> LENGTH: 327
<212> TYPE: PRT
<213> ORGANISM: Homo sapiens

<400> SEQUENCE: 28

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80
```

Tyr Thr Cys Asn Val Asp His Lys Pro Ser Asn Thr Lys Val Asp Lys
85 90 95

Arg Val Glu Ser Lys Tyr Gly Pro Pro Cys Pro Ser Cys Pro Ala Pro
100 105 110

Glu Phe Leu Gly Gly Pro Ser Val Phe Leu Phe Pro Pro Lys Pro Lys
115 120 125

Asp Thr Leu Met Ile Ser Arg Thr Pro Glu Val Thr Cys Val Val Val
130 135 140

Asp Val Ser Gln Glu Asp Pro Glu Val Gln Phe Asn Trp Tyr Val Asp
145 150 155 160

Gly Val Glu Val His Asn Ala Lys Thr Lys Pro Arg Glu Glu Gln Phe
165 170 175

Asn Ser Thr Tyr Arg Val Val Ser Val Leu Thr Val Leu His Gln Asp
180 185 190

Trp Leu Asn Gly Lys Glu Tyr Lys Cys Lys Val Ser Asn Lys Gly Leu
195 200 205

Pro Ser Ser Ile Glu Lys Thr Ile Ser Lys Ala Lys Gly Gln Pro Arg
210 215 220

Glu Pro Gln Val Tyr Thr Leu Pro Pro Ser Gln Glu Glu Met Thr Lys
225 230 235 240

Asn Gln Val Ser Leu Thr Cys Leu Val Lys Gly Phe Tyr Pro Ser Asp
245 250 255

Ile Ala Val Glu Trp Glu Ser Asn Gly Gln Pro Glu Asn Asn Tyr Lys
260 265 270

Thr Thr Pro Pro Val Leu Asp Ser Asp Gly Ser Phe Phe Leu Tyr Ser
275 280 285

Arg Leu Thr Val Asp Lys Ser Arg Trp Gln Glu Gly Asn Val Phe Ser
290 295 300

Cys Ser Val Met His Glu Ala Leu His Asn His Tyr Thr Gln Lys Ser
305 310 315 320

Leu Ser Leu Ser Leu Gly Lys
325

<210> SEQ ID NO 29
<211> LENGTH: 327
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 29

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Lys Thr
65 70 75 80

Tyr Thr Cys Asn Val Asp His Lys Pro Ser Asn Thr Lys Val Asp Lys
85 90 95

```
Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Trp Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 30
<211> LENGTH: 327
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
```

```
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Ser Cys Ala Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Val Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 31
<211> LENGTH: 107
<212> TYPE: PRT
<213> ORGANISM: Homo sapiens

<400> SEQUENCE: 31

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 32
<211> LENGTH: 13
<212> TYPE: PRT
<213> ORGANISM: Homo sapiens

<400> SEQUENCE: 32

Glu Ser Lys Tyr Gly Pro Pro Cys Pro Ser Cys Pro Ala
```

1 5 10

<210> SEQ ID NO 33
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 33

Glu Ser Lys Tyr Gly Pro Pro Cys Pro Pro Cys Pro Ala
1 5 10

<210> SEQ ID NO 34
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 34

Gly Gly Gly Gly Ser
1 5

<210> SEQ ID NO 35
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 35

Gly Gly Gly Gly Ser Gly Gly Gly Gly Ser
1 5 10

<210> SEQ ID NO 36
<211> LENGTH: 110
<212> TYPE: PRT
<213> ORGANISM: Homo sapiens

<400> SEQUENCE: 36

Ala Pro Glu Phe Leu Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser Gln Glu Asp Pro Glu Val Gln Phe Asn Trp Tyr
35 40 45

Val Asp Gly Val Glu Val His Asn Ala Lys Thr Lys Pro Arg Glu Glu
50 55 60

Gln Phe Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Gly Leu Pro Ser Ser Ile Glu Lys Thr Ile Ser Lys Ala Lys
100 105 110

<210> SEQ ID NO 37
<211> LENGTH: 110

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110


<210> SEQ ID NO 38
<211> LENGTH: 107
<212> TYPE: PRT
<213> ORGANISM: Homo sapiens

<400> SEQUENCE: 38

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105


<210> SEQ ID NO 39
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Gly Gln Pro Arg Glu Pro Gln Val Tyr Thr Leu Pro Pro Ser Gln Glu
1               5                   10                  15

Glu Met Thr Lys Asn Gln Val Ser Leu Trp Cys Leu Val Lys Gly Phe
            20                  25                  30

Tyr Pro Ser Asp Ile Ala Val Glu Trp Glu Ser Asn Gly Gln Pro Glu
        35                  40                  45
```

```
Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105


<210> SEQ ID NO 40
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Gly Gln Pro Arg Glu Pro Gln Val Tyr Thr Leu Pro Pro Ser Gln Glu
1               5                   10                  15

Glu Met Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Val Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105


<210> SEQ ID NO 41
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

-continued

```
<210> SEQ ID NO 42
<211> LENGTH: 10
<212> TYPE: PRT
<213> ORGANISM: Homo sapiens

<400> SEQUENCE: 42

Lys Pro Leu Pro Glu Val Thr Asp Glu Tyr
1               5                   10


<210> SEQ ID NO 43
<211> LENGTH: 20
<212> TYPE: PRT
<213> ORGANISM: Homo sapiens

<400> SEQUENCE: 43

Val Glu Lys Glu Ala Leu Lys Lys Ile Ile Glu Asp Gln Gln Glu Ser
1               5                   10                  15

Leu Asn Lys Trp
            20
```

MULTI-SPECIFIC ANTIBODIES BINDING TO BCMA

CROSS REFERENCE TO RELATED APPLICATIONS

This application claims priority benefit of the filing date of U.S. Provisional Patent Application Ser. No. 63/046,477, filed on Jun. 30, 2020, the disclosure of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Sep. 29, 2021, is named 60792_00042W001_(TNO-0025-WO) SL.txt and is 64,812 bytes in size.

FIELD OF THE INVENTION

The present invention concerns multi-specific, human heavy chain antibodies (e.g., UniAbs™) binding to BCMA. The invention further concerns methods of making such antibodies, compositions, including pharmaceutical compositions, comprising such antibodies, and their use to treat disorders that are characterized by the expression of BCMA.

BACKGROUND OF THE INVENTION

B-Cell Maturation Antigen (BCMA)

BCMA, also known as tumor necrosis factor superfamily member 17 (TNFRSF17) (UniProt Q02223), is a cell surface receptor exclusively expressed on plasma cells and plasmablasts. BCMA is a receptor for two ligands in the tumor necrosis factor (TNF) superfamily: APRIL (a proliferation-inducing ligand, also known as TNFSF13; TALL-2 and TRDL-1; the high affinity ligand for BCMA) and B cell activation factor (BAFF) (also known as BLyS; TALL-1; THANK; zTNF4; TNFSF20; and D8Ertd387e; the low affinity ligand for BCMA). APRIL and BAFF are growth factors that bind BCMA and promote survival of plasma cells. BCMA is also highly expressed on malignant plasma cells in human multiple myeloma (MM). Antibodies binding to BCMA are described, for example, in Gras et al., 1995, Int. Immunol. 7:1093-1106, WO200124811 and WO200124812. Anti-BCMA antibodies that cross-react with TACI are described in WO2002/066516. Bispecific antibodies against BCMA and CD3 are described, for example, in US 2013/0156769 A1 and US 2015/0376287 A1. An anti-BCMA antibody-MMAE or -MMAF conjugate has been reported to selectively induce killing of multiple myeloma cells (Tai et al., Blood 2014, 123(20): 3128-38). Ali et al., Blood 2016, 128(13):1688-700, have reported that in a clinical trial (#NCT02215967) chimeric antigen receptor (CAR) T cells targeting BCMA resulted in remission of multiple myeloma in human patients.

Heavy Chain Antibodies

In a conventional IgG antibody, the association of the heavy chain and light chain is due in part to a hydrophobic interaction between the light chain constant region and the CH1 constant domain of the heavy chain. There are additional residues in the heavy chain framework 2 (FR2) and framework 4 (FR4) regions that also contribute to this hydrophobic interaction between the heavy and light chains.

It is known, however, that sera of camelids (sub-order Tylopoda which includes camels, dromedaries and llamas) contain a major type of antibodies composed solely of paired H-chains (heavy-chain only antibodies or UniAbs™). The UniAbs™ of Camelidae (*Camelus dromedarius, Camelus bactrianus, Lama glama, Lama guanaco, Lama* alpaca and *Lama vicugna*) have a unique structure consisting of a single variable domain (VHH), a hinge region and two constant domains (CH2 and CH3), which are highly homologous to the CH2 and CH3 domains of classical antibodies. These UniAbs™ lack the first domain of the constant region (CH1) which is present in the genome, but is spliced out during mRNA processing. The absence of the CH1 domain explains the absence of the light chain in the UniAbs™, since this domain is the anchoring place for the constant domain of the light chain. Such UniAbs™ naturally evolved to confer antigen-binding specificity and high affinity by three CDRs from conventional antibodies or fragments thereof (Muyldermans, 2001*; J Biotechnol* 74:277-302; Revets et al., 2005. *Expert Opin Biol Ther* 5:111-124). Cartilaginous fish, such as sharks, have also evolved a distinctive type of immunoglobulin, designated as IgNAR, which lacks the light polypeptide chains and is composed entirely by heavy chains. IgNAR molecules can be manipulated by molecular engineering to produce the variable domain of a single heavy chain polypeptide (vNARs) (Nuttall et al. *Eur. J. Biochem.* 270, 3543-3554 (2003); Nuttall et al. *Function and Bioinformatics* 55, 187-197 (2004); Dooley et al., *Molecular Immunology* 40, 25-33 (2003)).

The ability of heavy chain-only antibodies devoid of light chain to bind antigen was established in the 1960s (Jaton et al. (1968) *Biochemistry,* 7, 4185-4195). Heavy chain immunoglobulin physically separated from light chain retained 80% of antigen-binding activity relative to the tetrameric antibody. Sitia et al. (1990) *Cell,* 60, 781-790 demonstrated that removal of the CH1 domain from a rearranged mouse p gene results in the production of a heavy chain-only antibody, devoid of light chain, in mammalian cell culture. The antibodies produced retained VH binding specificity and effector functions.

Heavy chain antibodies with a high specificity and affinity can be generated against a variety of antigens through immunization (van der Linden, R. H., et al. *Biochim. Biophys. Acta.* 1431, 37-46 (1999)) and the VHH portion can be readily cloned and expressed in yeast (Frenken, L. G. J., et al. *J. Biotechnol.* 78, 11-21(2000)). Their levels of expression, solubility and stability are significantly higher than those of classical F(ab) or Fv fragments (Ghahroudi, M. A. et al. *FEBS Lett.* 414, 521-526 (1997)).

Mice in which the λ (lambda) light (L) chain locus and/or the λ and κ (kappa) L chain loci have been functionally silenced and antibodies produced by such mice are described in U.S. Pat. Nos. 7,541,513 and 8,367,888. Recombinant production of heavy chain-only antibodies in mice and rats has been reported, for example, in WO2006008548; U.S. Application Publication No. 20100122358; Nguyen et al., 2003, *Immunology;* 109(1), 93-101; Brüggemann et al., *Crit. Rev. Immunol.:* 2006, 26(5):377-90; and Zou et al., 2007*, J Exp Med;* 204(13): 3271-3283. The production of knockout rats via embryo microinjections of zinc-finger nucleases is described in Geurts et al., 2009, *Science,* 325(5939):433. Soluble heavy chain-only antibodies and transgenic rodents comprising a heterologous heavy chain locus producing such antibodies are described in U.S. Pat. Nos. 8,883,150 and 9,365,655. CAR-T structures comprising single-domain antibodies as binding (targeting) domain are described, for example, in Iri-Sofla et al., 2011, *Experimental Cell Research* 317:2630-2641 and Jamnani et al., 2014, *Biochim Biophys Acia,* 1840:378-386.

SUMMARY OF THE INVENTION

Aspects of the invention relate to antibodies, such as heavy chain antibodies, including, but not limited to, UniAbs™, that bind to BCMA. Further aspects of the invention relate to methods of making such antibodies, compositions comprising such antibodies, and their use in the treatment of B-cell disorders that are characterized by the expression of BCMA.

Aspects of the invention include multi-specific antibodies that bind to BCMA, comprising a first binding unit comprising a variable region comprising a CDR3 sequence having at least 85% sequence identity to SEQ ID NO: 3.

Aspects of the invention include multi-specific antibodies that bind to BCMA, comprising a first binding unit comprising a variable region comprising a CDR1 sequence, a CDR2 sequence, and a CDR3 sequence, wherein the CDR1, CDR2 and CDR3 sequences combined have at least 85% sequence identity to SEQ ID NOs: 1-3 combined.

Aspects of the invention include multi-specific antibodies that bind to BCMA, comprising a first binding unit comprising a variable region comprising: a CDR1 sequence comprising the sequence of SEQ ID NO: 1; a CDR2 sequence comprising the sequence of SEQ ID NO: 2; and a CDR3 sequence comprising the sequence of SEQ ID NO: 3.

In some embodiments, the CDR1, CDR2 and CDR3 sequences are present in a human VH framework. In some embodiments, the variable region is a heavy chain-only variable region. In some embodiments, the variable region comprises a sequence having at least 95% sequence identity to SEQ ID NO: 12. In some embodiments, the variable region comprises a sequence comprising SEQ ID NO: 12. In some embodiments, the variable region is in a monovalent or bivalent configuration.

In some embodiments, a multi-specific antibody further comprises a heavy chain constant region sequence, in the absence of a CH1 sequence. In some embodiments, a heavy chain constant region sequence comprises a CH2 domain and a CH3 domain, but no CH1 domain. In some embodiments, the CH2 domain comprises the sequence of a wild type human IgG4 CH2 domain (SEQ ID NO: 36).

In some embodiments, the CH2 domain comprises a variant human IgG4 CH2 domain comprising an F234A mutation, an L235A mutation, or both an F234A mutation and an L235A mutation. In some embodiments, the CH3 domain comprises the sequence of a wild type human IgG4 CH3 domain (SEQ ID NO: 38). In some embodiments, the CH3 domain comprises a variant human IgG4 CH3 domain comprising a T366W mutation (SEQ ID NO: 39). In some embodiments, the CH3 domain comprises a variant human IgG4 CH3 domain comprising a T366S mutation, an L368A mutation, and a Y407V mutation (SEQ ID NO: 40).

In some embodiments, a multi-specific antibody further comprises a hinge region sequence positioned between the heavy chain-only variable region and the CH2 domain. In some embodiments, the hinge region sequence comprises the sequence of a wild type human IgG4 hinge region (SEQ ID NO: 32). In some embodiments, the hinge region sequence comprises a variant human IgG4 hinge region sequence comprising an S228P mutation (SEQ ID NO: 33).

In some embodiments, a multi-specific antibody further comprises a variant human IgG4 CH2 domain comprising an F234A mutation and an L235A mutation. In some embodiments, a multi-specific antibody further comprises a variant human IgG4 CH3 domain comprising a T366W mutation. In some embodiments, a multi-specific antibody further comprises a variant human IgG4 CH3 domain comprising a T366S mutation, an L368A mutation, and a Y407V mutation.

In some embodiments, a multi-specific antibody further comprises a second binding unit that binds to La protein. In some embodiments, the second binding unit comprises: (a) a heavy chain variable region comprising: (i) a CDR1 sequence comprising any one of the sequences of SEQ ID NOs: 4 or 7; and (ii) a CDR2 sequence comprising the sequence of SEQ ID NO: 5; and (iii) a CDR3 sequence comprising any one of the sequences of SEQ ID NOs: 6 or 8; and (b) a light chain variable region comprising: (i) a CDR1 sequence comprising the sequence of SEQ ID NO: 9; and (ii) a CDR2 sequence comprising the sequence of SEQ ID NO: 10; and (iii) a CDR3 sequence comprising the sequence of SEQ ID NO: 11.

In some embodiments, the heavy chain variable region of the second binding unit comprises: (i) a CDR1 sequence comprising the sequence of SEQ ID NO: 4, a CDR2 sequence comprising the sequence of SEQ ID NO: 5, and a CDR3 sequence comprising the sequence of SEQ ID NO: 6; or (i) a CDR1 sequence comprising the sequence of SEQ ID NO: 7, a CDR2 sequence comprising the sequence of SEQ ID NO: 5, and a CDR3 sequence comprising the sequence of SEQ ID NO: 8.

In some embodiments, the CDR1, CDR2 and CDR3 sequences of the heavy chain variable region of the second binding unit are present in a human VH framework. In some embodiments, the CDR1, CDR2 and CDR3 sequences of the light chain variable region of the second binding unit are present in a human VL framework. In some embodiments, the human VL framework is a human Vkappa framework. In some embodiments, the human VL framework is a human Vlambda framework.

In some embodiments, the second binding unit comprises a heavy chain variable region comprising a sequence having at least 95% sequence identity to SEQ ID NO: 14 and a light chain variable region comprising a sequence having at least 95% sequence identity to SEQ ID NO: 16. In some embodiments, the second binding unit comprises a heavy chain variable region comprising the sequence of SEQ ID NO: 14 and a light chain variable region comprising the sequence of SEQ ID NO: 16. In some embodiments, the second binding unit comprises a heavy chain variable region comprising a sequence having at least 95% sequence identity to SEQ ID NO: 15 and a light chain variable region comprising a sequence having at least 95% sequence identity to SEQ ID NO: 17. In some embodiments, the second binding unit comprises a heavy chain variable region comprising the sequence of SEQ ID NO: 15 and a light chain variable region comprising the sequence of SEQ ID NO: 17.

In some embodiments, the heavy chain variable region and the light chain variable region of the second binding unit are on a common polypeptide subunit of the multi-specific antibody, and are connected by a linker sequence. In some embodiments, the heavy chain variable region and the light chain variable region of the second binding unit are on different polypeptide subunits of the multi-specific antibody.

In some embodiments, the second binding unit further comprises a heavy chain constant region. In some embodiments, the heavy chain constant region comprises a CH1 domain, a hinge region, a CH2 domain, and a CH3 domain. In some embodiments, the CH2 domain comprises the sequence of a wild type human IgG4 CH2 domain (SEQ ID NO: 36). In some embodiments, the CH2 domain comprises a variant human IgG4 CH2 domain comprising an F234A mutation, an L235A mutation, or both an F234A mutation and an L235A mutation. In some embodiments, the CH3 domain comprises the sequence of a wild type human IgG4 CH3 domain (SEQ ID NO: 38). In some embodiments, the CH3 domain comprises a variant human IgG4 CH3 domain comprising a T366W mutation (SEQ ID NO: 39). In some embodiments, the CH3 domain comprises a variant human IgG4 CH3 domain comprising a T366S mutation, an L368A mutation, and a Y407V mutation (SEQ ID NO: 40). In some embodiments, the hinge region comprises the sequence of a wild type human IgG4 hinge region (SEQ ID NO: 32). In some embodiments, the hinge region comprises a variant human IgG4 hinge region sequence comprising an S228P mutation (SEQ ID NO: 33).

In some embodiments, a multi-specific antibody further comprises a variant human IgG4 CH2 domain comprising an F234A mutation and an L235A mutation. In some embodiments, a multi-specific antibody further comprises a variant human IgG4 CH3 domain comprising a T366W mutation. In some embodiments, a multi-specific antibody further comprises a variant human IgG4 CH3 domain comprising a T366S mutation, an L368A mutation, and a Y407V mutation.

In some embodiments, the second binding unit further comprises a light chain constant region. In some embodiments, the light chain constant region comprises a human Vkappa constant region sequence. In some embodiments, the light chain constant region comprises a human Vlambda constant region sequence. In some embodiments, the multi-specific antibody is bispecific.

Aspects of the invention include multi-specific antibodies comprising: (a) a first binding unit that binds to La protein, comprising: (i) a heavy chain variable region comprising: a CDR1 sequence of SEQ ID NOs: 4 or 7, a CDR2 sequence of SEQ ID NO: 5, and a CDR3 sequence of SEQ ID NO: 6 or 8, in a human VH framework, and (ii) a light chain variable region comprising: a CDR1 sequence of SEQ ID NO: 9, a CDR2 sequence of SEQ ID NO: 10, and a CDR3 sequence of SEQ ID NO: 11, in a human VL framework; and (b) a second binding unit that binds to BCMA, comprising: (i) an antigen-binding domain of an anti-BCMA heavy chain-only antibody, comprising a CDR1 sequence of SEQ ID NO: 1, a CDR2 sequence of SEQ ID NO: 2, and a CDR3 sequence of SEQ ID NO: 3, in a human VH framework, wherein the antigen-binding domain of the anti-BCMA heavy chain-only antibody is in a monovalent or bivalent configuration.

In some embodiments, the heavy chain variable region and the light chain variable region of the first binding unit are on a common polypeptide subunit of the multi-specific antibody, and are connected by a linker sequence. In some embodiments, the heavy chain variable region and the light chain variable region of the first binding unit are on different polypeptide subunits of the multi-specific antibody.

In some embodiments, the heavy chain variable region of the first binding unit comprises: (i) a CDR1 sequence of SEQ ID NO: 4, a CDR2 sequence of SEQ ID NO: 5, and a CDR3 sequence of SEQ ID NO: 6; or (ii) a CDR1 sequence of SEQ ID NO: 7, a CDR2 sequence of SEQ ID NO: 5, and a CDR3 sequence of SEQ ID NO: 8. In some embodiments, the human VL framework is a human Vkappa framework. In some embodiments, the human VL framework is a human Vlambda framework. In some embodiments, the heavy chain variable region of the first binding unit comprises a sequence having at least 95% identity to SEQ ID NO: 14 or SEQ ID NO: 15. In some embodiments, the heavy chain variable region of the first binding unit comprises the sequence of SEQ ID NO: 14 or SEQ ID NO: 15. In some embodiments, the light chain variable region of the first binding unit comprises a sequence having at least 95% identity to SEQ ID NO: 16 or SEQ ID NO: 17. In some embodiments, the light chain variable region of the first binding unit comprises the sequence of SEQ ID NO: 16 or SEQ ID NO: 17. In some embodiments, the antigen-binding domain of the anti-BCMA heavy chain-only antibody comprises a variable region sequence having at least 95% identity to the sequence of SEQ ID NO: 12. In some embodiments, the antigen-binding domain of the anti-BCMA heavy chain-only antibody comprises a variable region sequence comprising the sequence of SEQ ID NO: 12.

In some embodiments, the antigen-binding domain of the anti-BCMA heavy chain-only antibody is in a bivalent configuration, and comprises a linker sequence. In some embodiments, the linker sequence comprises a G4S linker sequence (SEO ID NO: 34).

In some embodiments, the first binding unit further comprises a heavy chain constant region. In some embodiments, the heavy chain constant region comprises a CH1 domain, a hinge region, a CH2 domain, and a CH3 domain. In some embodiments, the CH2 domain comprises the sequence of a wild type human IgG4 CH2 domain (SEQ ID NO: 36). In some embodiments, the CH2 domain comprises a variant human IgG4 CH2 domain comprising an F234A mutation, an L235A mutation, or both an F234A mutation and an L235A mutation. In some embodiments, the CH3 domain comprises the sequence of a wild type human IgG4 CH3 domain (SEQ ID NO: 38). In some embodiments, the CH3 domain comprises a variant human IgG4 CH3 domain comprising a T366W mutation (SEQ ID NO: 39). In some embodiments, the CH3 domain comprises a variant human IgG4 CH3 domain comprising a T366S mutation, an L368A mutation, and a Y407V mutation (SEQ ID NO: 40). In some embodiments, the hinge region comprises the sequence of a wild type human IgG4 hinge region (SEQ ID NO: 32). In some embodiments, the hinge region comprises a variant human IgG4 hinge region sequence comprising an S228P mutation (SEQ ID NO: 33).

In some embodiments, a multi-specific antibody further comprises a variant human IgG4 CH2 domain comprising an F234A mutation and an L235A mutation. In some embodiments, a multi-specific antibody further comprises a variant human IgG4 CH3 domain comprising a T366W mutation. In some embodiments, a multi-specific antibody further comprises a variant human IgG4 CH3 domain comprising a T366S mutation, an L368A mutation, and a Y407V mutation.

In some embodiments, the first binding unit further comprises a light chain constant region. In some embodiments, the light chain constant region comprises a human Vkappa constant region sequence. In some embodiments, the light chain constant region comprises a human Vlambda constant region sequence.

In some embodiments, the second binding unit further comprises a heavy chain constant region sequence, in the absence of a CH1 sequence. In some embodiments, the heavy chain constant region sequence comprises a CH2 domain and a CH3 domain, but no CH1 domain. In some embodiments, the CH2 domain comprises the sequence of a wild type human IgG4 CH2 domain (SEQ ID NO: 36). In some embodiments, the CH2 domain comprises a variant human IgG4 CH2 domain comprising an F234A mutation, an L235A mutation, or both an F234A mutation and an L235A mutation. In some embodiments, the CH3 domain comprises the sequence of a wild type human IgG4 CH3 domain (SEQ ID NO: 38). In some embodiments, the CH3 domain comprises a variant human IgG4 CH3 domain comprising a T366W mutation (SEQ ID NO: 39). In some embodiments, the CH3 domain comprises a variant human IgG4 CH3 domain comprising a T366S mutation, an L368A mutation, and a Y407V mutation (SEQ ID NO: 40). In some embodiments, the hinge region comprises the sequence of a wild type human IgG4 hinge region (SEQ ID NO: 32). In some embodiments, the hinge region comprises a variant human IgG4 hinge region sequence comprising an S228P mutation (SEQ ID NO: 33).

In some embodiments, a multi-specific antibody further comprises a variant human IgG4 CH2 domain comprising an F234A mutation and an L235A mutation. In some embodiments, a multi-specific antibody further comprises a variant human IgG4 CH3 domain comprising a T366W mutation. In some embodiments, a multi-specific antibody further comprises a variant human IgG4 CH3 domain comprising a T366S mutation, an L368A mutation, and a Y407V mutation. In some embodiments, the multi-specific antibody is bispecific.

Aspects of the invention include bispecific three-chain antibody-like molecules that bind to BCMA and La protein, comprising: (a) a first heavy chain polypeptide subunit comprising the sequence of SEQ ID NO: 18; (b) a second heavy chain polypeptide subunit comprising the sequence of SEQ ID NO: 24; and (c) a first light chain polypeptide subunit comprising the sequence of SEQ ID NO: 20.

Aspects of the invention include bispecific three-chain antibody-like molecules that bind to BCMA and La protein, comprising: (a) a first heavy chain polypeptide subunit comprising the sequence of SEQ ID NO: 18; (b) a second heavy chain polypeptide subunit comprising the sequence of SEQ ID NO: 26; and (c) a first light chain polypeptide subunit comprising the sequence of SEQ ID NO: 20.

Aspects of the invention include bispecific three-chain antibody-like molecules that bind to BCMA and La protein, comprising: (a) a first heavy chain polypeptide subunit comprising the sequence of SEQ ID NO: 21; (b) a second heavy chain polypeptide subunit comprising the sequence of SEQ ID NO: 24; and (c) a first light chain polypeptide subunit comprising the sequence of SEQ ID NO: 23.

Aspects of the invention include bispecific three-chain antibody-like molecules that bind to BCMA and La protein, comprising: (a) a first heavy chain polypeptide subunit comprising the sequence of SEQ ID NO: 21; (b) a second heavy chain polypeptide subunit comprising the sequence of SEQ ID NO: 26; and (c) a first light chain polypeptide subunit comprising the sequence of SEQ ID NO: 23.

Aspects of the invention include bispecific three-chain antibody-like molecules that bind to BCMA and La protein, comprising: (a) a first heavy chain polypeptide subunit comprising the sequence of SEQ ID NO: 19: (b) a second heavy chain polypeptide subunit comprising the sequence of SEQ ID NO: 25; and (c) a first light chain polypeptide subunit comprising the sequence of SEQ ID NO: 20.

Aspects of the invention include bispecific three-chain antibody-like molecules that bind to BCMA and La protein, comprising: (a) a first heavy chain polypeptide subunit comprising the sequence of SEQ ID NO: 19; (b) a second heavy chain polypeptide subunit comprising the sequence of SEQ ID NO: 27; and (c) a first light chain polypeptide subunit comprising the sequence of SEQ ID NO: 20.

Aspects of the invention include bispecific three-chain antibody-like molecules that bind to BCMA and La protein, comprising: (a) a first heavy chain polypeptide subunit comprising the sequence of SEQ ID NO: 22; (b) a second heavy chain polypeptide subunit comprising the sequence of SEQ ID NO: 25; and (c) a first light chain polypeptide subunit comprising the sequence of SEQ ID NO: 23.

Aspects of the invention include bispecific three-chain antibody-like molecules that bind to BCMA and La protein, comprising: (a) a first heavy chain polypeptide subunit comprising the sequence of SEQ ID NO: 22; (b) a second heavy chain polypeptide subunit comprising the sequence of SEQ ID NO: 27; and (c) a first light chain polypeptide subunit comprising the sequence of SEQ ID NO: 23.

Aspects of the invention include pharmaceutical compositions comprising an antibody as described herein.

Aspects of the invention include methods for the treatment of a B-cell disorder characterized by expression of BCMA, comprising administering to a subject with said disorder an antibody or a pharmaceutical composition as described herein.

Aspects of the invention include use of an antibody as described herein in the preparation of a medicament for the treatment of a B-cell disorder characterized by expression of BCMA.

Aspects of the invention include an antibody as described herein for use in the treatment of a B-cell disorder characterized by expression of BCMA.

In some embodiments, the disorder is multiple myeloma (MM). In some embodiments, the disorder is an autoimmune disorder. In some embodiments, the autoimmune disorder is systemic lupus erythematosus (SLE). In some embodiments, the autoimmune disorder is rheumatoid arthritis (RA). In some embodiments, the autoimmune disorder is multiple sclerosis (MS).

Aspects of the invention include a polynucleotide encoding an antibody as described herein. A vector comprising a polynucleotide as described herein, and a cell comprising a vector as described herein.

Aspects of the invention include methods of producing an antibody as described herein, comprising growing a cell as described herein under conditions permissive for expression of the antibody, and isolating the antibody from the cell.

Aspects of the invention include methods of making an antibody as described herein, comprising immunizing a UniRat animal with BCMA and identifying BCMA-binding heavy chain sequences.

Aspects of the invention include methods of treatment, comprising administering to an individual in need an effective dose of an antibody or pharmaceutical composition as described herein.

These and further aspects will be further explained in the rest of the disclosure, including the Examples.

BRIEF DESCRIPTION OF THE DRAWINGS

FIGS. 1-6 are tables providing the amino acid sequences of the indicated proteins.

FIG. 7, Panel A, is a schematic illustration of a three-chain antibody-like molecule comprising three polypeptide subunits. A first binding unit is formed from the first light chain polypeptide subunit and the first heavy chain polypeptide subunit. The second heavy chain polypeptide comprises a heavy chain-only variable region domain in a bivalent configuration, which provides a second binding unit.

FIG. 7, Panel B, is a schematic illustration of a three-chain antibody-like molecule comprising three polypeptide subunits. A first binding unit is formed from the first light chain polypeptide subunit and the first heavy chain polypeptide subunit. The second heavy chain polypeptide comprises a heavy chain-only variable region domain in a monovalent configuration, which provides a second binding unit.

FIG. 8, Panel A is a schematic diagram of a CAR-T structure comprising an anti-BCMA extracellular binding domain, as described herein.

FIG. 8, Panel B is a graph showing antigen-specific binding and activation of CAR constructs comprising an anti-BCMA extracellular binding domain, as described herein, tested in the indicated cell lines.

FIG. 9, Panel A is a graph showing mean fluorescence intensity (MFI) for test antibodies binding to MM1.S cells.

FIG. 9, Panel B is a graph showing mean fluorescence intensity (MFI) for test antibodies binding to H929 cells.

FIG. 10, Panel A is a graph showing A450-A570 values indicating AntiX**BCMA_F7E binding to BCMA in the presence of BCMA agonist, APRIL.

FIG. 10, Panel B is a graph showing A450-A570 values indicating AntiX**BCMA_F7E_F7E binding to BCMA in the presence of BCMA agonist, APRIL.

FIG. 10, Panel C is a graph showing A450-A570 values indicating AntiX**GP120_F8A binding to BCMA in the presence of BCMA agonist, APRIL.

DETAILED DESCRIPTION OF THE PREFERRED EMBODIMENTS

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001); Harlow. Lane and Harlow, Using Antibodies: A Laboratory Manual: Portable Protocol No. I, Cold Spring Harbor Laboratory (1998); and Harlow and Lane, Antibodies: A Laboratory Manual, Cold Spring Harbor Laboratory; (1988).

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless indicated otherwise, antibody residues herein are numbered according to the Kabat numbering system (e.g., Kabat et al., Sequences of Immunological Interest. 5th Ed. Public Health Service, National Institutes of Health, Bethesda, Md. (1991)).

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

All references cited throughout the disclosure, including patent applications and publications, are incorporated by reference herein in their entirety.

I. DEFINITIONS

By "comprising" it is meant that the recited elements are required in the composition/method/kit, but other elements may be included to form the composition/method/kit etc. within the scope of the claim.

By "consisting essentially of", it is meant a limitation of the scope of composition or method described to the specified materials or steps that do not materially affect the basic and novel characteristic(s) of the subject invention.

By "consisting of", it is meant the exclusion from the composition, method, or kit of any element, step, or ingredient not specified in the claim.

Antibody residues herein are numbered according to the Kabat numbering system and the EU numbering system. The Kabat numbering system is generally used when referring to a residue in the variable domain (approximately residues 1-113 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies mean residue numbering by the Kabat numbering system. Unless stated otherwise herein, references to residue numbers in the constant domain of antibodies mean residue numbering by the EU numbering system.

Antibodies, also referred to as immunoglobulins, conventionally comprise at least one heavy chain and one light chain, where the amino terminal domain of the heavy and light chains is variable in sequence, hence is commonly referred to as a variable region domain, or a variable heavy (VH) or variable light (VL) domain. The two domains conventionally associate to form a specific binding region, although as will be discussed here, specific binding can also be obtained with heavy chain-only variable sequences, and a variety of non-natural configurations of antibodies are known and used in the art.

A "functional" or "biologically active" antibody or antigen-binding molecule (including heavy chain-only antibodies and multi-specific (e.g., bispecific) three-chain antibody-like molecules (TCAs), described herein) is one capable of exerting one or more of its natural activities in structural, regulatory, biochemical or biophysical events. For example, a functional antibody or other binding molecule, e.g., a TCA, may have the ability to specifically bind an antigen and the binding may in turn elicit or alter a cellular or molecular event such as signal transduction or enzymatic activity. A functional antibody or other binding molecule, e.g., a TCA, may also block ligand activation of a receptor or act as an agonist or antagonist. The capability of an antibody or other binding molecule, e.g., a TCA, to exert one or more of its natural activities depends on several factors, including proper folding and assembly of the polypeptide chains.

The term "antibody" herein is used in the broadest sense and specifically covers monoclonal antibodies, polyclonal antibodies, monomers, dimers, multimers, multi-specific antibodies (e.g., bispecific antibodies), heavy chain-only antibodies, three chain antibodies, three-chain antibody-like molecules (TCAs), single chain Fv (scFv), nanobodies, etc., and also includes antibody fragments, so long as they exhibit the desired biological activity (Miller et al (2003) Jour. of Immunology 170:4854-4861). Antibodies may be murine, human, humanized, chimeric, or derived from other species.

The term antibody may reference a full-length heavy chain, a full length light chain, an intact immunoglobulin molecule, or an immunologically active portion of any of these polypeptide subunits, i.e., a polypeptide that comprises an antigen binding site that immunospecifically binds an antigen of a target of interest or part thereof, such targets including, but not limited to, a cancer cell, or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule, including engineered subclasses with altered Fc portions that provide for reduced or enhanced effector cell activity. Light chains of the subject antibodies can be kappa light chains (Vkappa) or lambda light chains (Vlambda). The immunoglobulins can be derived from any species. In one aspect, the immunoglobulin is of largely human origin.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. Monoclonal antibodies in accordance with the present invention can be made by the hybridoma method first described by Kohler et al. (1975) *Nature* 256:495, and can also be made via recombinant protein production methods (see, e.g., U.S. Pat. No. 4,816,567), for example.

The term "variable", as used in connection with antibodies, refers to the fact that certain portions of the antibody variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, MD. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g., residues 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, MD. (1991)) and/or those residues from a "hypervariable loop" residues 26-32 (H1), 53-55 (H2) and 96-101 (H3) in the heavy chain variable domain; Chothia and Lesk *J. Mol. Biol.* 196:901-917 (1987)).

The terms "CDR", and its plural "CDRs", refer to a complementarity determining region (CDR) of which three make up the binding character of a light chain variable region (CDRL1, CDRL2 and CDRL3) and three make up the binding character of a heavy chain variable region (CDRH1, CDRH2 and CDRH3). CDRs contribute to the functional activity of an antibody molecule and are separated by amino acid sequences that comprise scaffolding or framework regions. The exact definitional CDR boundaries and lengths are subject to different classification and numbering systems.

Exemplary CDR designations are shown herein, however, one of skill in the art will understand that a number of definitions of the CDRs are commonly in use, including the Kabat definition (see "Zhao et al. A germline knowledge based computational approach for determining antibody complementarity determining regions." *Mol Immunol.* 2010; 47:694-700), which is based on sequence variability and is the most commonly used. The Chothia definition is based on the location of the structural loop regions (Chothia et al. "Conformations of immunoglobulin hypervariable regions." *Nature.* 1989; 342:877-883). Alternative CDR definitions of interest include, without limitation, those disclosed by Honegger, "Yet another numbering scheme for immunoglobulin variable domains: an automatic modeling and analysis tool." *J Mol Biol.* 2001; 309:657-670; Ofran et al. "Automated identification of complementarity determining regions (CDRs) reveals peculiar characteristics of CDRs and B cell epitopes." *J Immunol.* 2008:181:6230-6235; Almagro "Identification of differences in the specificity-determining residues of antibodies that recognize antigens of different size: implications for the rational design of antibody repertoires." *J Mol Recognit.* 2004; 17:132-143; and Padlan et al. "Identification of specificity-determining residues in antibodies." *Faseb J.* 1995; 9:133-139., each of which is herein specifically incorporated by reference.

In one particular embodiment, "CDR" means a complementarity determining region of an antibody as defined in Lefranc, M P et al., IMGT, the international ImMunoGeneTics database, *Nucleic Acids Res.,* 27:209-212 (1999).

"Framework Region" or "FR" residues are those variable domain residues other than the hypervariable region/CDR residues as herein defined.

The terms "heavy chain-only antibody," and "heavy-chain antibody" are used interchangeably herein and refer, in the broadest sense, to antibodies lacking the light chain of a conventional antibody. The terms specifically include, without limitation, homodimeric antibodies comprising the VH antigen-binding domain and the CH2 and CH3 constant domains, in the absence of the CH1 domain; functional (antigen-binding) variants of such antibodies, soluble VH variants, Ig-NAR comprising a homodimer of one variable domain (V-NAR) and five C-like constant domains (C-NAR) and functional fragments thereof; and soluble single domain antibodies (sUniDabs™). In one embodiment, a heavy chain-only antibody is composed of the variable region antigen-binding domain composed of framework 1, CDR1, framework 2, CDR2, framework 3. CDR3, and framework 4. In another embodiment, the heavy chain-only antibody is composed of an antigen-binding domain, at least part of a hinge region and CH2 and CH3 domains, in the absence of a CH1 domain. In another embodiment, the heavy chain-only antibody is composed of an antigen-binding domain, at least part of a hinge region, and a CH2 domain. In a further embodiment, the heavy chain-only antibody is composed of an antigen-binding domain, at least part of a hinge region, and a CH3 domain. Heavy chain-only antibodies in which the CH2 and/or CH3 domain is truncated are also included herein. In a further embodiment, the heavy chain-only antibody is composed of an antigen binding domain, and at least one CH (CH1, CH2, CH3, or CH4) domain, but no hinge region. In a further embodiment, the heavy chain-only antibody is composed of an antigen binding domain, at least one CH (CH1, CH2, CH3, or CH4) domain, and at least a portion of a hinge region. The heavy chain-only antibody can be in the form of a dimer, in which two heavy chains are disulfide bonded or otherwise, covalently or non-covalently, attached with each other. The heavy chain-only antibody may belong to the IgG subclass, but antibodies belonging to other subclasses, such as IgM, IgA, IgD and IgE subclass, are also included herein. In a particular embodiment, the heavy-chain antibody is of the IgG1, IgG2, IgG3, or IgG4 subtype, in particular the IgG1 or IgG4 subtype. In one embodiment, the heavy-chain antibody is of the IgG4 subtype, wherein one or more of the CH domains are modified to alter an effector function of the antibody. In one embodiment, the heavy-chain antibody is of the IgG1 subtype, wherein one or more of the CH domains are modified to alter an effector function of the antibody. Modifications of CH domains that alter effector function are further described herein. Non-limiting examples of heavy-chain antibodies are described, for example, in WO2018/039180, the disclosure of which is incorporated herein by reference in its entirety.

In some embodiments, the antibodies herein (e.g., heavy-chain only antibodies) are used as a binding (targeting) domain of a chimeric antigen receptor (CAR). The definition specifically includes human heavy chain-only antibodies produced by human immunoglobulin transgenic rats (UniRat™), called UniAbs™. The variable regions (VH) of UniAbs™ are called UniDabs™, and are versatile building blocks that can be linked to Fc regions or serum albumin for the development of novel therapeutics with multi-specificity, increased potency and extended half-life. Since the homodimeric UniAbs™ lack a light chain and thus a VL domain, the antigen is recognized by one single domain, i.e., the variable domain (antigen-binding domain) of the heavy chain of a heavy-chain antibody (VH or VHH). In some embodiments, the antibodies herein are multi-specific (e.g., bispecific), comprising a first binding unit with binding affinity for a first antigen of interest (e.g., an antigen on a target cell, e.g., BCMA) and a second binding unit with binding affinity for a second antigen of interest (e.g., an antigen on a universal chimeric antigen receptor (CAR) complex). As such, in some embodiments, the antibodies described herein can functionalize a universal CAR complex by providing binding affinity to a particular antigenic target (e.g., BCMA).

An "intact antibody chain" as used herein is one comprising a full length variable region and a full length constant region (Fc). An intact "conventional" antibody comprises an intact light chain and an intact heavy chain, as well as a light chain constant domain (CL) and heavy chain constant domains, CH1, hinge, CH2 and CH3 for secreted IgG. Other isotypes, such as IgM or IgA may have different CH domains. The constant domains may be native sequence constant domains (e.g., human native sequence constant domains) or amino acid sequence variants thereof. The intact antibody may have one or more "effector functions" which refer to those biological activities attributable to the Fc constant region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors. Constant region variants include those that alter the effector profile, binding to Fc receptors, and the like.

Depending on the amino acid sequence of the Fc (constant domain) of their heavy chains, antibodies and various antigen-binding proteins can be provided as different classes. There are five major classes of heavy chain Fc regions: IgA, IgD, IgE, IgG, and IgM, and several of these may be further divided into "subclasses" (isotypes), e.g., IgG1, IgG2, IgG3, IgG4, IgA, and IgA2. The Fc constant domains that correspond to the different classes of antibodies may be referenced as α, δ, ε, γ, and μ, respectively. The subunit structures and three-dimensional configurations of different classes of immunoglobulins are well known. Ig forms include hinge-modifications or hingeless forms (Roux et al (1998) J. Immunol. 161:4083-4090; Lund et al (2000) Eur. J. Biochem. 267:7246-7256; US 2005/0048572; US 2004/0229310). The light chains of antibodies from any vertebrate species can be assigned to one of two types, called κ (kappa) and λ (lambda), based on the amino acid sequences of their constant domains. Antibodies in accordance with embodiments of the invention can comprise kappa light chain sequences or lambda light chain sequences.

A "functional Fc region" possesses an "effector function" of a native-sequence Fc region. Non-limiting examples of effector functions include C1q binding; CDC; Fc-receptor binding; ADCC; ADCP; down-regulation of cell-surface receptors (e.g., B-cell receptor), etc. Such effector functions generally require the Fc region to interact with a receptor, e.g., the FcγRI; FcγRIIA; FcγRIIB1; FcγRIIB2: FcγRIIIA; FcγRIIIB receptors, and the low affinity FcRn receptor; and can be assessed using various assays known in the art. A "dead" or "silenced" Fc is one that has been mutated to retain activity with respect to, for example, prolonging serum half-life, but which does not activate a high affinity Fc receptor, or which has a reduced affinity to an Fc receptor.

A "native-sequence Fc region" comprises an amino acid sequence identical to the amino acid sequence of an Fc region found in nature. Native-sequence human Fc regions include, for example, a native-sequence human IgG1 Fc region (non-A and A allotypes); native-sequence human IgG2 Fc region; native-sequence human IgG3 Fc region; and native-sequence human IgG4 Fc region, as well as naturally occurring variants thereof.

A "variant Fc region" comprises an amino acid sequence that differs from that of a native-sequence Fc region by virtue of at least one amino acid modification, preferably one or more amino acid substitution(s). Preferably, the variant Fc region has at least one amino acid substitution compared to a native-sequence Fc region or to the Fc region of a parent polypeptide, e.g., from about one to about ten amino acid substitutions, and preferably from about one to about five amino acid substitutions in a native-sequence Fc region or in the Fc region of the parent polypeptide. The variant Fc region herein will preferably possess at least about 80% homology with a native-sequence Fc region and/or with an Fc region of a parent polypeptide, and most preferably at least about 90% homology therewith, more preferably at least about 95% homology therewith.

Variant Fc sequences may include three amino acid substitutions in the CH2 region to reduce FcγRI binding at EU index positions 234, 235, and 237 (see Duncan et al., (1988) Nature 332:563). Two amino acid substitutions in the complement C1q binding site at EU index positions 330 and 331 reduce complement fixation (see Tao et al., J. Exp. Med. 178:661 (1993) and Canfield and Morrison, J. Exp. Med. 173:1483 (1991)). Substitution into human IgG1 or IgG2 residues at positions 233-236 and IgG4 residues at positions 327, 330 and 331 greatly reduces ADCC and CDC (see, for example, Armour K L. et al., 1999 Eur J Immunol. 29(8): 2613-24; and Shields R L. et al., 2001. J Biol Chem. 276(9):6591-604). The human IgG4 Fc amino acid sequence (UniProtKB No. P01861) is provided herein as SEQ ID NO: 28. Silenced IgG1 is described, for example, in Boesch, A. W., et al., "Highly parallel characterization of IgG Fc binding interactions." MAbs, 2014. 6(4): p. 915-27, the disclosure of which is incorporated herein by reference in its entirety.

Other Fc variants are possible, including, without limitation, one in which a region capable of forming a disulfide bond is deleted, or in which certain amino acid residues are eliminated at the N-terminal end of a native Fc, or a methionine residue is added thereto. Thus, in some embodiments, one or more Fc portions of a binding compound can comprise one or more mutations in the hinge region to eliminate disulfide bonding. In yet another embodiment, the hinge region of an Fc can be removed entirely. In still another embodiment, a binding compound can comprise an Fc variant.

Further, an Fc variant can be constructed to remove or substantially reduce effector functions by substituting (mutating), deleting or adding amino acid residues to effect complement binding or Fc receptor binding. For example, and not limitation, a deletion may occur in a complement-binding site, such as a C1q-binding site. Techniques for preparing such sequence derivatives of the immunoglobulin Fc fragment are disclosed in International Patent Publication Nos. WO 97/34631 and WO 96/32478. In addition, the Fc domain may be modified by phosphorylation, sulfation, acylation, glycosylation, methylation, farnesylation, acetylation, amidation, and the like.

In some embodiments, an antibody comprises a hinge region sequence of a wild type human IgG4 (SEQ ID NO: 32). In some embodiments, an antibody comprises a variant human IgG4 hinge region sequence comprising the mutation S228P (SEQ ID NO: 33).

In some embodiments, an antibody comprises a wild type human IgG4 CH2 domain sequence (SEQ ID NO: 36). In some embodiments, an antibody comprises a variant human IgG4 CH2 domain sequence comprising an F234A mutation, an L235A mutation, or both an F234A mutation and an L235A mutation (SEQ ID NO: 37).

In some embodiments, an antibody comprises a wild type human IgG4 CH3 domain sequence (SEQ ID NO: 38). In some embodiments, an antibody comprises a variant human IgG4 CH3 domain sequence comprising a T366W mutation (SEQ ID NO: 39), which can optionally be referred to herein as an IgG4 CH3 knob sequence. In some embodiments, an antibody comprises a variant human IgG4 CH3 domain sequence comprising a T366S mutation, an L368A mutation, and a Y407V mutation (SEQ ID NO: 40), which can optionally be referred to herein as an IgG4 CH3 hole sequence. The IgG4 CH3 mutations described herein can be utilized in any suitable manner so as to place a "knob" on a first heavy chain constant region of a first monomer in an antibody dimer, and a "hole" on a second heavy chain constant region of a second monomer in an antibody dimer, thereby facilitating proper pairing (heterodimerization) of the desired pair of heavy chain polypeptide subunits in the antibody.

The above-identified hinge region, CH2 domain, and CH3 domain mutations can be incorporated into the antibodies of the invention in any combination. In some embodiments, an antibody comprises a heavy chain polypeptide subunit comprising a variant human IgG4 Fc region comprising an S228P mutation, an F234A mutation, an L235A mutation, and a T366W mutation (knob). In some embodiments, an antibody comprises a heavy chain polypeptide subunit comprising a variant human IgG4 Fc region comprising an S228P mutation, an F234A mutation, an L235A mutation, a T366S mutation, an L368A mutation, and a Y407V mutation (hole).

The term "Fc-region-comprising antibody" refers to an antibody that comprises an Fc region. The C-terminal lysine (residue 447 according to the EU numbering system) of the Fc region may be removed, for example, during purification of the antibody or by recombinant engineering of the nucleic acid encoding the antibody. Accordingly, an antibody having an Fc region according to this invention can comprise an antibody with or without K447.

Aspects of the invention include binding compounds having multi-specific configurations, which include, without limitation, bispecific, trispecific, etc. A large variety of methods and protein configurations are known and used in bispecific monoclonal antibodies (BsMAB), tri-specific antibodies, etc.

Aspects of the invention include antibodies comprising a heavy chain-only variable region in a monovalent or bivalent configuration. As used herein, the term "monovalent configuration" as used in reference to a heavy chain-only variable region domain means that only one heavy chain-only variable region domain is present, having a single binding site (see FIG. 7, Panel B). In contrast, the term "bivalent configuration" as used in reference to a heavy chain-only variable region domain means that two heavy chain-only variable region domains are present (each having a single binding site), and are connected by a linker sequence (see FIG. 7, Panel A). Non-limiting examples of linker sequences are discussed further herein, and include, without limitation, GS linker sequences of various lengths. When a heavy chain-only variable region is in a bivalent configuration, each of the two heavy chain-only variable region domains can have binding affinity to the same antigen, or to different antigens (e.g., to different epitopes on the same protein: to two different proteins, etc.). However, unless specifically noted otherwise, a heavy chain-only variable region denoted as being in a "bivalent configuration" is understood to contain two identical heavy chain-only variable region domains, connected by a linker sequence, wherein each of the two identical heavy chain-only variable region domains has binding affinity to the same target epitope.

Various methods for the production of multivalent artificial antibodies have been developed by recombinantly fusing variable domains of two or more antibodies. In some embodiments, a first and a second antigen-binding domain on a polypeptide are connected by a polypeptide linker. One non-limiting example of such a polypeptide linker is a GS linker, having an amino acid sequence of four glycine residues, followed by one serine residue, and wherein the sequence is repeated n times, where n is an integer ranging from 1 to about 10, such as 2, 3, 4, 5, 6, 7, 8, or 9. Non-limiting examples of such linkers include GGGGS (SEQ ID NO: 34) (n=1) and GGGGSGGGGS (SEQ ID NO: 35) (n=2). In some embodiments, a first heavy chain-only variable region domain and a second heavy chain-only variable region domain are connected to one another on the same heavy chain polypeptide subunit of an antibody to form a bivalent configuration of heavy chain-only variable region domains. In some embodiments, a heavy chain variable region and a light chain variable region are connected to one another on the same heavy chain polypeptide subunit of an antibody (i.e., are disposed on a common polypeptide subunit of the antibody) to form an scFv configuration of the heavy chain and light chain variable region domains. In some embodiments, a heavy chain variable region and a light chain variable region reside on different polypeptide subunits of an antibody to form a binding unit having a traditional antibody configuration of the heavy chain variable region and the light chain variable region. Other suitable linkers can also be used, and are described, for example, in Chen et al., *Adv Drug Deliv Rev.* 2013 Oct. 15; 65(10): 1357-69, the disclosure of which is incorporated herein by reference in its entirety.

The term "three-chain antibody-like molecule" or "TCA" is used herein to refer to antibody-like molecules comprising, consisting essentially of, or consisting of three polypeptide subunits, two of which comprise, consist essentially of, or consist of one heavy and one light chain of a monoclonal antibody, or functional antigen-binding fragments of such antibody chains, comprising an antigen-binding region and at least one CH domain. This heavy chain/light chain pair has binding specificity for a first antigen. The third polypeptide subunit comprises, consists essentially of, or consists of a heavy-chain only antibody comprising an Fc portion comprising CH2 and/or CH3 and/or CH4 domains, in the absence of a CH1 domain, and one or more antigen binding domains (e.g., two antigen binding domains) that binds an epitope of a second antigen or a different epitope of the first antigen, where such binding domain is derived from or has sequence identity with the variable region of an antibody heavy or light chain. Parts of such variable region may be encoded by $V_H$ and/or $V_L$ gene segments, D and $J_H$ gene segments, or $J_L$ gene segments. The variable region may be encoded by rearranged $V_HDJ_H$, $V_LDJ_H$, $V_HJ_L$, or $V_LJ_L$ gene segments. A TCA protein makes use of a heavy chain-only antibody as hereinabove defined.

A TCA binding compound makes use of a "heavy chain-only antibody" or "heavy chain-antibody" or "heavy chain polypeptide" which, as used herein, mean a single chain antibody comprising heavy chain constant regions CH2 and/or CH3 and/or CH4, but no CH1 domain. In one embodiment, the heavy chain antibody is composed of an antigen-binding domain, at least part of a hinge region and CH2 and CH3 domains. In another embodiment, the heavy chain antibody is composed of an antigen-binding domain, at least part of a hinge region and a CH2 domain. In a further embodiment, the heavy chain antibody is composed of an antigen-binding domain, at least part of a hinge region and a CH3 domain. Heavy chain antibodies in which the CH2 and/or CH3 domain is truncated are also included herein. In a further embodiment, the heavy chain is composed of an antigen binding domain, and at least one CH (CH1. CH2, CH3, or CH4) domain but no hinge region. The heavy chain only antibody can be in the form of a dimer, in which two heavy chains are disulfide bonded or otherwise covalently or non-covalently attached with each other, and can optionally include an asymmetric interface between two or more of the CH domains to facilitate proper pairing between polypeptide chains. The heavy-chain antibody may belong to the IgG subclass, but antibodies belonging to other subclasses, such as IgM, IgA, IgD and IgE subclass, are also included herein. In a particular embodiment, the heavy chain antibody is of the IgG1, IgG2, IgG3, or IgG4 subtype, in particular the IgG1 subtype or the IgG4 subtype. Non-limiting examples of a TCA binding compound are described in, for example, WO2017/223111 and WO2018/052503, the disclosures of which are incorporated herein by reference in their entirety.

Heavy-chain antibodies constitute about one fourth of the IgG antibodies produced by the camelids, e.g., camels and llamas (Hamers-Casterman C., et al. Nature. 363, 446-448 (1993)). These antibodies are formed by two heavy chains but are devoid of light chains. As a consequence, the variable antigen binding part is referred to as the VHH domain and it represents the smallest naturally occurring, intact, antigen-binding site, being only around 120 amino acids in length (Desmyter, A., et al. J. Biol. Chem. 276, 26285-26290 (2001)). Heavy chain antibodies with a high specificity and affinity can be generated against a variety of antigens through immunization (van der Linden, R. H., et al. Biochim. Biophys. Acta. 1431, 37-46 (1999)) and the VHH portion can be readily cloned and expressed in yeast (Frenken, L. G. J., et al. J. Biotechnol. 78, 11-21 (2000)). Their levels of expression, solubility and stability are significantly higher than those of classical F(ab) or Fv fragments (Ghahroudi, M. A. et al. FEBS Lett. 414, 521-526 (1997)). Sharks have also been shown to have a single VH-like domain in their antibodies, termed VNAR. (Nuttall et al. Eur. J. Biochem. 270, 3543-3554 (2003); Nuttall et al. Function and Bioinformatics 55, 187-197 (2004); Dooley et al., Molecular Immunology 40, 25-33 (2003)).

The term "BCMA" as used herein relates to human B cell maturation antigen, also known as BCMA, CD269, and TNFRSF17 (UniProt Q02223), which is a member of the tumor necrosis receptor superfamily that is preferentially expressed in differentiated plasma cells. The extracellular domain of human BCMA consists, according to UniProt of amino acids 1-54 (or 5-51). The term "BCMA" includes a BCMA protein of any human or non-human animal species, and specifically includes human BCMA as well as BCMA of non-human animals.

The term "anti-BCMA heavy chain-only antibody," and "BCMA heavy chain-only antibody" are used herein to refer to a heavy chain-only antibody as hereinabove defined, immunospecifically binding to BCMA. The term "human BCMA" as used herein includes any variants, isoforms and species homologs of human BCMA (UniProt Q02223), regardless of its source or mode of preparation. Thus, "human BCMA" includes human BCMA naturally expressed by cells and BCMA expressed on cells transfected with the human BCMA gene.

The terms "anti-BCMA heavy chain-only antibody," "BCMA heavy chain-only antibody," "anti-BCMA heavy chain antibody" and "BCMA heavy chain antibody" are used herein interchangeably to refer to a heavy chain-only antibody as hereinabove defined, immunospecifically binding to BCMA, including human BCMA, as hereinabove defined. The definition includes, without limitation, human heavy chain antibodies produced by transgenic animals, such as transgenic rats or transgenic mice expressing human immunoglobulin, including UniRats™ producing human anti-BCMA UniAb™ antibodies, as hereinabove defined.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

Antibodies of the invention include multi-specific antibodies. Multi-specific antibodies have more than one binding specificity. The term "multi-specific" specifically includes "bispecific" and "trispecific," as well as higher-order independent specific binding affinities, such as higher-order polyepitopic specificity, as well as tetravalent antibodies and antibody fragments. The terms "multi-specific antibody," "multi-specific heavy chain-only antibody," "multi-specific heavy chain antibody," "multi-specific UniAb™", and "multi-specific binding compound" are used herein in the broadest sense and cover all antibodies with more than one binding specificity. The multi-specific anti-BCMA antibodies of the present invention specifically include antibodies immunospecifically binding to one single epitope on a BCMA protein, such as a human BCMA, and to an epitope on a different protein, such as, for example, a CD3 protein. The multi-specific anti-BCMA antibodies of the present invention specifically include antibodies immunospecifically binding to two or more non-overlapping epitopes on a BCMA protein, such as a human BCMA. The multi-specific anti-BCMA antibodies of the present invention also specifically include antibodies immunospecifically binding to an epitope on a BCMA protein, such as human BCMA, and to an epitope on a different protein, such as, for example, human La protein. The multi-specific anti-BCMA antibodies of the present invention also specifically include antibodies immunospecifically binding to two or more non-overlapping or partially overlapping epitopes on a BCMA protein, such as a human BCMA protein, and to an epitope on a different protein, such as, for example, a human La protein.

Antibodies of the invention include monospecific antibodies, having one binding specificity. Monospecific antibodies specifically include antibodies comprising a single binding specificity, as well as antibodies comprising more than one binding unit having the same binding specificity. The terms "monospecific antibody," "monospecific heavy chain-only antibody," "monospecific heavy chain antibody," and "monospecific UniAb™" are used herein in the broadest sense and cover all antibodies with one binding specificity. The monospecific heavy chain anti-BCMA antibodies of the present invention specifically include antibodies immunospecifically binding to one epitope on a BCMA protein, such as a human BCMA (monovalent and monospecific). The monospecific heavy chain anti-BCMA antibodies of the present invention also specifically include antibodies having more than one binding unit (e.g., multivalent antibodies) immunospecifically binding to an epitope on a BCMA protein, such as human BCMA. For example, a monospecific antibody in accordance with embodiments of the invention can include a heavy chain-only variable region comprising two heavy chain-only antigen-binding domains (i.e., an anti-BCMA heavy chain-only variable region in a tandem configuration), wherein each of the two antigen-binding domains binds to the same epitope on a BCMA protein (i.e., bivalent and monospecific).

An "epitope" is the site on the surface of an antigen molecule to which a single antibody molecule binds. Generally, an antigen has several or many different epitopes and reacts with many different antibodies. The term specifically includes linear epitopes and conformational epitopes.

"Epitope mapping" is the process of identifying the binding sites, or epitopes, of antibodies on their target antigens. Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure.

"Polyepitopic specificity" refers to the ability to specifically bind to two or more different epitopes on the same or different target(s). As noted above, the present invention specifically includes anti-BCMA heavy chain antibodies with polyepitopic specificities, i.e., anti-BCMA heavy chain antibodies binding to one or more non-overlapping epitopes on a BCMA protein, such as a human BCMA; and anti-BCMA heavy chain antibodies binding to one or more epitopes on a BCMA protein and to an epitope on a different protein, such as, for example, human La protein. The term "non-overlapping epitope(s)" or "non-competitive epitope(s)" of an antigen is defined herein to mean epitope(s) that are recognized by one member of a pair of antigen-specific antibodies but not the other member. Pairs of antibodies, or antigen-binding regions targeting the same antigen on a multi-specific antibody, recognizing non-overlapping epitopes, do not compete for binding to that antigen and are able to bind that antigen simultaneously.

An antibody binds "essentially the same epitope" as a reference antibody, when the two antibodies recognize identical or sterically overlapping epitopes. The most widely used and rapid methods for determining whether two epitopes bind to identical or sterically overlapping epitopes are competition assays, which can be configured in all number of different formats, using either labeled antigen or labeled antibody. Usually, the antigen is immobilized on a 96-well plate, and the ability of unlabeled antibodies to block the binding of labeled antibodies is measured using radioactive or enzyme labels.

The term "valent" as used herein refers to a specified number of binding sites in an antibody molecule.

A "monovalent" antibody has one binding site. Thus a monovalent antibody is also monospecific.

A "multi-valent" antibody has two or more binding sites. Thus, the terms "bivalent", "trivalent", and "tetravalent" refer to the presence of two binding sites, three binding sites, and four binding sites, respectively. Thus, a bispecific antibody according to the invention is at least bivalent and may be trivalent, tetravalent, or otherwise multi-valent. A bivalent antibody in accordance with embodiments of the invention may have two binding sites to the same epitope (i.e., bivalent, monoparatopic), or to two different epitopes (i.e., bivalent, biparatopic).

A large variety of methods and protein configurations are known and used for the preparation of bispecific monoclonal antibodies (BsMAB), tri-specific antibodies, and the like.

The term "chimeric antigen receptor" or "CAR" is used herein in the broadest sense to refer to an engineered receptor, which grafts a desired binding specificity (e.g., the antigen-binding region of a monoclonal antibody or other ligand) to membrane-spanning and intracellular-signaling domains. Typically, the receptor is used to graft the specificity of a monoclonal antibody onto a T-cell to create a chimeric antigen receptor (CAR). (*J Natl Cancer Inst,* 2015; 108(7):dvj439; and Jackson et al., *Nature Reviews Clinical Oncology,* 2016; 13:370-383). CAR-T cells are T-cells that have been genetically engineered to produce an artificial T-cell receptor for use in immunotherapy. In one embodiment, "CAR-T-cell" means a therapeutic T-cell expressing a transgene encoding one or more chimeric antigen receptors comprised minimally of an extracellular domain, a transmembrane domain, and at least one cytosolic domain.

The term "human antibody" is used herein to include antibodies having variable and constant regions derived from human germline immunoglobulin sequences. The human antibodies herein may include amino acid residues not encoded by human germline immunoglobulin sequences, e.g., mutations introduced by random or site-specific mutagenesis in vitro or by somatic mutation in vivo. The term "human antibody" specifically includes heavy chain-only antibodies having human heavy chain variable region sequences, produced by transgenic animals, such as transgenic rats or mice, in particular UniAbs™ produced by UniRats™, as defined above.

By a "chimeric antibody" or a "chimeric immunoglobulin" is meant an immunoglobulin molecule comprising amino acid sequences from at least two different Ig loci, e.g., a transgenic antibody comprising a portion encoded by a human Ig locus and a portion encoded by a rat Ig locus. Chimeric antibodies include transgenic antibodies with non-human Fc-regions or artificial Fc-regions, and human idiotypes. Such immunoglobulins can be isolated from animals of the invention that have been engineered to produce such chimeric antibodies.

As used herein, the term "effector cell" refers to an immune cell which is involved in the effector phase of an immune response, as opposed to the cognitive and activation phases of an immune response. Some effector cells express specific Fc receptors and carry out specific immune functions. In some embodiments, an effector cell such as a natural killer cell is capable of inducing antibody-dependent cellular cytotoxicity (ADCC). For example, monocytes and macrophages, which express FcR, are involved in specific killing of target cells and presenting antigens to other components of the immune system, or binding to cells that present antigens. In some embodiments, an effector cell may phagocytose a target antigen or target cell.

"Human effector cells" are leukocytes which express receptors such as T cell receptors or FcRs and perform effector functions. Preferably, the cells express at least FcγRIII and perform ADCC effector function. Examples of human leukocytes which mediate ADCC include natural killer (NK) cells, monocytes, cytotoxic T cells and neutrophils, with NK cells being preferred. The effector cells may be isolated from a native source thereof, e.g., from blood or PBMCs as described herein.

The term "immune cell" is used herein in the broadest sense, including, without limitation, cells of myeloid or lymphoid origin, for instance lymphocytes (such as B cells and T cells including cytolytic T cells (CTLs)), killer cells, natural killer (NK) cells, macrophages, monocytes, eosinophils, polymorphonuclear cells, such as neutrophils, granulocytes, mast cells, and basophils.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc.

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS* (*USA*) 95:652-656 (1998).

"Complement dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g., as described in Gazzano-Santoro et al., *J. Immunol. Methods* 202:163 (1996), may be performed.

"Binding affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art. Low-affinity antibodies generally bind antigen slowly and tend to dissociate readily, whereas high-affinity antibodies generally bind antigen faster and tend to remain bound.

As used herein, the "Kd" or "Kd value" refers to a dissociation constant determined by BioLayer Interferometry, using an Octet QK384 instrument (Fortebio Inc., Menlo Park, CA) in kinetics mode. For example, anti-mouse Fc sensors are loaded with mouse-Fc fused antigen and then dipped into antibody-containing wells to measure concentration dependent association rates (kon). Antibody dissociation rates (koff) are measured in the final step, where the sensors are dipped into wells containing buffer only. The Kd is the ratio of koff/kon. (For further details see, Concepcion, J, et al., *Comb Chem High Throughput Screen,* 12(8), 791-800, 2009).

As used herein, the terms "specifically interacting", "specifically binding" or "specifically bind(s)" mean that a binding domain exhibits appreciable affinity for a particular target protein or antigen and, generally, does not exhibit significant reactivity with non-target proteins or antigens. "Appreciable affinity" includes binding with an affinity of about $10^{-6}$ M (KD) or stronger. Preferably, binding is considered specific when binding affinity is about $10^{-12}$ to $10^{-8}$ M, $10^{-12}$ to $10^{-9}$ M, $10^{-9}$ to $10^{-10}$ M, $10^{-11}$ to $10^{-8}$ M, preferably of about $10^{-11}$ to $10^{-9}$ M. Whether a binding domain specifically reacts with or binds to a target protein or antigen can be tested readily by, inter alia, comparing the reaction of said binding domain with a target protein or antigen with the reaction of said binding domain with non-target proteins or antigens. Preferably, a binding domain of the invention does not essentially bind or is not capable of binding to non-target proteins or antigens.

The term "does not essentially bind", or "is not capable of binding" means that a binding domain of the present invention does not bind to a non-target protein or antigen, i.e., does not show reactivity of more than 30%, preferably not more than 20%, more preferably not more than 10%, particularly preferably not more than 9%, 8%, 7%, 6% or 5% with non-target proteins or antigens, whereby binding to a target protein or antigen, respectively, is set to be 100%.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy may be administered during the symptomatic stage of the disease, and in some cases after the symptomatic stage of the disease.

A "therapeutically effective amount" is intended for an amount of active agent which is necessary to impart therapeutic benefit to a subject. For example, a "therapeutically effective amount" is an amount which induces, ameliorates or otherwise causes an improvement in the pathological symptoms, disease progression or physiological conditions associated with a disease or which improves resistance to a disorder.

The terms "B-cell neoplasms" or "mature B-cell neoplasms" in the context of the present invention include, but are not limited to, all lymphoid leukemias and lymphomas, chronic lymphocytic leukemia, acute lymphoblastc leukemia, prolymphocytic leukemia, precursor B-lymphoblastic leukemia, hair cell leukemia, small lymphocytic lymphoma, B-cell prolymphocytic lymphoma, B-cell chronic lymphocytic leukemia, mantle cell lymphoma, Burkitt's lymphoma, follicular lymphoma, diffuse large B-cell lymphoma (DLBCL), multiple myeloma, lymphoplasmacytic lymphoma, splenic marginal zone lymphoma, plasma cell neoplasms, such as plasma cell myeloma, plasmacytoma, monoclonal immunoglobulin deposition disease, heavy chain disease, MALT lymphoma, nodal marginal B cell lymphoma, intravascular large B cell lymphoma, primary effusion lymphoma, lymphomatoid granulomatosis, non-Hodgkins lymphoma, Hodgkins lymphoma, hairy cell leukemia, primary effusion lymphoma and AIDS-related non-Hodgkins lymphoma.

The term "characterized by expression of BCMA" broadly refers to any disease or disorder in which BCMA expression is associated with or involved with one or more pathological processes that are characteristic of the disease or disorder. Such disorders include, but are not limited to, B-cell neoplasms.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer, individuals with autoimmune diseases, with pathogen infections, and the like. Subjects may be human, but also include other mammals, particularly those mammals useful as laboratory models for human disease, e.g., mouse, rat, etc.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile. "Pharmaceutically acceptable" excipients (vehicles, additives) are those which can reasonably be administered to a subject mammal to provide an effective dose of the active ingredient employed.

A "sterile" formulation is aseptic or free or essentially free from all living microorganisms and their spores. A "frozen" formulation is one at a temperature below 0° C.

A "stable" formulation is one in which the protein therein essentially retains its physical stability and/or chemical stability and/or biological activity upon storage. Preferably, the formulation essentially retains its physical and chemical stability, as well as its biological activity upon storage. The storage period is generally selected based on the intended shelf-life of the formulation. Various analytical techniques for measuring protein stability are available in the art and are reviewed in Peptide and Protein Drug Delivery, 247-301. Vincent Lee Ed., Marcel Dekker, Inc., New York, N.Y., Pubs. (1991) and Jones. A. Adv. Drug Delivery Rev. 10: 29-90) (1993), for example. Stability can be measured at a selected temperature for a selected time period. Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography, image capillary isoelectric focusing (icIEF) or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or antigen binding function of the antibody; etc. Instability may involve any one or more of: aggregation, deamidation (e.g., Asn deamidation), oxidation (e.g., Met oxidation), isomerization (e.g., Asp isomerisation), clipping/hydrolysis/fragmentation (e.g., hinge region fragmentation), succinimide formation, unpaired cysteine(s), N-terminal extension, C-terminal processing, glycosylation differences, etc.

II. DETAILED DESCRIPTION

Anti-BCMA Antibodies

The present invention provides antibodies, including, but not limited to, heavy chain-only antibodies (UniAbs) that bind to human BCMA. The anti-BCMA UniAbs of the invention comprise a set of CDR sequences as defined herein and shown in FIG. 1, and are exemplified by the provided heavy chain variable region (VH) sequence of SEQ ID NO: 12, set forth in FIG. 2. These antibodies provide a number of benefits that contribute to utility as clinically therapeutic agent(s). The antibodies include members with a range of binding affinities, allowing the selection of a specific sequence with a desired binding affinity.

The anti-BCMA antibodies provided herein are not cross-reactive with the BCMA protein of Cynomolgus macaque, but can be engineered to provide cross-reactivity with the BCMA protein of Cynomolgus macaque, or with the BCMA of any other animal species, if desired.

In some embodiments, the anti-BCMA UniAb antibodies herein comprise a VH domain, comprising CDR1, CDR2 and CDR3 sequences in a human VH framework. The CDR sequences may be situated, as an example, in the region of around amino acid residues 26-35; 53-59; and 98-117 for CDR1, CDR2 and CDR3, respectively, of the provided exemplary variable region sequence set forth in SEQ ID NO: 12. It will be understood by one of skill in the art that the CDR sequences may be in different positions if a different framework sequence is selected, although generally the order of the sequences will remain the same.

In some embodiments, an anti-BCMA antibody comprises a variable region comprising a CDR1 sequence comprising two or fewer amino acid substitutions in the sequence of SEQ ID NO: 1, and/or a CDR2 sequence comprising two or fewer substitutions in the sequence of SEQ ID NO: 2, and/or a CDR3 sequence comprising two or fewer substitutions in the sequence of SEQ ID NO: 3.

In some embodiments, an anti-BCMA antibody comprises a variable region comprising a CDR1 sequence comprising two or fewer substitutions in the sequence of SEQ ID NO: 1, and a CDR2 sequence comprising two or fewer substitutions in the sequence of SEQ ID NO: 2, and a CDR3 sequence comprising two or fewer substitutions in the sequence of SEQ ID NO: 3.

In some embodiments, an anti-BCMA antibody comprises a variable region comprising a CDR1 sequence of SEQ ID NO: 1, a CDR2 sequence of SEQ ID NO: 2 and a CDR3 sequence of SEQ ID NO: 3.

In some embodiments, an anti-BCMA antibody comprises a heavy chain-only variable region comprising the CDR1, CDR2 and CDR3 sequences of SEQ ID NOs 1, 2, and 3, respectively. In some embodiments, an anti-BCMA antibody comprises a heavy chain-only variable region in a monovalent or bivalent configuration.

In further embodiments, an anti-BCMA antibody of the present invention comprises a heavy chain variable region amino acid sequence of SEQ ID NO: 12, in a monovalent or bivalent configuration (FIG. 2).

In some embodiments, an anti-BCMA antibody preferably comprises a CDR sequence comprising two or fewer amino acid substitutions relative to a CDR1, CDR2 and/or CDR3 sequence in any one of SEQ ID NOs:1-3 (FIG. 1), and binds to BCMA. In some embodiments, an anti-BCMA antibody preferably comprises a heavy chain variable region sequence with at least 80% identity, at least 85% identity, at least 90% identity, at least 95% identity, at least 98% identify, or at least 99% identity to the heavy chain variable region sequence shown in FIG. 2 (SEQ ID NO: 12), and binds to BCMA.

In some embodiments, an anti-BCMA antibody preferably comprises a heavy chain variable domain (VH) in which the CDR3 sequence has greater than or equal to 80%, such as at least 85%, at least 90%, at least 95%, or at least 99% sequence identity at the amino acid level to SEQ ID NO: 3, and binds to BCMA.

In some embodiments, an anti-BCMA antibody preferably comprises a heavy chain variable domain (VH) in which the full set of CDRs 1, 2, and 3 (combined) has greater than or equal to eighty-five percent (85%) sequence identity at the amino acid level to the CDRs 1, 2, and 3 (combined) of SEQ ID NOs: 1-3, and binds to BCMA.

The present invention provides multi-specific antibodies that bind to human BCMA as well as human La protein. The multi-specific antibodies of the invention can comprise a first binding unit that binds to BCMA, and a second binding unit that binds to human La protein. In some embodiments, a binding unit that binds to human La protein comprises a set of CDR sequences as defined herein and shown in FIG. 1, and are exemplified by the provided heavy chain variable region (VH) sequences of SEQ ID NOs: 14-15 and light chain variable region (VL) sequences of SEQ ID NOs: 16 and 17, set forth in FIG. 3. In some embodiments, an antibody that binds to human La protein binds to an epitope comprising the amino acid sequence KPLPEVTDEY (SEQ ID NO: 42). In some embodiments, an antibody that binds to human La protein binds to an epitope comprising the amino acid sequence VEKEALKKIIEDQQESLNKW (SEQ ID NO: 43). Antibodies that bind to human La protein are described, for example, in WO2016030414, US20200181228, US20200131262, and US20170240612, the disclosures of which are herein incorporated by reference in their entireties.

The antibodies described herein provide a number of benefits that contribute to utility as clinically therapeutic agent(s). The antibodies include members with a range of binding affinities, allowing the selection of a specific sequence with a desired binding affinity.

A suitable antibody may be selected from those provided herein for development and therapeutic or other use, including, without limitation, use as a bispecific or tri-specific antibody, or part of a CAR-T structure.

Determination of affinity for a candidate protein can be performed using methods known in the art, such as Biacore measurements. The subject antibodies may have an affinity for human La protein with a Kd of from about $10^{-6}$ to around about $10^{-11}$, including without limitation: from about $10^{-6}$ to around about $10^{-10}$, from about $10^{-6}$ to around about $10^{-9}$; from about $10^{-6}$ to around about $10^{-8}$; from about $10^{-8}$ to around about $10^{-11}$; from about $10^{-8}$ to around about $10^{-10}$; from about $10^{-8}$ to around about $10^{-9}$; from about $10^{-9}$ to around about $10^{-11}$; from about $10^{-9}$ to around about $10^{-10}$; or any value within these ranges. The affinity selection may be confirmed with a biological assessment for modulating, e.g., increasing, a desired activity (e.g., a desired binding affinity between a universal CAR structure and a binding unit of a subject multi-specific antibody), including in vitro assays, pre-clinical models, and clinical trials, as well as assessment of potential toxicity.

In some embodiments, the anti-human La protein binding unit of a subject antibody comprises a VH domain, comprising CDR1, CDR2 and CDR3 sequences in a human VH framework, and a VL domain, comprising CDR1, CDR2 and CDR3 sequences in a human VL framework, e.g., a human Vkappa framework or a human Vlambda framework. The CDR sequences may be situated, as an example, in the region of around amino acid residues 26-35; 53-59; and 98-117 for CDR1, CDR2 and CDR3, respectively, of the provided exemplary variable region sequences set forth in SEQ ID NOs: 14-17. It will be understood by one of skill in the art that the CDR sequences may be in different positions if a different framework sequence is selected, although generally the order of the sequences will remain the same.

In some embodiments, the anti-human La protein binding unit of a subject antibody comprises a heavy chain variable region comprising a CDR1 sequence comprising two or fewer substitutions in any one of the sequences of SEQ ID NOs: 4 or 7, and/or a CDR2 sequence comprising two or fewer substitutions in the sequence of SEQ ID NO: 5, and/or a CDR3 sequence comprising two or fewer substitutions in any one of the sequences of SEQ ID NOs: 6 or 8, and a light chain variable region comprising a CDR1 sequence comprising two or fewer substitutions in the sequence of SEQ ID NO: 9, and/or a CDR2 sequence comprising two or fewer substitutions in the sequence of SEQ ID NO: 10, and/or a CDR3 sequence comprising two or fewer substitutions in the sequence of SEQ ID NO: 11.

In some embodiments, the anti-human La protein binding unit of a subject antibody comprises a heavy chain variable region comprising a CDR1 sequence comprising two or fewer substitutions in any one of the sequences of SEQ ID NOs: 4 or 7, and a CDR2 sequence comprising two or fewer substitutions in the sequence of SEQ ID NO: 5, and a CDR3 sequence comprising two or fewer substitutions in any one of the sequences of SEQ ID NOs: 6 or 8, and a light chain variable region comprising a CDR1 sequence comprising two or fewer substitutions in the sequence of SEQ ID NO: 9, and a CDR2 sequence comprising two or fewer substitutions in the sequence of SEQ ID NO: 10, and a CDR3 sequence comprising two or fewer substitutions in the sequence of SEQ ID NO: 11.

In one embodiment, the anti-human La protein binding unit of an antibody of the present invention comprises a heavy chain comprising the CDR1 sequence of SEQ ID NO: 4; the CDR2 sequence of SEQ ID NO: 5 and a CDR3 sequence of SEQ ID NO: 6 and a light chain comprising the CDR1 sequence of SEQ ID NO: 9, the CDR2 sequence of SEQ ID NO: 10 and the CDR3 sequence of SEQ ID NO: 11. In one embodiment, the anti-human La protein binding unit of an antibody of the present invention comprises a heavy chain comprising the CDR1 sequence of SEQ ID NO: 7; the CDR2 sequence of SEQ ID NO: 5 and a CDR3 sequence of SEQ ID NO: 8 and a light chain comprising the CDR1 sequence of SEQ ID NO: 9, the CDR2 sequence of SEQ ID NO: 10 and the CDR3 sequence of SEQ ID NO: 11.

In further embodiments, the anti-human La protein binding unit of an antibody of the present invention comprises the heavy chain variable region amino acid sequence of SEQ ID NO: 14 and a light chain variable region sequence of SEQ ID NO: 16. In some embodiments, the anti-human La protein binding unit of an antibody of the present invention comprises the heavy chain variable region amino acid sequence of SEQ ID NO: 15 and a light chain variable region sequence of SEQ ID NO: 17.

In some embodiments, a heavy chain CDR sequence in the anti-human La protein binding unit of the antibodies of the present invention comprises two or fewer amino acid substitutions relative to a CDR1. CDR2 and/or CDR3 sequence in any one of SEQ ID NOs: 4-8 (FIG. 1). In some embodiments, the anti-human La protein binding unit of the antibodies of the present invention will comprise a heavy chain variable region sequence with at least 85% identity, at least 90% identity, at least 95% identity, at least 98% identify, or at least 99% identity to the heavy chain variable region sequences shown in FIG. 3 (SEQ ID NOs: 14 and 15).

In some embodiments, a light chain CDR sequence in the anti-human La protein binding unit of the antibodies of the present invention comprises two or fewer amino acid substitutions relative to a CDR1. CDR2 and/or CDR3 sequence in any one of SEQ ID NOs: 9-11 (FIG. 1). In some embodiments, the anti-human La protein binding unit of the antibodies of the present invention will comprise a light chain variable region sequence with at least 85% identity, at least 90% identity, at least 95% identity, at least 98% identify, or at least 99% identity to the light chain variable region sequences shown in FIG. 3 (SEQ ID NOs: 16 and 17).

In some embodiments, multi-specific (e.g., bispecific) antibodies are provided, which may have any of the configurations discussed herein, including, without limitation, a three chain bispecific antibody, or a three chain bispecific antibody-like molecule (a bispecific TCA). Bispecific antibodies comprise at least the heavy chain variable region of an antibody specific for a protein other than BCMA.

Where a protein of the invention is a bispecific antibody, one binding unit is specific for human BCMA, while another binding unit may be specific for target cells (e.g., effector cells, e.g., T-cells), tumor associated antigens, targeting antigens, e.g., integrins, etc., pathogen antigens, checkpoint proteins, a protein on a universal CAR structure, and the like. Target cells specifically include cancer cells, such as hematologic tumors, e.g., B-cell tumors, as discussed below. In some embodiments, a bispecific antibody comprises a first binding unit that binds to BCMA and a second binding unit that binds to human La protein.

Various formats of multi-specific antibodies are within the ambit of the invention, including, without limitation, single chain polypeptides, two chain polypeptides, three chain polypeptides, four chain polypeptides, and multiples thereof. The multi-specific (e.g., bispecific) antibodies herein specifically include T-cell bispecific antibodies binding to BCMA, which is selectively expressed on plasma cells (PCs) and multiple myeloma (MM) cells, and CD3 (anti-BCMA x anti-CD3 antibodies). The multi-specific (e.g., bispecific) antibodies herein also specifically include universal CAR bispecific antibodies binding to BCMA, which is selectively expressed on plasma cells (PCs) and multiple myeloma (MM) cells, and an antigen on a universal CAR structure (anti-BCMA x anti-La protein antibodies). Such antibodies induce potent T-cell or CAR T-cell mediated killing of cells expressing BCMA, and can be used to treat tumors, in particular hematologic tumors, such as B-cell tumors, as discussed below, as well as autoimmune disorders characterized by the presence of self-reactive plasma cells, which are also described further herein.

Bispecific antibodies against CD3 and BCMA are described, for example, in WO2007117600, WO2009132058, WO2012066058, WO2012143498, WO2013072406, WO2013072415, and WO2014122144, and in US 20170051068. Universal chimeric antigen receptors comprising human La protein are described, for example, in WO2016030414, the disclosure of which application is incorporated by reference herein in its entirety.

Preparation of Antibodies

The multi-specific antibodies of the present invention can be prepared by methods known in the art. In a preferred embodiment, the antibodies herein are produced by transgenic animals, including transgenic mice and rats, preferably rats, in which the endogenous immunoglobulin genes are knocked out or disabled. In a preferred embodiment, the antibodies herein are produced in a UniRat™. UniRats™ have their endogenous immunoglobulin genes silenced and use a human immunoglobulin heavy-chain translocus to express a diverse, naturally optimized repertoire of fully human HCAbs. While endogenous immunoglobulin loci in rats can be knocked out or silenced using a variety of technologies, in UniRat™ the zinc-finger (endo)nuclease (ZNF) technology was used to inactivate the endogenous rat heavy chain J-locus, light chain Cu locus and light chain C locus. ZNF constructs for microinjection into oocytes can produce IgH and IgL knock out (KO) lines. For details see, e.g., Geurts et al., 2009, Science 325:433. Characterization of Ig heavy chain knockout rats has been reported by Menoret et al., 2010, Eur. J. Immunol. 40:2932-2941. Advantages of the ZNF technology are that non-homologous end joining to silence a gene or locus via deletions up to several kb can also provide a target site for homologous integration (Cui et al., 2011, Nat Biotechnol 29:64-67). Human heavy chain antibodies produced in UniRat™ are called UniAbs™ and can bind epitopes that cannot be attacked with conventional antibodies. Their high specificity, affinity, and small size make them ideal for mono- and poly-specific applications.

In addition to UniAbs™, specifically included herein are heavy chain-only antibodies lacking the camelid VHH framework and mutations, and their functional VH regions. Such heavy chain-only antibodies can, for example, be produced in transgenic rats or mice which comprise fully human heavy chain-only gene loci as described, e.g., in WO2006/008548, but other transgenic mammals, such as rabbit, guinea pig, rat can also be used, rats and mice being preferred. Heavy chain-only antibodies, including their VHH or VH functional fragments, can also be produced by recombinant DNA technology, by expression of the encoding nucleic acid in a suitable eukaryotic or prokaryotic host, including, for example, mammalian cells (e.g., CHO cells), *E. coli* or yeast.

Domains of heavy chain-only antibodies combine advantages of antibodies and small molecule drugs: can be mono- or multi-valent; have low toxicity; and are cost-effective to manufacture. Due to their small size, these domains are easy to administer, including oral or topical administration, are characterized by high stability, including gastrointestinal stability; and their half-life can be tailored to the desired use or indication. In addition, VH and VHH domains of HCAbs can be manufactured in a cost effective manner.

In a particular embodiment, the heavy chain antibodies of the present invention, including UniAbs™, have the native amino acid residue at the first position of the FR4 region (amino acid position 101 according to the Kabat numbering system), substituted by another amino acid residue, which is capable of disrupting a surface-exposed hydrophobic patch comprising or associated with the native amino acid residue at that position. Such hydrophobic patches are normally buried in the interface with the antibody light chain constant region but become surface exposed in HCAbs and are, at least partially, for the unwanted aggregation and light chain association of HCAbs. The substituted amino acid residue preferably is charged, and more preferably is positively charged, such as lysine (Lys, K), arginine (Arg, R) or histidine (His, H), preferably arginine (R). In a preferred embodiment the heavy chain-only antibodies derived from the transgenic animals contain a Trp to Arg mutation at position 101. The resultant HCAbs preferably have high antigen-binding affinity and solubility under physiological conditions in the absence of aggregation.

As part of the present invention, human anti-BCMA heavy chain antibodies with unique sequences from UniRat™ animals (UniAb™) were identified that bind human BCMA in ELISA protein and cell-binding assays. The identified heavy chain variable region (VH) sequences (see, e.g., FIG. 2) are positive for human BCMA protein binding and/or for binding to BCMA+ cells, and are all negative for binding to cells that do not express BCMA.

Heavy chain antibodies binding to non-overlapping epitopes on a BCMA protein. e.g., UniAbs™ can be identified by competition binding assays, such as enzyme-linked immunoassays (ELISA assays) or flow cytometric competitive binding assays. For example, one can use competition between known antibodies binding to the target antigen and the antibody of interest. By using this approach, one can divide a set of antibodies into those that compete with the reference antibody and those that do not. The non-competing antibodies are identified as binding to a distinct epitope that does not overlap with the epitope bound by the reference antibody. Often, one antibody is immobilized, the antigen is bound, and a second, labeled (e.g., biotinylated) antibody is tested in an ELISA assay for ability to bind the captured antigen. This can be performed also by using surface plasmon resonance (SPR) platforms, including ProteOn XPR36 (BioRad, Inc), Biacore 2000 and Biacore T200 (GE Healthcare Life Sciences), and MX96 SPR imager (Ibis technologies B.V.), as well as on biolayer interferometry platforms, such as Octet Red384 and Octet HTX (ForteBio, Pall Inc). For further details see the examples herein.

Typically, an antibody "competes" with a reference antibody if it causes about 15-100% reduction in the binding of the reference antibody to the target antigen, as determined by standard techniques, such as by the competition binding assays described above. In various embodiments, the relative inhibition is at least about 15%, at least about 20%, at least about 25%, at least about 30%, at least about 35%, at least about 40%, at least about 45%, at least about 50% at least about 55%, at least about 60%, at least about 65%, at least about 70%, at least about 75%, at least about 80%, at least about 85%, at least about 90° %, at least about 95% or higher.

Pharmaceutical Compositions

It is another aspect of the present invention to provide pharmaceutical compositions comprising one or more antibodies of the present invention in admixture with a suitable pharmaceutically acceptable carrier. Pharmaceutically acceptable carriers as used herein are exemplified, but not limited to, adjuvants, solid carriers, water, buffers, or other carriers used in the art to hold therapeutic components, or combinations thereof.

Pharmaceutical compositions of the antibodies used in accordance with the present invention are prepared for storage by mixing proteins having the desired degree of purity with optional pharmaceutically acceptable carriers, excipients or stabilizers (see, e.g., Remington's Pharmaceutical Sciences 16th edition, Osol, A. Ed. (1980)), such as in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Pharmaceutical compositions for parenteral administration are preferably sterile and substantially isotonic and manufactured under Good Manufacturing Practice (GMP) conditions. Pharmaceutical compositions can be provided in unit dosage form (i.e., the dosage for a single administration). The formulation depends on the route of administration chosen. The antibodies herein can be administered by intravenous injection or infusion or subcutaneously. For injection administration, the antibodies herein can be formulated in aqueous solutions, preferably in physiologically-compatible buffers to reduce discomfort at the site of injection. The solution can contain carriers, excipients, or stabilizers as discussed above. Alternatively, antibodies can be in lyophilized form for constitution with a suitable vehicle, e.g., sterile pyrogen-free water, before use.

Anti-BCMA antibody formulations are disclosed, for example, in U.S. Pat. No. 9,034,324. Similar formulations can be used for the proteins of the present invention. Subcutaneous antibody formulations are described, for example, in US 20160355591 and US 20160166689.

METHODS OF USE

The antibodies and pharmaceutical compositions herein can be used for the treatment of B-cell related disorders, including B-cell and plasma cell malignancies and autoimmune disorders characterized by the expression or overexpression of BCMA.

Such B-cell related disorders include B-cell and plasma cell malignancies and autoimmune disorders, including, without limitation, plasmacytoma, Hodgkins' lymphoma, follicular lymphomas, small non-cleaved cell lymphomas, endemic Burkitt's lymphoma, sporadic Burkitt's lymphoma, marginal zone lymphoma, extranodal mucosa-associated lymphoid tissue lymphoma, nodal monocytoid B cell lymphoma, splenic lymphoma, mantle cell lymphoma, large cell lymphoma, diffuse mixed cell lymphoma, immunoblastic lymphoma, primary mediastinal B cell lymphoma, pulmonary B cell angiocentric lymphoma, small lymphocytic lymphoma, B cell proliferations of uncertain malignant potential, lymphomatoid granulomatosis, post-transplant lymphoproliferative disorder, an immunoregulatory disorder, rheumatoid arthritis, myasthenia gravis, idiopathic thrombocytopenia purpura, anti-phospholipid syndrome, Chagas' disease, Grave's disease, Wegener's granulomatosis, poly-arteritis nodosa, Sjogren's syndrome, pemphigus vulgaris, scleroderma, multiple sclerosis, anti-phospholipid syndrome, ANCA associated vasculitis, Goodpasture's disease, Kawasaki disease, autoimmune hemolytic anemia, and rapidly progressive glomerulonephritis, heavy-chain disease, primary or immunocyte-associated amyloidosis, or monoclonal gammopathy.

The plasma cell disorders characterized by the expression of BCMA include Multiple Myeloma (MM). MM is a B-cell malignancy characterized by a monoclonal expansion and accumulation of abnormal plasma cells in the bone marrow compartment. Current therapies for MM often cause remissions, but nearly all patients eventually relapse and die. There is substantial evidence of an immune-mediated elimination of myeloma cells in the setting of allogeneic hematopoietic stem cell transplantation; however, the toxicity of this approach is high, and few patients are cured. Although some monoclonal antibodies have shown promise for treating MM in preclinical studies and early clinical trials, consistent clinical efficacy of any monoclonal antibody therapy for MM has not been conclusively demonstrated. There is therefore a great need for new therapies, including immunotherapies, for MM (see, e.g. Carpenter et al., Clin Cancer Res 2013, 19(8):2048-2060).

Overexpression or activation of BCMA by its proliferation-inducing ligand, APRIL it known to promote human Multiple Myeloma (MM) progression in vivo. BCMA has also been shown to promote in vivo growth of xenografted MM cells harboring p53 mutation in mice. Since activity of the APRIL/BCMA pathway plays a central role in MM pathogenesis and drug resistance via bidirectional interactions between tumor cells and their supporting bone marrow microenvironment, BCMA has been identified as a target for the treatment of MM. For further details see, e.g., Yu-Tsu Tai et al., Blood 2016; 127(25):3225-3236.

Another B-cell disorder involving plasma cells expressing BCMA is systemic lupus erythematosus (SLE), also known as lupus. SLE is a systemic, autoimmune disease that can affect any part of the body and is represented with the immune system attacking the body's own cells and tissue, resulting in chronic inflammation and tissue damage. It is a Type III hypersensitivity reaction in which antibody-immune complexes precipitate and cause a further immune response (Inaki & Lee, Nat Rev Rheumatol 2010; 6: 326-337).

The anti-BCMA heavy chain-only antibodies (UniAbs) of the present invention can be used to develop therapeutic agents for the treatment of MM, SLE, and other B-cell disorders or plasma cell disorders characterized by the expression of BCMA, such as those listed above. In particular, the anti-BCMA heavy chain-only antibodies (UniAbs) of the present invention are candidates for the treatment of MM, alone or in combination with other MM treatments.

In one embodiment, the antibodies herein can be in the form of heavy chain-only anti-BCMA antibody-CAR structures, i.e., heavy chain-only anti-BCMA antibody-CAR-transduced T-cell structures. CARs having antigen specificity for BCMA, and their methods of use, are described, for example, in WO2019/006072, the disclosure of which is incorporated by reference herein in its entirety.

In some embodiments, the antibodies herein are multi-specific (e.g., bispecific), comprising a first binding unit with binding affinity to BCMA, and a second binding unit with binding affinity for La protein, which is present on a universal chimeric antigen receptor (CAR) complex on an effector cell (e.g., a T-cell). As such, the multi-specific antibodies of the invention can be used to functionalize a universal CAR complex by binding to the universal CAR complex via a first binding unit, and providing binding affinity to BCMA via a second binding unit. The methods can further involve treating a subject in need for a disease or disorder characterized by the expression of BCMA by administering an effective amount of a cell therapy comprising a plurality of cells comprising a universal CAR complex that has been functionalized to bind to BCMA, using the multi-specific antibodies of the invention, and thereby treating the disease or disorder in the subject.

Effective doses of the compositions of the present invention for the treatment of disease vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g., companion animals such as dogs, cats, horses, etc., laboratory mammals such as rabbits, mice, rats, etc., and the like. Treatment dosages can be titrated to optimize safety and efficacy.

Dosage levels can be readily determined by the ordinarily skilled clinician, and can be modified as required, e.g., as required to modify a subject's response to therapy. The amount of active ingredient that can be combined with the carrier materials to produce a single dosage form varies depending upon the host treated and the particular mode of administration. Dosage unit forms generally contain between from about 1 mg to about 500 mg of an active ingredient.

In some embodiments, the therapeutic dosage of the agent may range from about 0.0001 to 100 mg/kg, and more usually 0.01 to 5 mg/kg, of the host body weight. For example, dosages can be 1 mg/kg body weight or 10 mg/kg body weight or within the range of 1-10 mg/kg. An exemplary treatment regimen entails administration once every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

Typically, compositions are prepared as injectables, either as liquid solutions or suspensions; solid forms suitable for solution in, or suspension in, liquid vehicles prior to injection can also be prepared. The pharmaceutical compositions herein are suitable for intravenous or subcutaneous administration, directly or after reconstitution of solid (e.g., lyophilized) compositions. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the antibodies and antibody structures described herein can be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. The data obtained from these cell culture assays and animal studies can be used in formulating a dosage range that is not toxic for use in humans. The dosage of the antibodies described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

The compositions for administration will commonly comprise an antibody or other ablative agent dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

Also within the scope of the invention are kits comprising the active agents of the invention, and formulations thereof, and instructions for use. The kits can further contain a least one additional reagent, e.g., a chemotherapeutic drug, etc. Kits typically include a label indicating the intended use of the contents of the kit. The term label includes any writing, or recorded material supplied on or with the kit, or which otherwise accompanies the kit.

The invention now being fully described, it will be apparent to one of ordinary skill in the art that various changes and modifications can be made without departing from the spirit or scope of the invention.

EXAMPLES

The following examples are provided to illustrate certain embodiments and are not to be construed as limiting the scope of this disclosure in any way.

Example 1: CAR-T Mediated T-Cell Activation by Human Tumor Cell Lines

CAR-T cell activity was measured by transfecting Jurkat T lymphocyte cells with an anti-BCMA CAR and a 6×NFAT TK nano luciferase reporter. Transfected Jurkat cells were co-cultured for 24 hours with BCMA-positive NCI-H929, U266, and Daudi, or BCMA-negative K562 cells. Luciferase activity was measured using the Promega Nano-Glo Luciferase Assay System (catalog #N1110) and data was normalized to co-culture containing the CAR transfected Jurkat and BCMA-negative K562 cell lines. Statistical significance was determined using an unpaired, two-tailed t-test.

The results are provided in FIG. 8, Panel B.

FIG. 8, Panel A, is a schematic illustration of a CAR-T structure comprising an anti-BCMA extracellular binding domain comprising the VH sequence of SEQ ID NO: 12 (Clone ID No: 316302). FIG. 8, Panel B is a graph depicting T cell activity of Jurkat cells transfected with an NFAT luciferase reporter of T-cell signaling and an anti-BCMA 316302 CAR with NCI-H929 (*p=0.04), U266 (***p=0.0008), and Daudi (*p=0.03) cells. These results demonstrate that T-cell activation was specific to BCMA target binding, as co-culture of BCMA CAR Jurkat cells with the BCMA-negative K562 cell line did not result in appreciable luciferase reporter signal. Moreover, incubation of Jurkat cells, transfected with reporter but not the CAR, with BCMA positive NCI-H929, U266, and Daudi cells also did not result in appreciable luciferase reporter signal.

Example 2: Antibody Binding to BCMA Expressing Cells

Antibody binding to BCMA-expressing MMLS and H929 cells was assessed by flow cytometry. Test antibodies included bispecific constructs that bind to La protein (designated herein as "AntiX") and BCMA (designated herein as "BCMA_F7E"). As described elsewhere herein, bispecific constructs in accordance with embodiments of the invention can include a BCMA binding domain in a bivalent format, as depicted in FIG. 7, Panel A, right side; also referred to herein as "BCMA_F7E_F7E"; or a monovalent format, as depicted in FIG. 7, Panel B, right side; also referred to herein as "BCMA_F7E".

Binding experiments were conducted with the following constructs: AntiXBCMA_F7E, a bispecific antibody with a monovalent arm targeting BCMA (comprising SEQ ID NO: 12) and an La protein binding arm; AntiXBCMA_F7E_F7E, a bispecific antibody with a bivalent arm targeting BCMA (comprising SEQ ID NO: 12 in a bivalent configuration) and an La protein binding arm; AntiXGP120_F8A, a bispecific negative control antibody comprising an La protein binding arm and an arm that binds to GP120. Briefly, 300,000-500,000 cells were co-incubated with test antibody as listed in Table 1 and with commercial anti-BCMA antibody (Biolegend, 19F2) at 0.5 μl/test in 150 μl of FACS buffer (1×PBS, 2% FBS, 1 mM EDTA). Cells were subsequently washed twice and incubated with anti-IgG (PE) secondary antibody. After two additional washes, cells were processed on a Cytoflex instrument (Beckman Coulter) and analyzed using the FlowJo software package. Table 1, FIG. 9, Panel A, and FIG. 9**, Panel B show mean fluorescence intensity (MFI) for anti-IgG4 secondary antibody in MMLS and H929 cells.

TABLE 1

Mean Fluorescence intensity (MFI) of anti-IgG4 secondary antibody.

| Cell Type | Test Antibody (ng/ml) | AntiX** BCMA_F7E | AntiX** BCMA_F7E_F7E | AntiX** GP120_F8A |
|---|---|---|---|---|
| H929 | 200.000 | 14,064 | 52,932 | 5,616 |
| | 100.000 | 7,562 | 20,874 | 5,403 |
| | 50.000 | 6,070 | 10,927 | 5,239 |
| | 25.000 | 5,479 | 6,614 | 5,067 |
| | 12.500 | 5,186 | 5,682 | 4,988 |
| | 6.250 | 5,241 | 5,220 | 4,983 |
| | 3.130 | 5,168 | 5,141 | 5,018 |
| | 1.560 | 5,096 | 5,057 | 4,946 |
| | 0.781 | 5,056 | 5,023 | 4,874 |
| | 0.391 | 5,027 | 5,036 | 4,918 |
| | 0.195 | 5,031 | 5,008 | 4,917 |
| | 0.098 | 5,061 | 5,067 | 4,897 |
| | 0.000 | | 4,997 | |
| MM1.S | 200.000 | 3,183 | 7,339 | 1,994 |
| | 100.000 | 2,444 | 4,135 | 2,013 |
| | 50.000 | 2,176 | 2,928 | 2,010 |
| | 25.000 | 2,129 | 2,345 | 2,007 |
| | 12.500 | 2,120 | 2,176 | 2,003 |
| | 6.250 | 2,134 | 2,108 | 1,957 |
| | 3.130 | 2,107 | 2,073 | 1,998 |
| | 1.560 | 2,109 | 2,027 | 1,992 |
| | 0.781 | 2,064 | 2,010 | 1,997 |
| | 0.391 | 2,073 | 2,032 | 2,018 |
| | 0.195 | 2,072 | 2,009 | 1,976 |
| | 0.098 | 2,036 | 1,965 | 2,016 |
| | 0.000 | | 2,991 | |

Example 3: Competitive ELISA with APRIL and Test Antibodies

The avidity of bispecific BCMA-binding was tested in a competitive ELISA with BCMA's natural agonist, APRIL, also known as BAFF. In this assay, BCMA bound to the surface of plates was co-incubated with test antibody and APRIL, each at various concentrations. Clear Flat-Bottom Immuno Nonsterile 96-well plates (Corning, catalog no. 3455) were incubated overnight with 10 ng per well recombinant BCMA (R&D Systems, catalog no. 193-BC) in 100 μL PBS. Plates were washed and incubated with 1× Blocker BSA (Thermo Scientific, catalog no. 37525).

Test antibodies and recombinant APRIL (R&D Systems, catalog no. 560-AP) were incubated with BCMA-coated plates at the concentrations described in Table 2. Plates were washed and incubated with mouse anti-human IgG-HRP antibodies (Southern Biotech, catalog no. 9200-05). Plates were washed and developed with the Pierce TMB Substrate kit (Thermo Fisher, catalog no. 34021) according to the manufacturer's instructions. Absorbance was measured at 450 nm and 570 nm within 15 minutes. Table 2 shows A450-A570 values for each sample. FIG. 10, Panels A-C are graphs showing A450-A570 values for bispecific antibody constructs AntiXBCMA_F7E (pane A), AntiXBCMA_F7E_F7E (Panel B), and AntiXGP120_F8A (Panel C), respectively. More antibody binding is indicated by higher A450-A570 values. Even at higher APRIL concentration compared to bispecific antibody construct concentration, the AntiXBCMA_F7E_F7E construct, which comprises a BCMA-binding VH sequence in a bivalent configuration, demonstrates significant binding. The AntiXBCMA_F7E_F7E construct demonstrated stronger binding than the AntiXBCMA_F7E bispecific antibody construct, which comprises a BCMA-binding VH sequence in a monovalent configuration.

TABLE 2

(A450-A570) values indicating antibody binding to BCMA in the presence of BCMA agonist, APRIL.

| | Antibody | APRIL (ng/mL) | | | | | | | |
|---|---|---|---|---|---|---|---|---|---|
| Sample | (ng/mL) | 500.00 | 250.00 | 125.00 | 62.50 | 31.25 | 15.63 | 7.81 | 0.00 |
| AntiX** | 200.000 | 0.4818 | 0.9693 | 1.3717 | 2.0748 | 2.2860 | 2.4012 | 2.5108 | 2.4362 |
| BCMA_ | 20.000 | 0.1117 | 0.1479 | 0.2030 | 0.3589 | 0.4181 | 0.4825 | 0.4951 | 0.4656 |
| F7E | 2.000 | 0.0711 | 0.0837 | 0.0736 | 0.0834 | 0.0875 | 0.0867 | 0.0895 | 0.0894 |
| | 0.200 | 0.0745 | 0.0615 | 0.0643 | 0.0631 | 0.0620 | 0.0661 | 0.0643 | 0.0708 |
| | 0.020 | 0.0835 | 0.0617 | 0.0640 | 0.0629 | 0.0622 | 0.0614 | 0.0631 | 0.0630 |
| | 0.002 | 0.0836 | 0.0647 | 0.0660 | 0.0670 | 0.0580 | 0.0607 | 0.0607 | 0.0616 |
| AntiX** | 200.000 | 1.4064 | 2.2066 | 2.2959 | 2.4405 | 2.4211 | 2.3723 | 2.4742 | 2.4734 |
| BCMA_ | 20.000 | 0.2533 | 0.4130 | 0.6371 | 0.5369 | 0.8281 | 0.7776 | 0.7889 | 0.6478 |
| F7E_ | 2.000 | 0.0732 | 0.0921 | 0.1081 | 0.0980 | 0.1211 | 0.1066 | 0.1078 | 0.1071 |
| F7E | 0.200 | 0.0603 | 0.0614 | 0.0651 | 0.0595 | 0.0601 | 0.0587 | 0.0577 | 0.0676 |
| | 0.020 | 0.0631 | 0.0618 | 0.0557 | 0.0577 | 0.0551 | 0.0584 | 0.0578 | 0.0570 |
| | 0.002 | 0.0617 | 0.0607 | 0.0607 | 0.0569 | 0.0528 | 0.0620 | 0.0602 | 0.0578 |
| AntiX** | 200.000 | 0.0838 | 0.0682 | 0.0779 | 0.0701 | 0.0700 | 0.0774 | 0.0734 | 0.0755 |
| GP120_ | 20.000 | 0.0615 | 0.0603 | 0.0597 | 0.0586 | 0.0623 | 0.0630 | 0.0659 | 0.0687 |
| F8A | 2.000 | 0.0615 | 0.0591 | 0.0575 | 0.0628 | 0.0575 | 0.0580 | 0.0644 | 0.0656 |
| | 0.200 | 0.0590 | 0.0615 | 0.0614 | 0.0596 | 0.0589 | 0.0623 | 0.0597 | 0.0679 |
| | 0.020 | 0.0563 | 0.0600 | 0.0582 | 0.0611 | 0.0591 | 0.0615 | 0.0639 | 0.0639 |
| | 0.002 | 0.0617 | 0.0644 | 0.0595 | 0.0634 | 0.0600 | 0.0757 | 0.0685 | 0.0669 |

The invention claimed is:

1. A multi-specific antibody comprising:

(a) a first binding unit that binds to La protein, comprising:

(i) a heavy chain variable region comprising: a CDR1 sequence of SEQ ID NOs: 4 or 7, a CDR2 sequence of SEQ ID NO: 5, and a CDR3 sequence of SEQ ID NO: 6 or 8, in a human VH framework; and (ii) a light chain variable region comprising: a CDR1 sequence of SEQ ID NO: 9, a CDR2 sequence of SEQ ID NO: 10, and a CDR3 sequence of SEQ ID NO: 11, in a human VL framework; and (b) a second binding unit that binds to BCMA, comprising:

(i) an antigen-binding domain of an anti-BCMA heavy chain-only antibody, comprising a CDR1 sequence of SEQ ID NO: 1, a CDR2 sequence of SEQ ID NO: 2, and a CDR3 sequence of SEQ ID NO: 3, in a human VH framework, wherein the antigen-binding domain of the anti-BCMA heavy chain-only antibody is in a monovalent or bivalent configuration.

2. The multi-specific antibody of claim 1, wherein the heavy chain variable region and the light chain variable region of the first binding unit are on a common polypeptide subunit of the multi-specific antibody, and are connected by a linker sequence.

3. The multi-specific antibody of claim 1, wherein the heavy chain variable region and the light chain variable region of the first binding unit are on different polypeptide subunits of the multi-specific antibody.

4. The multi-specific antibody of claim 1, wherein the heavy chain variable region of the first binding unit comprises:

(i) a CDR1 sequence of SEQ ID NO: 4, a CDR2 sequence of SEQ ID NO: 5, and a CDR3 sequence of SEQ ID NO: 6; or (ii) a CDR1 sequence of SEQ ID NO: 7, a CDR2 sequence of SEQ ID NO: 5, and a CDR3 sequence of SEQ ID NO: 8.

5. The multi-specific antibody of claim 1, wherein the human VL framework is a human Vkappa framework; or wherein the human VL framework is a human Vlambda framework.

6. The multi-specific antibody of claim 1, wherein the heavy chain variable region of the first binding unit comprises a sequence having at least 95% identity to SEQ ID NO: 14 or SEQ ID NO: 15; or wherein the heavy chain variable region of the first binding unit comprises the sequence of SEO ID NO: 14 or SEO ID NO: 15.

7. The multi-specific antibody of claim 1, wherein the light chain variable region of the first binding unit comprises a sequence having at least 95% identity to SEQ ID NO: 16 or SEQ ID NO: 17; or wherein the light chain variable region of the first binding unit comprises the sequence of SEQ ID NO: 16 or SEQ ID NO: 17.

8. The multi-specific antibody of claim 1, wherein the antigen-binding domain of the anti-BCMA heavy chain-only antibody comprises a variable region sequence having at least 95% identity to the sequence of SEQ ID NO: 12; or wherein the antigen-binding domain of the anti-BCMA heavy chain-only antibody comprises a variable region sequence comprising the sequence of SEQ ID NO: 12.

9. The multi-specific antibody of claim 1, wherein the antigen-binding domain of the anti-BCMA heavy chain-only antibody is in a bivalent configuration, and comprises a linker sequence.

10. The multi-specific antibody of claim 9, wherein the linker sequence comprises a G4S linker sequence.

11. The multi-specific antibody of claim 1, wherein the first binding unit further comprises a heavy chain constant region comprising a CH1 domain, a hinge region, a CH2 domain, and a CH3 domain.

12. The multi-specific antibody of claim 11, wherein the CH2 domain comprises the sequence of a wild type human IgG4 CH2 domain (SEQ ID NO: 36); or wherein the CH2 domain comprises a variant human IgG4 CH2 domain comprising an F234A mutation, an L235A mutation, or both an F234A mutation and an L235A mutation.

13. The multi-specific antibody of claim 11, wherein the CH3 domain comprises the sequence of a wild type human IgG4 CH3 domain (SEQ ID NO: 38); wherein the CH3 domain comprises a variant human IgG4 CH3 domain comprising a T366W mutation (SEQ ID NO: 39); or wherein the CH3 domain comprises a variant human IgG4 CH3 domain comprising a T366S mutation, an L368A mutation, and a Y407V mutation (SEQ ID NO: 40).

14. The multi-specific antibody of claim 11, wherein the hinge region comprises the sequence of a wild type human IgG4 hinge region (SEQ ID NO: 32); or wherein the hinge region comprises a variant human IgG4 hinge region sequence comprising an S228P mutation (SEO ID NO: 33).

15. The multi-specific antibody of claim 14, further comprising a variant human IgG4 CH2 domain comprising an F234A mutation and an L235A mutation; or further comprising a variant human IgG4 CH3 domain comprising a T366W mutation; or further comprising a variant human IgG4 CH3 domain comprising a T366S mutation, an L368A mutation, and a Y407V mutation.

16. The multi-specific antibody of claim 1, wherein the first binding unit further comprises a light chain constant region comprising a human Vkappa constant region sequence; or wherein the first binding unit further comprises a light chain constant region comprising a human Vlambda constant region sequence.

17. The multi-specific antibody of claim 1, wherein the second binding unit further comprises a heavy chain constant region sequence, in the absence of a CH1 sequence.

18. The multi-specific antibody of claim 17, wherein the heavy chain constant region sequence comprises a CH2 domain and a CH3 domain, but no CH1 domain.

19. The multi-specific antibody of claim 18, wherein the CH2 domain comprises the sequence of a wild type human IgG4 CH2 domain (SEQ ID NO: 36); or wherein the CH2 domain comprises a variant human IgG4 CH2 domain comprising an F234A mutation, an L235A mutation, or both an F234A mutation and an L235A mutation.

20. The multi-specific antibody of claim 18, wherein the CH3 domain comprises the sequence of a wild type human IgG4 CH3 domain (SEQ ID NO: 38); or wherein the CH3 domain comprises a variant human IgG4 CH3 domain comprising a T366W mutation (SEO ID NO: 39); or wherein the CH3 domain comprises a variant human IgG4 CH3 domain comprising a T366S mutation, an L368A mutation, and a Y407V mutation (SEO ID NO: 40).

21. The multi-specific antibody of claim 18, wherein the multi-specific antibody further comprises a hinge region, wherein the hinge region comprises a wild type human IgG4 hinge region sequence (SEQ ID NO: 32); or wherein the hinge region comprises a variant human IgG4 hinge region sequence comprising an S228P mutation (SEO ID NO: 33).

22. The multi-specific antibody of claim 21, further comprising a variant human IgG4 CH2 domain comprising an F234A mutation and an L235A mutation.

23. The multi-specific antibody of claim 22, further comprising a variant human IgG4 CH3 domain comprising a T366W mutation; or further comprising a variant human IgG4 CH3 domain comprising a T366S mutation, an L368A mutation, and a Y407V mutation.

24. The multi-specific antibody of claim 1, which is bispecific.

25. A bispecific three-chain antibody-like molecule that binds to BCMA and La protein, comprising:

(i)
- (a) a first heavy chain polypeptide subunit comprising the sequence of SEQ ID NO: 18;
- (b) a second heavy chain polypeptide subunit comprising the sequence of SEQ ID NO: 24; and
- (c) a first light chain polypeptide subunit comprising the sequence of SEQ ID NO: 20; or (ii)
- (a) a first heavy chain polypeptide subunit comprising the sequence of SEQ ID NO: 18;
- (b) a second heavy chain polypeptide subunit comprising the sequence of SEQ ID NO: 26; and
- (c) a first light chain polypeptide subunit comprising the sequence of SEQ ID NO: 20; or (iii)
- (a) a first heavy chain polypeptide subunit comprising the sequence of SEQ ID NO: 21;
- (b) a second heavy chain polypeptide subunit comprising the sequence of SEO ID NO: 24; and
- (c) a first light chain polypeptide subunit comprising the sequence of SEQ ID NO: 23; or (iv)
- (a) a first heavy chain polypeptide subunit comprising the sequence of SEO ID NO: 21;
- (b) a second heavy chain polypeptide subunit comprising the sequence of SEQ ID NO: 26; and
- (c) a first light chain polypeptide subunit comprising the sequence of SEQ ID NO: 23; or (v)
- (a) a first heavy chain polypeptide subunit comprising the sequence of SEQ ID NO: 19;
- (b) a second heavy chain polypeptide subunit comprising the sequence of SEQ ID NO: 25; and
- (c) a first light chain polypeptide subunit comprising the sequence of SEO ID NO: 20; or (vi)
- (a) a first heavy chain polypeptide subunit comprising the sequence of SEQ ID NO: 19;
- (b) a second heavy chain polypeptide subunit comprising the sequence of SEO ID NO: 27; and
- (c) a first light chain polypeptide subunit comprising the sequence of SEQ ID NO: 20; or (vii)
- (a) a first heavy chain polypeptide subunit comprising the sequence of SEO ID NO: 22;
- (b) a second heavy chain polypeptide subunit comprising the sequence of SEO ID NO: 25; and
- (c) a first light chain polypeptide subunit comprising the sequence of SEQ ID NO: 23; or (viii)
- (a) a first heavy chain polypeptide subunit comprising the sequence of SEQ ID NO: 22;
- (b) a second heavy chain polypeptide subunit comprising the sequence of SEQ ID NO: 27; and
- (c) a first light chain polypeptide subunit comprising the sequence of SEQ ID NO: 23.

26. A method of treatment, comprising administering to an individual in need an effective dose of the antibody of claim 1, or a pharmaceutical composition comprising the antibody of claim 1.

* * * * *